US005846517A

United States Patent [19]
Unger

[11] Patent Number: 5,846,517
[45] Date of Patent: Dec. 8, 1998

[54] METHODS FOR DIAGNOSTIC IMAGING USING A RENAL CONTRAST AGENT AND A VASODILATOR

[75] Inventor: Evan C. Unger, Tucson, Ariz.

[73] Assignee: ImaRx Pharmaceutical Corp., Tucson, Ariz.

[21] Appl. No.: 790,550

[22] Filed: Jan. 30, 1997

Related U.S. Application Data

[63] Continuation-in-part of Ser. No. 712,173, Sep. 11, 1996.

[51] Int. Cl.⁶ ................................................. A61K 49/04
[52] U.S. Cl. ............................................................ 424/9.52
[58] Field of Search .............................. 424/9.52, 9.51, 424/9.5; 600/458

[56] References Cited

U.S. PATENT DOCUMENTS

| | | | |
|---|---|---|---|
| 3,015,128 | 1/1962 | Sommerville et al. | 18/2.6 |
| 3,293,114 | 12/1966 | Kenaga et al. | 162/168 |
| 3,479,811 | 11/1969 | Walters | 57/153 |
| 3,488,714 | 1/1970 | Walters et al. | 161/161 |
| 3,532,500 | 10/1970 | Priest et al. | 96/91 |
| 3,594,326 | 7/1971 | Himmel et al. | 252/316 |
| 3,615,972 | 10/1971 | Morehouse et al. | 156/79 |
| 3,650,831 | 3/1972 | Jungermann et al. | 134/27 |
| 3,732,172 | 5/1973 | Herbig et al. | 252/316 |
| 3,873,564 | 3/1975 | Schneider et al. | 260/309.6 |
| 3,945,956 | 3/1976 | Garner | 260/2.5 B |
| 3,960,583 | 6/1976 | Netting et al. | 106/122 |
| 3,968,203 | 7/1976 | Spitzer et al. | 424/47 |
| 4,027,007 | 5/1977 | Messina | 424/46 |
| 4,089,801 | 5/1978 | Schneider | 252/316 |
| 4,108,806 | 8/1978 | Cohrs et al. | 521/54 |
| 4,138,383 | 2/1979 | Rembaum et al. | 260/29.7 H |
| 4,162,282 | 7/1979 | Fulwyler et al. | 264/9 |
| 4,179,546 | 12/1979 | Garner et al. | 521/56 |
| 4,192,859 | 3/1980 | Mackaness et al. | 424/5 |
| 4,224,179 | 9/1980 | Schneider | 252/316 |

(List continued on next page.)

FOREIGN PATENT DOCUMENTS

| | | |
|---|---|---|
| 641363 | 3/1990 | Australia . |
| B-30351/89 | 3/1993 | Australia . |
| 0 107 559 | 5/1984 | European Pat. Off. . |
| 0 077 752 B1 | 3/1986 | European Pat. Off. . |
| 0 243 947 | 4/1987 | European Pat. Off. . |
| 0 231 091 | 8/1987 | European Pat. Off. . |
| 0 272 091 | 6/1988 | European Pat. Off. . |
| 0 320 433 A2 | 12/1988 | European Pat. Off. . |
| 0 324 938 | 7/1989 | European Pat. Off. . |
| 0 338 971 | 10/1989 | European Pat. Off. . |
| 357163 A1 | 3/1990 | European Pat. Off. . |
| 0 361 894 | 4/1990 | European Pat. Off. . |
| 0 216 730 | 1/1991 | European Pat. Off. . |

(List continued on next page.)

OTHER PUBLICATIONS

Desir, et al., "Assessment of Regional Myocardial Perfusion with Myacardial Contrast Echocardiography in a Canine Model of Varying Degrees of Coronary Stenosis", American Heart Journal, vol. 127, No. 1, pp. 56–63, Jan. 1994.

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", Inorganic Chemistry, vol. 13, No. 3, pp. 568–574 (1974).

(List continued on next page.)

*Primary Examiner*—Gary E. Hollinden
*Assistant Examiner*—Michael G. Hartley
*Attorney, Agent, or Firm*—Woodcock Washburn Kurtz Mackiewicz & Norris LLP

[57] ABSTRACT

A method for providing an image of an internal region of a patient has been developed. The method reduces imaging artifacts by providing enhanced contrast between tissue and blood during imaging. The method comprises administering to a patient a contrast agent in combination with a renal vasodilator and performing ultrasound imaging of the region. Renal disease, including renal arterial stenosis, may be diagnosed using the method.

32 Claims, 1 Drawing Sheet

U.S. PATENT DOCUMENTS

| | | | |
|---|---|---|---|
| 4,229,360 | 10/1980 | Schneider et al. | 260/403 |
| 4,265,251 | 5/1981 | Tickner | 128/660 |
| 4,276,885 | 7/1981 | Tickner et al. | 128/660 |
| 4,310,505 | 1/1982 | Baldeschwieler et al. | 424/1 |
| 4,310,506 | 1/1982 | Baldeschwieler et al. | 424/1 |
| 4,315,514 | 2/1982 | Drewes et al. | 128/653 |
| 4,331,654 | 5/1982 | Morris | 424/38 |
| 4,342,826 | 8/1982 | Cole | 435/7 |
| 4,344,929 | 8/1982 | Bonsen et al. | 424/15 |
| 4,420,442 | 12/1983 | Sands | 264/13 |
| 4,421,562 | 12/1983 | Sands et al. | 106/75 |
| 4,426,330 | 1/1984 | Sears | 260/403 |
| 4,428,924 | 1/1984 | Millington | 424/4 |
| 4,442,843 | 4/1984 | Rasor et al. | 128/660 |
| 4,466,442 | 8/1984 | Hilmann et al. | 128/653 |
| 4,533,254 | 8/1985 | Cook et al. | 366/176 |
| 4,534,899 | 8/1985 | Sears | 260/403 |
| 4,540,629 | 9/1985 | Sands et al. | 428/402 |
| 4,544,545 | 10/1985 | Ryan et al. | 424/1.1 |
| 4,549,892 | 10/1985 | Baker et al. | 65/21.4 |
| 4,569,836 | 2/1986 | Gordon | 424/1.1 |
| 4,572,203 | 2/1986 | Feinstein | 128/661 |
| 4,586,512 | 5/1986 | Do-huu et al. | 128/660 |
| 4,603,044 | 7/1986 | Geho et al. | 424/9 |
| 4,615,879 | 10/1986 | Runge et al. | 424/9 |
| 4,620,546 | 11/1986 | Aida et al. | 128/660 |
| 4,646,756 | 3/1987 | Watmough et al. | 128/804 |
| 4,657,756 | 4/1987 | Rasor et al. | 424/9 |
| 4,658,828 | 4/1987 | Dory | 128/660 |
| 4,675,310 | 6/1987 | Chapman et al. | 514/6 |
| 4,681,119 | 7/1987 | Rasor et al. | 128/660 |
| 4,684,479 | 8/1987 | D'Arrigo | 252/307 |
| 4,689,986 | 9/1987 | Carson et al. | 73/19 |
| 4,718,433 | 1/1988 | Feinstein | 128/660 |
| 4,728,575 | 3/1988 | Gamble et al. | 428/402.2 |
| 4,728,578 | 3/1988 | Higgins et al. | 428/462 |
| 4,731,239 | 3/1988 | Gordon | 424/9 |
| 4,737,323 | 4/1988 | Martin et al. | 264/4.3 |
| 4,774,958 | 10/1988 | Feinstein | 128/660.01 |
| 4,775,522 | 10/1988 | Clark, Jr. | 424/9 |
| 4,776,991 | 10/1988 | Farmer et al. | 264/4.3 |
| 4,781,871 | 11/1988 | West, III et al. | 264/4.3 |
| 4,789,501 | 12/1988 | Day et al. | 252/645 |
| 4,790,891 | 12/1988 | Halliday et al. | 149/2 |
| 4,822,534 | 4/1989 | Lencki et al. | 264/4.3 |
| 4,830,858 | 5/1989 | Payne et al. | 424/450 |
| 4,844,882 | 7/1989 | Widder et al. | 424/9 |
| 4,863,717 | 9/1989 | Keana | 424/9 |
| 4,865,836 | 9/1989 | Long, Jr. | 424/5 |
| 4,877,561 | 10/1989 | Iga et al. | 264/4.3 |
| 4,893,624 | 1/1990 | Lele | 128/399 |
| 4,895,719 | 1/1990 | Radhakrishnan | 424/45 |
| 4,898,734 | 2/1990 | Mathiowitz et al. | 424/426 |
| 4,900,540 | 2/1990 | Ryan et al. | 424/9 |
| 4,921,706 | 5/1990 | Roberts et al. | 424/450 |
| 4,927,623 | 5/1990 | Long, Jr. | 424/5 |
| 4,933,121 | 6/1990 | Law et al. | 264/4.3 |
| 4,938,947 | 7/1990 | Nicolau et al. | 424/1.1 |
| 4,957,656 | 9/1990 | Cerny et al. | 252/311 |
| 4,981,692 | 1/1991 | Popescu et al. | 424/422 |
| 4,985,550 | 1/1991 | Charpiot et al. | 536/18.4 |
| 4,987,154 | 1/1991 | Long, Jr. | 514/772 |
| 4,993,415 | 2/1991 | Long | 128/653 A |
| 4,996,041 | 2/1991 | Arai et al. | 424/9 |
| 5,000,960 | 3/1991 | Wallach | 424/450 |
| 5,004,611 | 4/1991 | Leigh | 424/450 |
| 5,008,050 | 4/1991 | Cullis et al. | 264/4.3 |
| 5,013,556 | 5/1991 | Woodle et al. | 424/450 |
| 5,019,370 | 5/1991 | Jay et al. | 424/4 |
| 5,045,304 | 9/1991 | Schneider et al. | 424/9 |
| 5,049,388 | 9/1991 | Knight et al. | 424/450 |
| 5,078,994 | 1/1992 | Nair et al. | 424/501 |
| 5,088,499 | 2/1992 | Unger | 128/662.2 |
| 5,114,703 | 5/1992 | Wolf et al. | 424/5 |
| 5,123,414 | 6/1992 | Unger | 128/654 |
| 5,135,000 | 8/1992 | Akselrod et al. | 128/662.02 |
| 5,137,928 | 8/1992 | Erbel et al. | 521/56 |
| 5,141,738 | 8/1992 | Rasor et al. | 424/2 |
| 5,147,631 | 9/1992 | Glajch et al. | 424/9 |
| 5,149,319 | 9/1992 | Unger | 604/22 |
| 5,171,755 | 12/1992 | Kaufman | 514/759 |
| 5,186,922 | 2/1993 | Shell et al. | 128/654 |
| 5,190,982 | 3/1993 | Erbel et al. | 521/56 |
| 5,192,549 | 3/1993 | Barenolz et al. | 424/450 |
| 5,194,266 | 3/1993 | Abra et al. | 424/450 |
| 5,195,520 | 3/1993 | Schlief et al. | 128/660.02 |
| 5,196,183 | 3/1993 | Yudelson et al. | 424/9 |
| 5,198,225 | 3/1993 | Meybeck et al. | 424/450 |
| 5,205,287 | 4/1993 | Erbel et al. | 128/632 |
| 5,205,290 | 4/1993 | Unger | 128/653.4 |
| 5,209,720 | 5/1993 | Unger | 604/22 |
| 5,213,804 | 5/1993 | Martin et al. | 424/450 |
| 5,215,680 | 6/1993 | D'Arrigo | 252/307 |
| 5,219,538 | 6/1993 | Henderson et al. | 428/402.2 |
| 5,228,446 | 7/1993 | Unger et al. | 128/662.02 |
| 5,230,882 | 7/1993 | Unger | 424/9 |
| 5,247,935 | 9/1993 | Cline et al. | 128/653.2 |
| 5,271,928 | 12/1993 | Schneider et al. | 424/9 |
| 5,281,408 | 1/1994 | Unger | 424/4 |
| 5,305,757 | 4/1994 | Unger et al. | 128/662.02 |
| 5,310,540 | 5/1994 | Giddey et al. | 424/9 |
| 5,315,997 | 5/1994 | Widder et al. | 128/653.3 |
| 5,315,998 | 5/1994 | Tachibana et al. | 128/660.01 |
| 5,316,771 | 5/1994 | Barenholz et al. | 424/450 |
| 5,334,381 | 8/1994 | Unger | 424/9 |
| 5,344,930 | 9/1994 | Riess et al. | 544/84 |
| 5,350,571 | 9/1994 | Kaufman et al. | 424/9 |
| 5,352,435 | 10/1994 | Unger | 424/9 |
| 5,354,549 | 10/1994 | Klaveness et al. | 424/3 |
| 5,358,702 | 10/1994 | Unger | 424/9 |
| 5,362,478 | 11/1994 | Desai et al. | 424/9 |
| 5,380,519 | 1/1995 | Schneider et al. | 424/9 |
| 5,393,524 | 2/1995 | Quay | 424/9 |
| 5,409,688 | 4/1995 | Quay | 424/9 |
| 5,410,516 | 4/1995 | Uhlendorf et al. | 367/7 |
| 5,413,774 | 5/1995 | Schneider et al. | 424/9.51 |
| 5,425,366 | 6/1995 | Reinhardt et al. | 128/662.02 |
| 5,433,204 | 7/1995 | Olson | 128/661.08 |
| 5,445,813 | 8/1995 | Schneider et al. | 424/9.51 |
| 5,456,900 | 10/1995 | Unger | 424/9.4 |
| 5,469,854 | 11/1995 | Unger et al. | 128/662.02 |
| 5,470,582 | 11/1995 | Supersaxo et al. | 424/489 |
| 5,487,390 | 1/1996 | Cohen et al. | 128/662.02 |
| 5,496,535 | 3/1996 | Kirkland | 424/9.37 |
| 5,498,421 | 3/1996 | Grinstaff et al. | 424/450 |
| 5,501,863 | 3/1996 | Rössling et al. | 424/489 |
| 5,502,094 | 3/1996 | Moore et al. | 524/145 |
| 5,505,932 | 4/1996 | Grinstaff et al. | 424/9.3 |
| 5,527,521 | 6/1996 | Unger | 424/93 |
| 5,529,766 | 6/1996 | Klaveness et al. | 424/9.52 |
| 5,531,980 | 7/1996 | Schneider et al. | 424/9.52 |
| 5,536,489 | 7/1996 | Lohrmann et al. | 424/9.52 |
| 5,536,490 | 7/1996 | Klaveness et al. | 424/9.52 |
| 5,540,909 | 7/1996 | Schutt | 424/9.52 |
| 5,542,935 | 8/1996 | Unger et al. | 604/190 |
| 5,547,656 | 8/1996 | Unger | 424/9.4 |
| 5,552,133 | 9/1996 | Lambert et al. | 424/9.52 |
| 5,556,610 | 9/1996 | Yan et al. | 424/9.52 |
| 5,558,092 | 9/1996 | Unger et al. | 128/660.03 |
| 5,558,094 | 9/1996 | Quay | 128/662.02 |
| 5,558,856 | 9/1996 | Klaveness et al. | 424/9.37 |
| 5,560,364 | 10/1996 | Porter | 128/662.02 |

| | | | |
|---|---|---|---|
| 5,562,893 | 10/1996 | Lohrmann | 424/9.52 |
| 5,567,413 | 10/1996 | Klaveness et al. | 424/9.51 |
| 5,567,414 | 10/1996 | Schneider et al. | 424/9.52 |
| 5,567,765 | 10/1996 | Moore et al. | 524/801 |
| 5,569,449 | 10/1996 | Klaveness et al. | 424/9.51 |
| 5,573,751 | 11/1996 | Quay | 424/9.52 |
| 5,578,292 | 11/1996 | Schneider et al. | 424/9.51 |
| 5,585,112 | 12/1996 | Unger et al. | 424/450 |
| 5,605,673 | 2/1997 | Schutt et al. | 424/9.51 |
| 5,606,973 | 3/1997 | Lambert et al. | 128/662.02 |
| 5,614,169 | 3/1997 | Klaveness et al. | 424/9.52 |
| 5,620,689 | 4/1997 | Allen et al. | 424/178.1 |
| 5,626,833 | 5/1997 | Schutt et al. | 424/9.52 |
| 5,639,443 | 6/1997 | Schutt et al. | 424/9.52 |
| 5,643,553 | 7/1997 | Schneider et al. | 424/9.52 |
| 5,672,585 | 9/1997 | Pierschbacher et al. | 514/11 |
| 5,676,928 | 10/1997 | Klaveness et al. | 424/9.321 |
| 5,686,060 | 11/1997 | Schneider et al. | 424/9.52 |
| 5,707,606 | 1/1998 | Quay | 424/9.52 |
| 5,707,607 | 1/1998 | Quay | 424/9.52 |
| B1 4,229,360 | 11/1991 | Schneider et al. | 260/403 |

FOREIGN PATENT DOCUMENTS

| | | |
|---|---|---|
| 0 467 031 A2 | 5/1991 | European Pat. Off. . |
| 441468 A2 | 8/1991 | European Pat. Off. . |
| 0 357 164 B1 | 10/1991 | European Pat. Off. . |
| 0 458 745 A1 | 11/1991 | European Pat. Off. . |
| 0 314 764 B1 | 9/1992 | European Pat. Off. . |
| 0 554 213 A1 | 8/1993 | European Pat. Off. . |
| 0 586 875 | 3/1994 | European Pat. Off. . |
| 0 727 225 A2 | 8/1996 | European Pat. Off. . |
| 62-286534 | 12/1987 | Japan . |
| SHO 63-60943 | 3/1988 | Japan . |
| 1044680 | 10/1966 | United Kingdom . |
| 2193095 | 2/1988 | United Kingdom . |
| WO 80/02365 | 11/1980 | WIPO . |
| WO 82/01642 | 5/1982 | WIPO . |
| US85/01161 | 3/1985 | WIPO . |
| WO 86/00238 | 1/1986 | WIPO . |
| WO 86/01103 | 2/1986 | WIPO . |
| WO 89/05040 | 6/1989 | WIPO . |
| WO 90/01952 | 3/1990 | WIPO . |
| WO 90/04384 | 5/1990 | WIPO . |
| WO 90/04943 | 5/1990 | WIPO . |
| WO 91/00086 | 1/1991 | WIPO . |
| WO 91/12823 | 9/1991 | WIPO . |
| WO 91/15244 | 10/1991 | WIPO . |
| WO 92/10166 | 6/1992 | WIPO . |
| WO 92/11873 | 7/1992 | WIPO . |
| WO 92/17212 | 10/1992 | WIPO . |
| WO 92/17213 | 10/1992 | WIPO . |
| WO 92/17436 | 10/1992 | WIPO . |
| WO 92/17514 | 10/1992 | WIPO . |
| WO 92/21382 | 10/1992 | WIPO . |
| WO 93/00933 | 1/1993 | WIPO . |
| WO 93/05819 | 1/1993 | WIPO . |
| WO 93/06869 | 4/1993 | WIPO . |
| WO 93/13809 | 7/1993 | WIPO . |
| WO 93/17718 | 9/1993 | WIPO . |
| WO 93/20802 | 10/1993 | WIPO . |
| WO 94/06477 | 3/1994 | WIPO . |
| WO 94/07539 | 4/1994 | WIPO . |
| WO 94/09829 | 5/1994 | WIPO . |
| WO 94/16739 | 8/1994 | WIPO . |
| WO 94/21302 | 9/1994 | WIPO . |
| WO 94/28780 | 12/1994 | WIPO . |
| WO 95/06518 | 3/1995 | WIPO . |
| WO 95/07072 | 3/1995 | WIPO . |
| WO 95/23615 | 9/1995 | WIPO . |
| WO 96/04018 | 2/1996 | WIPO . |
| WO 96/09793 | 4/1996 | WIPO . |
| WO 96/36286 | 11/1996 | WIPO . |

OTHER PUBLICATIONS

Thanassi, "Aminomalonic Acid: Spontaneous Decarboxylation and Reaction with 5–Deoxypyridoxal", *Biochemistry*, vol. 9, No. 3, pp. 525–532 (1970).

Stelmashok et al., *Koordinatsionnaya Khimiya*, vol. 3, No. 4, pp. 524–527 (1977) (Russian and English language versions).

Mayhew et al., "High–Pressure Continuous–Flow System for Drug Entrapment in Liposomes", *Methods in Enzymology*, vol. 149, pp. 64–77 (1987).

Mayhew et al., "Characterization of Liposomes Prepared Using a Microemulsifier", *Biochimica et Biophysica Acta*, vol. 775, pp. 169–174 (1984).

Hope et al., "Production of Large Unilamellar Vesicles by a Rapid Extrusion Procedure: Characterization of Size Distribution, Trapped Volume, and Ability to Maintain a Membrane Potential", *Biochimica et Biophysica Acts*, 812:55–65 (1985).

Mayer et al., "Vesicles of Variable Size Produced by a Rapid Extrusion Procedure", *Biochimica et Biophysica Acta*, vol. 858, pp. 161–168 (1986).

Cheng, et al., "The Production and Evaluation of Contrast–Carrying Lipsomes Made with an Automatic High Pressure System", *Investigative Radiology*, vol. 22, pp. 47–55 (1987).

Jain, et al., *Introduction to Biological Membranes*, Ch. 9, pp. 192–231 (J. Wiley and Sons, N.Y. 1980).

Sigel, H., ed., *Metal Ions in Biological Systems: Antibiotics and Their Complexes*, vol. 19 (Marcel Dekker, N.Y. 1985).

Nayar et al., "Generation of Large Unilamellar Vesicles From Long–chain Saturated Phosphatidylcholines by Extrusion Technique", *Biochimica et Biophysica Acta*, vol. 986, pp. 200–206 (1989).

Hope et al., "Generation of Multilamellar and Unilamellar Phospholipid Vesicles", *Chemistry and Physics of Lipids*, vol. 40, pp. 89–107 (1986).

Mattrey et al., "Perfluorochemicals as US Contrast Agents for Tumor–Imaging and Hepatosplenography: Preliminary Clinical Results", *Radiology*, vol. 163, pp. 339–343 (1987).

Mattrey et al., "Perfluoroctylbromide: A Liver/Spleen–Specific and Tumor Imaging Ultrasound Contrast Material", *Radiology*, vol. 145, pp. 759–762 (1982).

Keller et al., "Successful Left Ventricular Opacification Following Peripheral Venous Injection of Sonicated Contrast Agent: An Experimental Evaluation", *LV Contrast Echocardiography*, vol. 114, No. 3, pp. 570–575 (1987).

Feinstein et al., "Two–Dimensional Contrast Echocardiography, I: In Vitro Development and Quantitative Analysis of Echo Contrast Agents", *JAAC*, vol. 3, No. 1, pp. 14–20 (1984).

Ten Cate et al., "Two–Dimensional Contract Echocardiography, II: Transpulmonary Studies", *JACC*, vol. 3, No. 1, pp. 21–27 (1984).

Unger et al., "Hepatic Metastases: Liposomal Gd–DTPA–enhanced MR Imaging", *Radiology*, vol. 171, pp. 81–85 (1989).

Deamer et al., "Permeability of Lipid Bilayers to Water and Ionic Solutes", *Chemistry and Physics of Lipids*, vol. 40, pp. 167–188 (1986).

Gutknecht et al., "Diffusion of Carbon Dioxide Through Lipid Bilayer Membranes: Effect of Carbonic Anhydrase, Bicarbonate, and Unstirred Layers", *Chemical Abstracts*, 87:34772q (1977).

Scarpa et al., "Cation Permeability of Liposomes as a Function of the Chemical Composition of the Lipid Bilayers", *Biochimica et Biophysica Acts,* vol. 241, pp. 789–797 (1971).

MacNaughton et al., "Effects of Gaseous Anesthetics and Inert Gases on the Phase Transition in Smectic Mesophases of Dipalmitoyl Phosphatidylcholine", *Biochimica et Biophysica Acta,* vol. 597, pp. 193–198 (1980).

Tilcock et al., "Liposomal Gd–DTPA: Preparation and Characterization of Relaxivity", *Radiology,* vol. 171, pp. 77–80 (1989).

Mann et al., "Formation of Iron Oxides in Unilamellar Vesicles", *Journal of Colloid and Interface Science,* vol. 122, No. 2, pp. 326–335 (1988).

Anderson et al., "Manganese (III) Complexes in Oxidative Decarboxylation of Acids", *J. Am. Chem. Soc.,* vol. 92, No. 8, pp. 2450–2460 (1970).

Muhlradt et al., "Vitamin B6 Analogs: An Improved Synthesis of 5–Deoxypyridoxal", *New Compounds,* vol. 10, pp. 129–130 (1967).

Chapman D., "Physiochemical Properties of Phospholipids and Lipid Water Systems", *Liposome Technology,* Gregoriadis, G., ed., vol. 1, pp. 1–19 (CRC Press, Boca Raton, FL, 1984).

Violante et al., "Particulate Suspensions as Ultrasonic Contrast Agents for Liver and Spleen", *Inv. Rad.,* vol. 23, pp. S294–S297, Sep. 1988.

Fritzsch et al., "Preclinical and Clinical Results with an Ultrasonic Contrast Agent", *Inv. Rad.,* vol. 23, pp. S302–S305, Sep. 1988.

Brochure, *Experience,* Sonicator™, Heat Systems–Ultrasonics, Inc. (1987).

M. Ostro, "Liposomes", Marcel Dekker, New York, pp. 102–103 (1983).

Fukuda et al., "Polymer–Encased Vesicles Derived from Diotadecyldimethylammonium Methacrylate", *J. Am. Chem. Soc.,* vol. 108, pp. 2321–2327 (1986).

Regen, "Polymerized Vesicles", *J. Am. Chem. Soc.,* vol. 102, pp. 6638–6640 (1989).

Rose, A. and Rose, E., "The Condensed Chemical Dictionary", Reinhold Publishing, New York, pp. 728 and 743 (1966).

A.G. Belykh, *Farmakol Toksikol. (MOSC),* vol. 44(3), pp. 322–326 (1981) (abstract).

J. Vion–Dury et al., *J. Pharmacol. Exper. Ther.,* vol. 250(3), pp. 1113–1118 (1989) (abstract).

M.R. Zalutsky et al., *Invest. Radiol.,* vol. 22(2), pp. 141–147 (1987) (abstract).

Crowe et al., *Archives of Biochemistry and Biophysics,* vol. 242, pp. 240–247 (1985).

Crowe et al., *Archives of Biochemistry and Biophysics,* vol. 220, pp. 477–484 (1983).

Dorland's Illustrated Medical Dictionary, p. 946, 27th ed. (W.B. Saunders Company, Philadelphia 1988).

*Liposome Technology,* Gregoriadis, G., ed., vol. I, pp. 1–18, 30–35, 51–65 and 79–107 (CRC Press Inc., Boca Raton, FL, (1984).

Madden et al., *Chemistry and Physics of Lipids,* vol. 53, pp. 37–46 (1990).

Sinkula et al., *J. Pharm. Sci.,* vol. 64, pp. 181–210 (1975).

Shiina et al., "Hyperthermiably Low–frequency Synthesized Ultrasound", *IEEE Engineering,* pp. 879–880, vol. 2 (1988) (abstract).

McAvoy et al, *IEEE Engineering, Ultrasonics Symposium Proceedings,* vol. 2, pp. 677–1248 (1989) (abstract).

Chapman et al., "Biomembrane Phase Transitions", *J. Biol. Chem.,* 1974, 249:2512–2521.

Hug et al., "Lipsomes for the Transformation of Eukaryotic Cells", *Biochimica et Biophysica Acta,* 1991, 1097:1–17.

Marsh, *CRC Handbook of Lipid Bilayers* (CRC Press, Boca Raton, FL 1990) pp. 139–141.

Szoka et al., "Procedure for Preparation of Liposomes With Large Internal Aqueous Space . . . ", *Proc. Natl. Acad. Sci.* 1978, 75:4194–4198.

Acoustic Imaging, AI5200; Convex Curved Linear Array Ultrasound Transducers Operator's Manual, Nov. 20, 1989, 4700–0003–1C, p. 4.

Bangham et al., "Diffusion of Univalent Ions across the Lamellae of Swollen Phospholipids", *J. Mol. Biol.,* 1965, 13:238–252.

Carson et al., *Ultrasound in Med. & Biol.* 3, 1978, 341–350.

Kost et al., *Polymers in Medicine II: Biomedical and Pharmaceutical Applications,* "Ultrasonic Modulated Drug Delivery Systems", Chiellini et al., ed., (Plenum Press, New York and London), pp. 387–396 (1985).

deGier et al., "Relations Between Liposomes and Biomembranes", *Annals of the New York Academy of Sciences,* 1978, 308:85–99.

Felgner et al., "Lipofection: A highly efficient, lipid–mediated DNA–transfection procedure", *Proc. Natl. Acad. Sci.,* 1987, 84:7413–7417.

Gabizon et al., "Liposome formulations with prolonged circulation time in blood and enhanced uptake by tumors", *Proc. Natl. Acad. Sci.,* 1988, 85:6949–6953.

Garelli, et al., *Biochimica et Biophysica Acta,* vol. 1127:41–48 (1992).

Kawai et al., "New Procedure for DNA Transfection with Polycation and Dimethyl Sulfoxide", *Molecular and Cellular Biology,* 1984, 4:1172–1174.

Kuo et al., "Metallocene Antitumor Agents. Solution and Solid–State Molybdenocene Coordination . . . ", *J. Am. Chem. Soc.,* 1991, 113:9027–9045.

*Mammalian Cell Biotechnology: A Practical Approach,* M. Butler, 1991 (Oxford University Press, New York), pp. 57–70.

Mathiowitz et al., "Photochemical Rupture of Microcapsules: A Model System", *Journal of Applied Polymer Science,* 1981, 26:810–822.

May et al., "Cationic Liposomes Enable Bovine Herpesvirus Type 2 DNA to Infect Cells", *Acta virol.,* 1991, 35:107.

Poznansky et al., "Biologica Approaches to the Controlled Delivery of Drugs: A Critical Review", *Pharmacol, Rev.,* 1984, 36:277–336.

Sato et al., "Recent Aspects in the Use of Lipsomes in Biotechnology and Medicine", *Prog. Lipid Res.* 1992, 4:345–372.

Simons et al., "Antisense c–myb oligunucleotides inhibit intimal arterial smooth muscle cell accumulation in vivo", *Nature,* 1992, 359:67–70.

Thompson, Larry, "At Age 2, Gene Therapy Enters a Growth Phase", *Science* 1992, 258:744–746.

Trubetskoy et al. "Cationic liposomes enhance targeted delivery and expression of exogenous DNA . . . ", *Biochimica et Biophysica Acta* 1992, 131:311–313.

Umemura et al., "Studies on Sonodynamic Cancer Therapy", *IEEE,* 1992, O–7803–0785, pp. 354–355.

Williams, "Human Gene Therapy: Searching for Better Vectors", *ASM News* [American Society for Microbiology] 1992, 58:67–69

Woodle et al., "Versatility in lipid compositions showing prolonged circulation . . . ", Biochimica et Biophysica Acta 1992, 1105:193–200.

Zhou et al., "Targeted delivery of DNA by liposomes and polymers", J. of Controlled Release 1992, 19:269–274.

Mathiowitz et al., "Polyanhydride Microspheres as Drug Carriers", Journal of Applied Polymer Science, vol. 35, pp. 755–774 (1988).

Sankaram et al., "Cholesterol–Induced Fluid–Phase Immiscibility in Membranes", Proc. Natl. Acad. Sci., vol. 88, pp. 8686–8690 (1991).

Scientific Apparatus Catalog, 92/93 (VWR Scientific, 1991), "Syringes", pp. 1511–1513; Filtration, Syringe Filters, pp. 766–768; Filtration, Membranes, pp. 750–753, Filtration, Filter Holders, p. 744.

Gramiak et al., Radiology, "Detection of Intracardiac Blood Flow by Pulsed Echo–Ranging", pp. 415–418 (1971).

Feigenbaum et al., Circulation, "Identification of Ultrasound Echoes from the Left Ventricle by Use of Intracardiac Injections of Indocyanine Green", vol. XL1, pp. 615–621 (1970).

Santaella, et al., FEBS 13463, "Extended In Vivo Blood Circulation Time of Fluorinated Liposomes", vol. 336, No. 3, pp. 481–484 (1993).

Brown and Langer, Annual Review Medicine, 1988, 39:22129, Annual Review, Inc., "Transdermal Delivery of Drugs", pp. 221–229.

Moseley, et al., Microbubbles: A Novel MR Susceptibility Contrast Agent, abstract, 1991 Napa, California Meeting of the Society for Magnetic Resonance in Medicine.

Ter–Pogossian Tomography, Kee, et al., n, "Physical Principles and Instrumentation", Computed Body eds., Raven Press, New York, Chapter 1, pp. 1–7 (1988).

Aronberg, "Techniques", Computed Body Tomography, Kee, et al., eds., Raven Press, New York, Chapter 2, pp. 9–36 (1988).

Miller, Ultrasonics (Sep. 1981), "Ultrasonic detection of resonant cavitation bubbles in a flow tube by their second-–harmonic emissions," pp. 217–224.

Dittrich, "Cardiac Muscle Ischemia and Infarction", The Second Annual International Symposium on Contrast Agents in Diagnostic Ultrasound, Atlantic City, NJ (May 7, 1996) (abstract).

Pantely, "Intravenous Contrast Echocardiography–Tissue Imaging & Quantification of Coronary Blood Flow", The Second Annual International Symposium on Contrast Agents in Diagnostic Ultrasound, Atlantic City, NJ (May 7, 1996) (abstract).

Schutt et al., "Osmotically Stabilized Microbuble Sonographic Contrast Agents", Acad. Radiol., vol. 3, Suppl. 2, pp. S188–S190 (Aug. 1996).

Frézard, et al., "Permeability and Stability in buffer and in human serum of fluorinated phospholipid–based liposomes", Biochimica et Biophysica Acta, 1192, pp. 61–70 (1994).

Frézard, et al., "Fluorinated Phospholipid–Based Vesicles as Potential Drug Cariers: Encapsulation/Sustaining of Drugs and Stability in Human Serum", Art, Cells, Blood Subs., and Immob. Biotech., 22(4), pp. 1403–1408 (1994).

Chang et al., "Semipermeable Aqueous Microcapsules", Canadian J. of Phys. And Pharm., 1966, 44, 115–128.

Chang, "Semipermeable Microcapsules", Science, 1964, 146, 524–525.

Deasy, Microencapsulation and Related Drug Processes, 1983, vol. 20, Chs. 9 and 10, 195–240 (Marcel Dekker, Inc., NY).

Yeung et al., "Preparation of Microencapsulated Liposomes", J. Microencapsulation, 1988, 5, 331–337.

Mattrey et al., Gas Emulsions as Ultrasound Contrast Agents; Preliminary Results in Rabbits and Dogs, Investigative Radiology, vol. 29, Jun. Supp. 2, pp. S139–S141, 1994.

Meltzer et al., Transmission of Ultrasonic Contrast Through the Lungs, Ultrasound in Med. & Biol., vol. 7, No. 4, 377–384, 1981.

PR Newswire, Apr. 1, 1986.

Swanson et al., Chapter 22, "Enhancement Agents for Ultrasound: Fundamentals", Pharmaceuticals In Medical Imaging, pp. 682–687 (1990).

Ophir et al., "Contrast Agents in Diagnostic Ultrasound", Ultrasound in Med. & Biol., vol. 15, No. 4, pp. 319–333 (1989).

Jacobs, "Intraocular gas measurement using A–scan ultrasound", Current Eye Research, vol. 5, No. 8, pp. 575–578 (1986).

Feinstein, Steven B., "Myocardial Perfusion Imaging: Contrast Echocardiography Today and Tomorrow," Journal of the American College of Cardiology, 8(1):251–253 (1986).

Keller et al., "The Behavior of Sonicated Albumin Microbubles Within the Microcirulation: A Basis for Their Use During Myocardial Contrast Echocardiography", Circulation Res., 65(2):458–465 (1989).

Lincoff et al, "Perfluoro–n–butane: A Gas for Maximum Duration Retinal Tamponade," Arch Ophthalmology, 101:460–462 (1983).

Remington's Pharmaceutical Sciences, John Hoover, managing ed., Mack Publishing Company, Easton, PA, pp. 295–298; 736; 1242–1244 (1975).

Handbook of Pharmaceutical Excipients, American Pharmaceutical Association, Washington, D.C. and The Pharmaceutical Society of Great Britain, London, England, pp. 181–183 (1986).

Barnhart et al., "Characteristics of Albunex™: Air–Filled Microspheres for Echocardiography Contrast Enhancement," Investigative Radiology, 25:S162–164, 1990.

Levene et al., "Characterization of Albunex™," J. Acoust. Soc. Am., 87(Suppl.1):569–70, 1990.

Miller et al., "Physiochemical Approaches to the Mode of Action of General Anesthetics," J. Amer. Soc. Anesthesiologists, 36(4):339–351 (1972).

"Properties and Applications of the 'Freon' Fluorocarbons" in DuPont Freon Technical Bulletin B–2 (E.I. DuPont de Nemours and Company, Wilmington, DE), pp. 1–11 (1964).

"'Freon' Fluorocarbons: Properties and Applications" in DuPont Technical Bulletin G–1 (E.I. DuPont de Nemours and Company, Wilmington, DE), pp. 1–10 (1987).

"Encyclopedia of Polymer Science and Engineering," John Wiley & Sons, New York, 1:164–169 (1985).

"Concise Encyclopedia of Polymer Science and Engineering," J. Kroschwitz, ed., John Wiley & Sons, New York, pp. 12–13 (1990).

Wheatley et al., "Contrast Agents for Diagnostic Ultrasound: Development and Evaluation of Polymer–Coated Microbubles," Biomaterials, 11:713–717 (1990).

Villanueva et al., "Characterization of Spatial Patters of Flow Within the Reperfused Myocardium by Myocardial Contrast Echocardiography: Implications in Determining Extent of Myocardial Salavage", *Circulation,* 1993, 88(6), 2596–2602.

Sekins et al., "Lung Cancer Hyperthermia via Ultrasound and PFC Liquids", *Published in Proceedings of 5th International Symposium on Hyperthermic Oncology, Kyoto, Japan,* Aug. 29–Sep. 3, 1998, 3 pages.

Pietersen, "A New Warning System for Fires of Electrical Origin", *CERN European Organization for Nuclear Research, Health and Safety Division,* Mar., 1977, 1–5.

Lincoff et al., "Intravitreal Expansion of Perfluorocarbon Bubbles", *Arch. Ophthalmol.,* 1980, 98, 1646.

Lincoff et al., "Intravitreal Longevity of Three Perfluorocarbon Gases", *Arch. Ophthalmol.,* 1980, 98, 1610–1611.

Lincoff et al., "The Perfluorocarbon Gases in the Treatment of Retinal Detachment", *Ophthalmology,* 1983, 90(5), 546–551.

Gardner et al., "A Survey of Intraocular Gas Use in North America", *Arch. Ophthalmol.,* 1988, 106, 1188–1189.

Unger et al., "Liposomal MR Contrast Agents", *J. Liposome Research,* 1994, 4(2), 811–834.

METHODS FOR DIAGNOSTIC IMAGING USING A RENAL CONTRAST AGENT AND A VASODILATOR

RELATED APPLICATION

This application is a continuation-in-part of copending application U.S. Ser. No. 08/712,173, filed Sep. 11, 1996, the disclosures of which are hereby incorporated herein by reference in their entirety.

FIELD OF THE INVENTION

The present invention relates to improved methods for diagnostic imaging. More particularly, the present invention relates to improved methods for diagnostic imaging which involve administering to a patient a renal vasodilator and a contrast agent.

BACKGROUND OF THE INVENTION

Ultrasound is a valuable diagnostic imaging technique for studying various areas of the body including, for example, the vasculature, such as tissue microvasculature. Ultrasound provides certain advantages over other diagnostic techniques. For example, diagnostic techniques involving nuclear medicine and X-rays generally result in exposure of the patient to ionizing electron radiation. Such radiation can cause damage to subcellular material, including deoxyribonucleic acid (DNA), ribonucleic acid (RNA) and proteins. Ultrasound does not involve such potentially damaging radiation. In addition, ultrasound is relatively inexpensive as compared to other diagnostic techniques, such as magnetic resonance imaging (MRI), which can require elaborate and expensive equipment.

Ultrasound involves the exposure of a patient to sound waves. Generally, the sound waves dissipate due to absorption by body tissue, penetrate through the tissue, or reflect off the tissue. The reflection of sound waves off tissue, generally referred to as backscatter or reflectivity, forms the basis for developing an ultrasound image. This is because sound waves reflect differentially from different body tissues. This differential reflection is due to various factors, including the constituents and the density of the particular tissue being observed. The differentially reflected waves are then detected, usually with a transducer which can detect sound waves having a frequency of from 1 megahertz (MHZ) to 10 MHZ. The detected waves are integrated, quantitated and converted into an image of the tissue being studied.

Imaging vascularized tissue generally involves an analysis of difference in the acoustic properties between blood and tissues. Therefore, attempts have been made to develop contrast agents which serve to increase the acoustic difference between blood and surrounding tissues. This may also permit the measurement of blood flow, thereby improving detection of diseases associated with changes in blood flow. Contrast agents can serve to improve the quality and usefulness of images which are obtained with ultrasound. Certain exemplary contrast agents include, for example, suspensions of solid particles and emulsified liquid droplets.

The reflection of sound from a liquid-gas interface is extremely efficient. Accordingly, certain bubbles, including certain gas-filled bubbles, can be highly useful as contrast agents. The term "bubbles", as used herein, refers to vesicles which are generally characterized by the presence of one or more membranes or walls surrounding an internal void that is filled with a gas or precursor thereto. Exemplary bubbles include, for example, vesicles which are surrounded by monolayers and/or bilayers to form, for example, unilamellar, oligolamellar and/or multilamellar vesicles, such as liposomes, micelles and the like. As discussed more fully hereinafter, the effectiveness of bubbles as contrast agents depends upon various factors, including, for example, the size and/or elasticity of the bubble.

The effectiveness of bubbles as contrast agents depends upon various factors, including, for example, the size of the bubble. As known to the skilled artisan, the signal which is in the range of diagnostic ultrasound frequencies and which can be reflected off of a bubble is a function of the radius ($r^6$) of the bubble (Rayleigh Scatterer). Thus, a bubble having a diameter of about 4 micrometer ($\mu$m) possesses about 64 times the scattering ability of a bubble having a diameter of about 2 $\mu$m. Thus, generally speaking, the larger the bubble, the greater the reflected signal.

However, bubble size is limited by the diameter of capillaries through which the bubbles must pass. Generally, contrast agents which comprise bubbles having a diameter of greater than about 10 $\mu$m can be dangerous since microvessels may be occluded. Accordingly, it is preferred that greater than about 90% of the bubbles in a contrast agent have a diameter of less than about 10 $\mu$m, with greater than about 95% being more preferred, and greater than about 98% being even more preferred. Mean bubble diameter is important also, and should be greater than about 1 $\mu$m, with greater than about 2 $\mu$m being preferred. The volume weighted mean diameter of the bubbles should be about 7 to about 20 $\mu$m.

The viability of currently available ultrasound contrast agents and methods involving their use is highly dependent on a variety of factors, including the particular region being imaged. In certain circumstances, diagnostic artifacts may render a diagnostic image substantially unusable.

In addition to ultrasound, computed tomography (CT) is a valuable diagnostic imaging technique for studying various areas of the body. In CT, the radiodensity (electron density) of matter is measured and is expressed in terms of Hounsefield Units (HU). Hounsefield Units, named after the inventor of the first CT scanner, are an indication of the relative absorption of CT X-rays by matter, the absorption being directly proportional to the electron density of that matter. Water, for example, has a value of 0 HU, air a value of −1000 HU, and dense cortical bone a value of 1000 HU. Because of the similarity in the densities of various tissues in the body, however, it has been necessary to develop contrast agents which can be used to change the relative densities of different tissues. This has resulted in an overall improvement in the diagnostic efficacy of CT.

In the search for contrast agents for CT, researchers have generally sought to develop agents that will increase electron density in certain areas of a region of the body (positive contrast agents). Barium and iodine compounds, for example, have been developed for this purpose. For the gastrointestinal tract, barium sulfate is used extensively to increase the radiodensity of the bowel lumen on CT scans. Iodinated water-soluble contrast media are also used to increase density within the gastrointestinal tract, but are not used as commonly as the barium compounds, primarily because the iodine preparations are more expensive than barium and are generally less effective in increasing radiodensity within this region of the body. The use of low density microspheres as CT contrast agents has also been reported. See, e.g., Unger, U.S. Pat. No. 5,205,290. As discussed above in connection with diagnostic methods for ultrasound, the viability of currently available CT contrast agents and methods involving their use for imaging the heart region is highly dependent on the flow of blood through the chambers of the heart relative to the flow of blood in the blood vessels of the heart tissue itself.

Magnetic resonance imaging (MRI) is another diagnostic imaging technique which may be used for producing cross-sectional images of the body in a variety of scanning planes such as, for example, axial, coronal, sagittal or orthogonal. MRI employs a magnetic field, radio frequency energy and magnetic field gradients to make images of the body. The contrast or signal intensity differences between tissues mainly reflect the T1 (longitudinal) and T2 (transverse) relaxation values and the proton density, which generally corresponds to the free water content, of the tissues. To change the signal intensity in a region of a patient by the use of a contrast medium, several possible approaches are available. For example, a contrast medium may be designed to change T1, T2, or the proton density.

Generally speaking, MRI requires the use of contrast agents. If MRI is performed without employing a contrast agent, differentiation of the tissue of interest from the surrounding tissues in the resulting image may be difficult. In the past, attention has focused primarily on paramagnetic contrast agents for MRI. Paramagnetic contrast agents involve materials which contain unpaired electrons. The unpaired electrons act as small magnets within the main magnetic field to increase the rate of longitudinal (T1) and transverse (T2) relaxation. Paramagnetic contrast agents typically comprise metal ions, for example, transition metal ions, which provide a source of unpaired electrons. However, these metal ions are also generally highly toxic. In an effort to decrease toxicity, the metal ions are typically chelated with ligands.

Metal oxides, most notably iron oxides, have also been employed as MRI contrast agents. While small particles of iron oxide, for example, particles having a diameter of less than about 20 nm, may have desirable paramagnetic relaxation properties, their predominant effect is through bulk susceptibility. Nitroxides are another class of MRI contrast agent which are also paramagnetic. These have relatively low relaxivity and are generally less effective than paramagnetic ions.

The existing MRI contrast agents suffer from a number of limitations. For example, increased image noise may be associated with certain contrast agents, including contrast agents involving chelated metals. This noise generally arises out of intrinsic peristaltic motions and motions from respiration or cardiovascular action. In addition, the signal intensity for contrast agents generally depends upon the concentration of the agent as well as the pulse sequence employed. Absorption of contrast agents can complicate interpretation of the images, particularly in the distal portion of the small intestine, unless sufficiently high concentrations of the paramagnetic species are used. See, e.g., Kornmesser et al., *Magnetic Resonance Imaging*, 6:124 (1988).

Other contrast agents may be less sensitive to variations in pulse sequence and may provide more consistent contrast. However, high concentrations of particulates, such as ferrites, can cause magnetic susceptibility artifacts which are particularly evident, for example, in the colon where the absorption of intestinal fluid occurs and the superparamagnetic material may be concentrated.

Toxicity is another problem which is generally associated with currently available contrast agents for MRI. For example, ferrites often cause symptoms of nausea after oral administration, as well as flatulence and a transient rise in serum iron. The gadolinium ion, which is complexed in Gd-DTPA, is highly toxic in free form. The various environments of the gastrointestinal tract, including increased acidity (lower pH) in the stomach and increased alkalinity (higher pH) in the intestines, may increase the likelihood of decoupling and separation of the free ion from the complex.

Blood flow may affect the quality of images obtained in MRI. For example, coronary vasodilators have been used in connection with thallium 201 ($^{201}$T1) in an effort to improve the visualization of viable myocardial tissue in nuclear medicine. Vasodilators can improve visualization by increasing blood flow to the myocardium which enables the $^{201}$T1 to be taken up more efficiently into viable myocardial cells. Coronary vasodilators have also been used in combination with Gd-DTPA to improve myocardial tissue imaging in MRI imaging. Although Gd-DTPA may be used as an indicator of blood flow, relaxation measurements (T1 and T2) may lack the necessary sensitivity to aid in the quantitative measurement of flow. In addition, MRI prior art contrast agents generally possess relatively low molecular weights which permits their diffusion through the vasculature. This may render the quantification of blood flow through the vasculature based on pharmacokinetics difficult.

Patients with renal vascular hypertension usually have a narrowing of one of the arteries to the kidneys, known as renal artery stenosis. Detection of renal vascular hypertension and distinguishing from the more common essential hypertension is critical, because renal artery hypertension does not respond to standard medical treatments administered for hypertension. Renal artery hypertension may be treated by angiotensin converting enzyme inhibitors or surgical management. Essential hypertension, in contrast, is usually treated with diuretics, beta or alpha blockers, afterload reducers, pre-load reducers and occasionally ganglionic blockers.

Diagnostic imaging may be used to detect the renal stenosis associated with renal hypertension. Imaging techniques used for imaging of the renal region include radionuclide scintigraphic methods and radionuclide nuclear medical methods. Captopril, an ACE inhibitor, has been used in combination with radiologic and radioscintigraphic procedures to detect stenosis in the renal artery. See, for example, Nally, et al., Sem. Nucl. Med. XXII; 85–97 (1992), Itoh, et al., Clin. Nucl. Med. 18; 463–471 (1993) and Dondi, et al., J. Nucl. Med. 33; 2040–2044 (1992). Nuclear medicine, however, suffers from poor spatial resolution, high expense, and as discussed below, the undesirable necessity of employing radioactive materials. Angiography is preferred to nuclear methods for detection of renal hypertension, but it also is expensive and invasive. Attempts to use ultrasound as a diagnostic tool for renal hypertension so far have generally provided poor results. See for example, Postma, et al., Br. J. Radiol. 65,857–860 (1992) and Kliewer, et al., Radiol. 189;779–787 (1993).

Accordingly, new and/or improved diagnostic imaging methods, particularly for imaging the renal region, are needed. New and/or better diagnostic imaging methods which permit the quantification of blood flow in the renal region are also needed. The present invention is directed to these, as well as other, important ends.

SUMMARY OF THE INVENTION

The present invention is directed, in part, to new and/or improved methods for diagnostic imaging. Specifically, in one embodiment, there is provided a method for providing an image of the renal region of a patient, comprising administering to the patient a vesicle composition comprising lipid, protein or polymer vesicles and a gas or gaseous precursor, in combination with a renal vasodilator. The patient is then scanned using diagnostic imaging to produce a visible image of the renal region of the patient.

Another embodiment of the invention also relates to a method for providing an image of the renal region of a patient. The method comprises administering to the patient a composition comprising a lipid, protein, or polymer and a gas or gaseous precursor, in combination with a renal vasodilator. The patient is then scanned using diagnostic imaging to obtain a visible image of the renal region.

A further embodiment of the invention provides a method for diagnosing the presence of diseased tissue in the renal region of a patient comprising (i) administering to the patient a vesicle composition comprising lipid, protein or polymer vesicles and a gas or gaseous precursor, in combination with a renal vasodilator, and (ii) scanning the patient using diagnostic imaging to obtain a visible image of any diseased tissue in the patient.

An even further embodiment of the invention provides a method for diagnosing the presence of diseased tissue in the renal region of a patient comprising (i) administering to the patient a composition comprising a lipid, protein, or polymer and a gas or gaseous precursor, in combination with a renal vasodilator, and (ii) scanning the patient using diagnostic imaging to obtain a visible image of any diseased tissue in the patient.

Still another embodiment provides a method for substantially eliminating diagnostic artifacts in a diagnostic image of the renal region of a patient, comprising administering to the patient, in combination with a contrast agent, an agent which induces vasodilation of a renal artery.

In a further embodiment of the invention there is provided a contrast agent for diagnostic imaging comprising a vesicle composition which comprises lipid, protein or polymer vesicles and a gas or gaseous precursor, in combination with a renal vasodilator.

In a still further embodiment of the invention there is provided a contrast agent for diagnostic imaging comprising a lipid, protein, or polymer and a gas or gaseous precursor, in combination with a renal vasodilator.

In an even further embodiment of the invention, there is provided a method for measuring blood flow in the renal region of a patient. The method comprises (i) administering to the patient a vesicle composition which comprises lipid, protein or polymer vesicles and a gas or gaseous precursor, (ii) scanning the patient with diagnostic imaging to obtain a visible image of the renal region, (iii) administering to the patient a renal vasodilator, (iv) continuing said scanning, and (v) determining the blood flow from a videodensity versus time relationship in the images obtained in steps (ii) through (iv).

In yet another embodiment of the invention, there is provided a method for measuring blood flow in the renal region of a patient, comprising (i) administering to the patient a composition comprising a lipid, protein or polymer and a gas or gaseous precursor, (ii) scanning the patient with diagnostic imaging to obtain a visible image of the renal region, (iii) administering to the patient a renal vasodilator, (iv) continuing said scanning, and (v) determining the blood flow from a videodensity versus time relationship in the images obtained in steps (ii) through (iv).

These and other aspects of the invention will become more apparent from the remaining discussions herein.

DETAILED DESCRIPTION OF THE INVENTION

Figure 1:
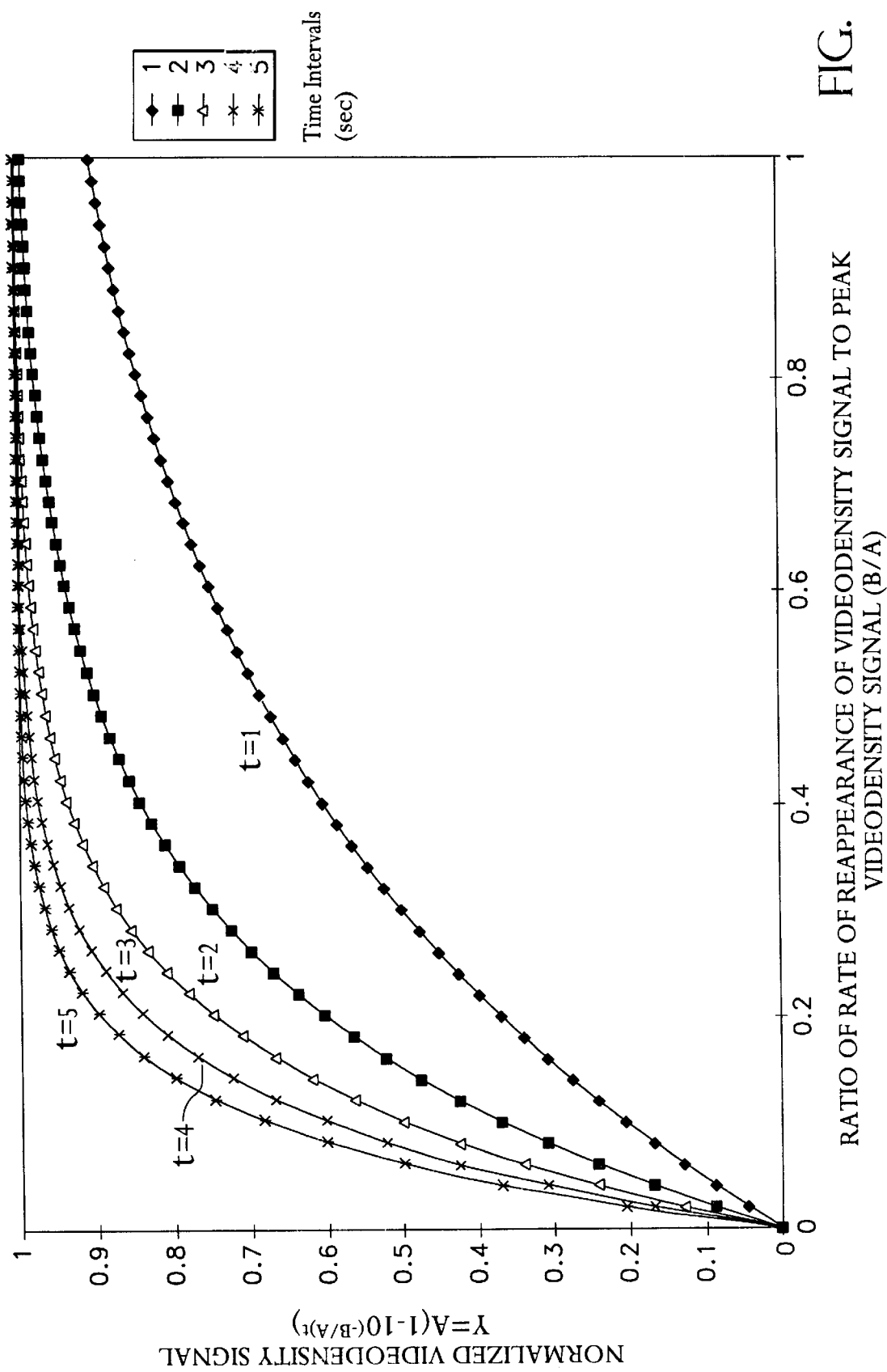
FIG. 1 is a plot of data obtained from pulse ultrasound imaging performed on a kidney, as described in Example 3. On the y axis are normalized videodensity values (y) against the ratio of reappearance of videodensity signal to peak videodensity signal. Each plot represents a different time interval (t) of 1 through 5 seconds between ultrasound pulses applied to rupture gas-filled vesicles which are used as an ultrasound contrast agent. The data illustrate the ability to quantitatively measure blood flow using pulsed ultrasound imaging and continuous administration of a renal vasodilator.

As employed above and throughout the disclosure, the following terms, unless otherwise indicated, shall be understood to have the following meanings.

"Lipid" refers to a naturally-occurring, synthetic, or semi-synthetic (also referred to as "modified natural") compound which is generally amphipathic. The lipids typically comprise a hydrophilic component and a hydrophobic component. Exemplary lipids include, for example, fatty acids, neutral fats, phosphatides, oils, glycolipids, surface-active agents (surfactants), aliphatic alcohols, waxes, terpenes and steroids.

"Polymer", or "polymeric", as used herein, refers to molecules formed from the chemical union of two or more repeating units. Accordingly, included within the term "polymer" may be, for example, dimers, trimers and oligomers. The polymer may be synthetic, naturally-occurring or semisynthetic. In preferred form, the term "polymer" refers to molecules which comprise 10 or more repeating units.

"Protein", as used herein, refers to molecules comprising, and preferably consisting essentially of, α-amino acids in peptide linkages. Included within the term "protein" are globular proteins, such as albumins, globulins and histones, and fibrous proteins such as collagens, elastins and keratins. Also included are "compound proteins", wherein a protein molecule is united with a nonprotein molecule, such as nucleoproteins, mucoproteins, lipoproteins, and metalloproteins.

"Lipid composition", "polymer composition", and "protein composition" refer to a composition which comprises a lipid, polymer, or protein compound, respectively, typically in an aqueous medium. Exemplary compositions include suspensions, emulsions and vesicle compositions. The compositions described herein may also comprise a bioactive agent.

"Vesicle" refers to an entity which is generally characterized by the presence of one or more walls or membranes which form one or more internal voids. Vesicles may be formulated, for example, from lipids, including the various lipids described herein, or polymeric materials, including the various polymeric materials listed herein, or proteins, including the various proteins listed herein. The lipids, polymers, and/or proteins may be natural, synthetic or semi-synthetic. Preferred vesicles are those which comprise walls or membranes formulated from lipids. The walls or membranes may be concentric or otherwise. In the preferred vesicles, the lipids may be in the form of a monolayer or bilayer, and the mono- or bilayer lipids may be used to form one or more mono- or bilayers. In the case of more than one mono- or bilayer, the mono- or bilayers may be concentric, if desired. Lipids may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). Similarly, the vesicles prepared from polymers or proteins may comprise one or more walls or membranes, concentric or otherwise. The walls or membranes of vesicles prepared from lipids, polymers, or proteins may be substantially solid (uniform), or they may be porous or semi-porous. The vesicles described herein include such entities commonly referred to as, for example, liposomes, micelles, bubbles, microbubbles, microspheres, lipid-, protein- and/or polymer-coated bubbles, microbubbles and/or microspheres, microballoons, microcapsules, aerogels, clathrate bound vesicles, hexagonal H II phase structures, and the like. The internal void of the vesicles may be filled with a liquid (including, for example, an aqueous liquid), a gas, a gaseous precursor, and/or a solid or solute material, including, for example, a vasodilator and/or bioactive agent, as desired. The vesicles may also comprise, if desired, a targeting ligand. The application of high energy ultrasound, radio frequency, optical energy, such as, for example, laser light, and/or heat, can be used, if desired, to rupture the vesicles in vivo and thereby promote release of the entrapped gas and/or gaseous precursor and bioactive agent. Thus, vesicular formulations permit the controlled release of a bioactive agent, such as a renal vasodilator, in vivo. The use of ultrasound energy in rupturing vesicles, thereby allowing release of a bioactive agent, is discussed in U.S. Pat. No. 5,558,092, the disclosures of which are hereby incorporated by reference in their entirety.

"Vesicle composition" refers to a composition, typically in an aqueous medium, which comprises vesicles.

"Vesicle formulation" refers to a vesicle composition which also comprises a bioactive agent. Suitable vesicles or vesicle species for use in vesicle formulations include, for example, gas filled vesicles and gaseous precursor filled vesicles.

"Liposome" refers to a generally spherical or spheroidal cluster or aggregate of amphipathic compounds, including lipid compounds, typically in the form of one or more concentric layers, for example, bilayers. They may also be referred to herein as lipid vesicles. The liposomes may be formulated, for example, from ionic lipids and/or non-ionic lipids. Liposomes which are formulated from non-ionic lipids may also be referred to as "niosomes."

"Micelle" refers to colloidal entities formulated from lipids. In certain preferred embodiments, the micelles comprise a monolayer or hexagonal H II phase configuration. In other preferred embodiments, the micelles may comprise a bilayer configuration.

"Aerogel" refers to generally spherical or spheroidal entities which are characterized by a plurality of small internal voids. The aerogels may be formulated from synthetic materials (for example, a foam prepared from baking resorcinol and formaldehyde), as well as natural materials, such as polysaccharides or proteins.

"Clathrate" refers to a solid, semi-porous or porous particle which may be associated with vesicles. In preferred form, the clathrates may form a cage-like structure containing cavities which comprise the vesicles. One or more vesicles may be bound to the clathrate. A stabilizing material may, if desired, be associated with the clathrate to promote the association of the vesicle with the clathrate. Suitable materials from which clathrates may be formulated include, for example, porous apatites, such as calcium hydroxyapatite, and precipitates of polymers and metal ions, such as alginic acid precipitates with calcium salts.

"Emulsion" refers to a mixture of two or more generally immiscible liquids and is generally in the form of a colloid. The mixture may be of lipids, which may be heterogeneously or homogeneously dispersed throughout the emulsion. Alternatively, the lipids may be aggregated in the form of, for example, clusters or layers, including mono- or bilayers.

"Suspension", or "dispersion", refers to a mixture, preferably finely divided, of two or more phases (solid, liquid, or gas), such as, for example, liquid in liquid, solid in liquid, gas in liquid, etc., which preferably can remain stable for extended periods of time.

"Hexagonal H II phase structure" refers to a generally tubular aggregation of lipids in liquid media, for example, aqueous media, in which the hydrophilic portion(s) of the lipids generally face inwardly in association with an aqueous liquid environment inside the tube. The hydrophobic portion(s) of the lipids generally radiate outwardly and the complex assumes the shape of a hexagonal tube. A plurality of tubes is generally packed together in the hexagonal phase structure.

The vesicles employed in the methods of the present invention preferably contain a gas or gaseous precursor. "Gas filled vesicle" refers to vesicles in which there is encapsulated a gas. "Gaseous precursor filled vesicle" refers to vesicles in which there is encapsulated a gaseous precursor. In certain preferred embodiments, the vesicles may be substantially (including completely) filled with the gas and/or gaseous precursor. The term "substantially", as used in reference to the gas and/or gaseous precursor filled vesicles, means that greater than about 50% of the internal void volume of the vesicle consists of a gas and/or gaseous precursor. Preferably, greater than about 60% of the internal void of the substantially filled vesicles consists of a gas and/or gaseous precursor, with greater than about 70% being more preferred. Even more preferably, greater than about 80% of the internal void of the substantially filled vesicles consists of a gas and/or gaseous precursor, with greater than about 90% being still more preferred. In particularly preferred embodiments, greater than about 95% of the internal void of the vesicles consists of a gas and/or gaseous precursor. If desired, the substantially filled vesicle may be completely filled (i.e. filled with about 100% gas and/or gaseous precursor). Although not considered a preferred embodiment of the present invention, the vesicles may also contain, if desired, no or substantially no, i.e., less than about 50%, gas and/or gaseous precursor.

The compositions and/or formulations of the invention may be administered to a patient. As used herein, "patient" refers to animals, including mammals, and preferably humans.

The phrases "internal region of a patient" and "region of interest" refer to the entire patient or to a particular area or portion of the patient. Internal regions of a patient and regions of interest may include, for example, areas being imaged with diagnostic imaging and/or areas being treated with a bioactive agent. The phrase "renal region of a patient" refers to the region of the patient defined by the kidney and the vasculature leading directly to and from the kidney, and includes the abdominal aorta. The phrase "vasculature," as used herein, denotes the blood vessels (including arteries, veins and the like) in the body or in an organ or part of the body. The phrase "circulatory system" refers to the cardiovascular region and the entire vasculature.

"Bioactive agent" refers to a substance which may be used in connection with an application that is therapeutic or diagnostic in nature, such as in methods for diagnosing the presence or absence of a disease in a patient and/or in methods for the treatment of disease in a patient. As used herein, "bioactive agent" refers also to substances which are capable of exerting a biological effect in vitro and/or in vivo. The bioactive agents may be neutral or positively or negatively charged. Examples of suitable bioactive agents include diagnostic and pharmaceutical agents (including vasodilators including renal vasodilators), synthetic or natural organic or inorganic molecules, including proteins, peptides, vitamins, steroids, steroid analogs, anti-tumor agents, hormones, anti-inflammatory agents, chemotherapeutic agents, and genetic material, including nucleosides, nucleotides and polynucleotides. Preferably, the bioactive agent comprises a pharmaceutical agent.

"Pharmaceutical agent" or "drug" refers to any therapeutic or prophylactic agent which may be used in the treatment (including the prevention, diagnosis, alleviation, or cure) of a malady, affliction, disease or injury in a patient. Therapeutically useful peptides, polypeptides and polynucleotides may be included within the meaning of the term pharmaceutical or drug. Preferred pharmaceuticals and/or drugs are renal vasodilators.

"Diagnostic agent" refers to any agent which may be used in connection with methods for imaging an internal region of a patient, including the renal region, and/or in methods for diagnosing the presence or absence of a disease in a patient, especially diseases of the heart including, for example, myocardial ischemia and myocardial infarction. Exemplary diagnostic agents include, for example, contrast agents for use in connection with ultrasound, magnetic resonance imaging or computed tomography of a patient including, for example, the lipid and/or vesicle compositions described herein.

"Genetic material" refers generally to nucleotides and polynucleotides, including deoxyribonucleic acid (DNA) and ribonucleic acid (RNA). The genetic material may be made by synthetic chemical methodology known to one of ordinary skill in the art, or by the use of recombinant technology, or by a combination of the two. The DNA and RNA may optionally comprise unnatural nucleotides and may be single or double stranded. "Genetic material" refers also to sense and anti-sense DNA and RNA, that is, a nucleotide sequence which is complementary to a specific sequence of nucleotides in DNA and/or RNA.

"Thickening agent" refers to any of a variety of generally hydrophilic materials which, when incorporated in the lipid and/or vesicle compositions described herein, may act as viscosity modifying agents, emulsifying and/or solubilizing agents, suspending agents, and tonicity raising agents. It is contemplated that the thickening agents may be capable of aiding in maintaining the stability of the compositions due to such properties.

"Dispersing agent" refers to a surface-active agent which, when added to a suspending medium of colloidal particles, including, for example, certain of the lipid and/or vesicle compositions described herein, may promote uniform separation of particles. In certain preferred embodiments, the dispersing agent may comprise a polymeric siloxane compound.

"Diagnostic artifact" refers generally to an imperfection, defect and/or flaw in a diagnostic image including, for example, ultrasound, computed tomography and magnetic resonance images, which may hamper and/or prevent visualization of a region of interest. Diagnostic artifacts may be manifested as undesired darkening and/or shadowing in the diagnostic image.

"Ultrasound artifact," "computed tomography artifact" and "MRI artifact" refer respectively to diagnostic artifacts associated with ultrasound, computed tomography and MRI.

"Echogenic vesicle" refers to a vesicle which may be capable of reflecting sound waves, including, for example, ultrasound waves. Echogenic vesicles may be particularly useful as contrast agents to alter, for example, the acoustic properties of an internal region of a patient, thereby resulting in improved contrast in diagnostic imaging techniques, such as ultrasound, computed tomography, and magnetic resonance imaging. In preferred form, the echogenic vesicles may comprise gas filled vesicles. Alternatively, the echogenic vesicles may comprise vesicles which contain no or substantially no gas or gaseous precursor and which, together with bubbles or globules of a gas or a gaseous precursor, are suspended in a liquid medium in divided form. In these latter embodiments, it is contemplated that echogenicity and/or an alteration in the acoustic properties of an internal region of a patient arises, at least in part, from the presence of the divided gas or gaseous precursor.

"Videodensity" or "Videodensitometry" refers to the backscatter intensity of an ultrasound image, and may be used to estimate the concentration of contrast agent, especially contrast agents based on vesicles, in a tissue, for example, renal tissue.

Generally speaking, videodensitometric analysis involves the use of a computer system which is capable of digitizing a full region of analog video data into a digital image having 512×512 pixels (picture elements). Each pixel may be represented by one of a total of about 256 gray levels which have numerical values of from 0 to about 255, 0 being white (no contrast) and 255 being black (complete contrast). These gray levels may also be referred to herein as videodensitometry units (VDUs).

"Brightness" refers to the level of contrast in a diagnostic image including, for example, ultrasound, computed tomography and magnetic resonance images, of a region of interest. Thus, in connection with diagnostic imaging of the renal region, the term "brightness" refers to the level of contrast of a diagnostic image of the renal region, including the kidney tissue and the vasculature associated therewith.

"Enhanced diagnostic image" refers to a diagnostic image which may be improved relative to diagnostic images obtained using one or more methods of the prior art and which may be obtained with the methods of the present invention. Enhanced diagnostic images may be manifested by an increase in brightness in the diagnostic image, substantial elimination of diagnostic artifacts in the diagnostic image, and/or the like. Thus, in connection with diagnostic imaging of the renal region, including the kidney tissue and the vasculature associated therewith, an enhanced diagnostic image may be manifested, for example, by increased brightness in the diagnostic image of the renal region and/or a substantial elimination in the occurrence of diagnostic artifacts in the diagnostic image of the renal region.

"Increased brightness" refers to an increase in the brightness of a diagnostic image which may be obtained with the methods of the present invention. Preferably, the increases in brightness provided by the methods of the present invention are at least discernible to the naked eye. With particular reference to the gray scale (about 0 to about 255 VDUs or gray levels) identified above, there is preferably provided with the methods of the present invention an increase in the level of brightness of at least about 10 VDUs (gray levels). More preferably, in accordance with the embodiment described herein, the methods of the present invention provide an increased brightness of greater than about 10 VDUs, for example, about 15, 20, 25, 30, 35, 40, 45, 50, 55, 60, 65, 70, 75, 80, 85, 90, 95 or 100 VDUs. In certain other embodiments, the present methods may provide an increased brightness of greater than about 100 VDUs, for example, about 105, 110, 115, 120, 125, 130, 135, 140, 145 or 150 VDUs. In still other embodiments, the methods of the present invention may provide an increased brightness of greater than about 150 VDUs, for example, about 155, 160, 165, 170, 175, 180, 185, 190, 195 or 200 VDUs. Yet in other embodiments, the present methods may provide an increased brightness of greater than about 200 VDUs, for example about 205, 210, 215, 220, 225, 230, 235, 240, 245, 250 or 255 VDUs.

"Substantial elimination" refers to the prevention or substantial prevention of the occurrence of diagnostic artifacts in a diagnostic image. The term "substantial prevention" means that at least about 50% of the artifacts may be eliminated by the methods of the present invention as compared to at least one prior art diagnostic method. Preferably, at least about 60% of the artifacts may be eliminated by the methods of the present invention as compared to at least one prior art diagnostic method, with the elimination of at least about 70% of the artifacts being more preferred. Even more preferably, at least about 80% of the artifacts may be eliminated by the methods of the present invention as compared to at least one prior art diagnostic method, with the elimination of at least about 90% of the artifacts being still more preferred. Yet more preferably, at least about 95% of the artifacts may be eliminated by the methods of the present invention as compared to at least one prior art diagnostic method, with the elimination of at least about 100% being still more preferred.

The terms "administered" and "administration" refer generally to the administration to a patient of a biocompatible material, including, for example, lipid, polymer or protein and/or vesicle compositions and/or formulations described herein.

"Biocompatible" refers to materials which are generally not injurious to biological functions and which will not result in any degree of unacceptable toxicity, including allergenic responses and disease states. The compositions and components thereof (such as lipids, protein, polymers, gases, gaseous precursors, vasodilators, etc.) employed in the present invention are typically biocompatible.

"In combination with" refers to the co-administration of a bioactive agent, such as a renal vasodilator, with a lipid, polymer or protein, and/or vesicle composition. The term "co-administration" means that the bioactive agent may be administered before, during, or after the administration of the composition. In embodiments in which the bioactive agent is included in the composition, as in a formulation, the bioactive agent may be combined with the vesicle composition in any of a variety of different ways. For example, in the case of vesicle compositions, the bioactive agent may be entrapped within the internal void of the vesicle. In addition, the bioactive agent may be integrated within the layer(s) or wall(s) of the vesicle, for example, by being interspersed among the lipids, proteins or polymers that comprise the vesicle layer(s) or wall(s). In the case of non-vesicular lipid, polymer and/or protein compositions, the bioactive agent may be entrapped between or among the lipid, polymer and/or protein components. It is also contemplated that the bioactive agent may be located on the surface of the vesicle or the non-vesicular lipid, polymer and/or protein. In this case, the bioactive agent may interact chemically with the inner or outer surface of the vesicle or the non-vesicular lipid, polymer and/or protein and remain substantially adhered thereto. Such interaction may take the form of, for example, electrostatic interactions, hydrogen bonding, vander Waal's forces, covalent bonding, or other interaction. Also, the bioactive agent may interact with the inner or outer surface of the vesicle or the non-vesicular lipid, polymer or protein in a limited manner. Such limited interaction would permit migration of the bioactive agent, for example, from the surface of a first vesicle to the surface of a second vesicle, or from the surface of a first non-vesicular lipid, polymer, or protein to the surface of a second non-vesicular lipid, polymer or protein.

"Renal vasodilator" refers to a bioactive agent which, when administered to a patient, causes or maintains dilation of the vasculature in the renal region. It is meant to include agents which act directly on the renal vasculature, as well as agents which act indirectly by activating or producing, or causing to be activated or produced, in vivo another agent which acts to cause or maintain dilation of the vasculature in the renal region.

"Ischemic" denotes a deficiency of blood due to functional constriction or actual obstruction of a blood vessel.

The present invention is directed, in part, to improved methods for diagnostic imaging, including, for example, improved methods for providing an image of an internal region of a patient, especially the renal region of a patient. The improved methods of the present invention may provide enhanced diagnostic images, as evidenced, for example, by increased brightness in the diagnostic image and/or a substantial elimination of diagnostic artifacts in the diagnostic image. Embodiments of the present invention involve the administration to the patient of a contrast agent in the form of a lipid, polymer or protein composition comprising a lipid, polymer or protein and a gas or gaseous precursor. Embodiments of the present invention also involve the administration to the patient of a contrast agent in the form of a vesicle composition comprising vesicles and a gas or gaseous precursor. The patient is scanned using diagnostic imaging, preferably ultrasound, to obtain a visible image of the region. An important feature of the methods of the present invention is that, in addition to a contrast agent, a renal vasodilator is administered to the patient. It is contemplated that the renal vasodilator provides unique advantages in connection with methods for diagnostic imaging, especially ultrasound, relative to methods for diagnostic imaging which have been available heretofore. In this connection, renal vasodilators are capable of dilating blood vessels in the renal region of a patient. This, in turn, may produce an alteration in the patient's blood flow in the renal region. It has been surprisingly and unexpectedly found that this alteration in the flow of blood in the renal region may produce profound changes in the quality of diagnostic images of the renal region. The present invention is directed, at least in part, to exploiting this surprising and unexpected discovery to provide improved methods for diagnostic imaging of the renal region. The present invention provides a simple and effective means for obtaining improved images of the renal region of a patient.

Diagnostic imaging, such as ultrasound imaging of the renal region, may involve the use of a contrast agent, for example, a contrast agent comprising gas filled vesicles, which is administered intravenously. After injection, the contrast agent may be carried in the bloodstream to the renal region. It is understood, of course, that in the normal course of the circulation of blood throughout the circulatory system, blood which contains the contrast agent will flow through the kidneys and associated vasculature. Energy, for example, ultrasound, may be applied, and a diagnostic image of the renal region may be generated. The basis for the ability to detect disease in the kidney using ultrasound is the difference in acoustic properties between blood and tissues. Contrast agents are expected to increase the acoustic difference between the blood and the surrounding tissues, thereby improving the detectability of blood flow and as a result, the detection of diseases involving changes in blood flow. In contrast with nuclear medicine, wherein radionuclides aid in assessing kidney function, ultrasound assesses blood flow and the structure of the renal vasculature.

It has been surprisingly and unexpectedly found that, in connection with methods for the diagnostic imaging of the renal region which involve the administration to a patient of a contrast agent comprising lipids, polymers, or proteins and a gas or gaseous precursor, and especially a contrast agent comprising lipid, polymer, or protein vesicles and a gas or gaseous precursor, the additional administration of a renal vasodilator can desirably enhance the resulting diagnostic image. While the inventors do not wish to be bound by any theory or theories of operation, it is believed that the enhanced diagnostic images may be due to an alteration in renal blood flow caused by the renal vasodilator. This alteration in the flow of blood may provide enhanced diagnostic images, which may be manifested, for example, by increased brightness and/or substantial elimination of diagnostic artifacts in the diagnostic image. It is believed that the administration to a patient of a renal vasodilator may increase blood flow and, therefore, the concentration of contrast agent in the renal tissue. This increase in contrast agent in the renal tissue may provide increased brightness in diagnostic images of the renal region and renal tissue, which may result in improved tissue visualization. It is believed also that the administration of a renal vasodilator may increase the flow of blood (and concentration of contrast agent) in the renal tissue relative to the flow of blood (and concentration of contrast agent) in the associated vasculature. This may result in a reduction or substantial elimination of diagnostic artifacts in images of the renal region.

The measurable physical manifestations of blood flow through the renal artery are affected by factors which dilate or constrict the artery. Furthermore, it is expected that branching of an artery into smaller arterioles, as occurs in some patients, results in a decreased arterial volume and an associated increase in blood pressure. It is believed that renal vasodilators reverse this effect, thereby increasing blood volume. When a renal artery is branched, one or more branches may be stenotic and a segment of a kidney may be ischemic. The methods of the present invention may be used in diagnosing such conditions.

Another effect of a renal vasodilator is to increase the differential blood flow between an ischemic kidney and a non-ischemic kidney. This in turn increases the difference in the videodensitometry between the ischemic kidney and the non-ischemic kidney in diagnostic imaging. As discussed below, the dosage level of renal vasodilator is determined by a number of factors including the patient's body weight, but is preferably a level sufficient to increase blood flow in a non-ischemic kidney.

In preferred embodiments of the present invention, a contrast agent is administered to a patient, ultrasound imaging of the renal region is performed, a renal vasodilator is administered, and ultrasound imaging is repeated. It is expected that a non-ischemic kidney will exhibit a more noticeable increased blood flow due to the renal vasodilator than will an ischemic kidney. In effect, the increased blood flow caused by the renal vasodilator enhances the difference in the videodensitometry between an ischemic kidney and a non-ischemic kidney. The effect of the contrast agent is thereby enhanced by the use of the renal vasodilator. The resulting renograms may be analyzed by comparing the intensities of the imaging signals of the kidneys and renal region before and after the administration of the renal vasodilator.

The degree of increase in renal blood flow which may be provided using the methods of the present invention may vary and depends, for example, on the particular lipid and/or vesicle composition administered to the patient, the particular renal vasodilator administered to the patient, the respective dosages of the lipid/vesicle composition and renal vasodilator administered to the patient, and the like. Generally speaking, any increase in blood flow which is obtained using the methods of the present invention may provide enhanced diagnostic images. In accordance with preferred embodiments of the present invention, enhanced diagnostic images may be obtained by increasing blood flow by greater than about 10%, for example, about 20, 30, 40 or 50%. Preferably, enhanced diagnostic images may be obtained by increasing blood flow by greater than about 50%, for example, about 60, 70, 80, 90 or 100%, with increased blood flow of greater than about 100%, for example, about 110, 120, 130, 140 or 150%, being more preferred. Even more preferably, enhanced diagnostic images may be obtained by increasing blood flow by greater than about 150%, for example, about 160, 170, 180 or 190%, with an increase of about 200% being still more preferred. In certain particularly preferred embodiments, enhanced diagnostic images may be obtained by increasing blood flow by greater than about 200%.

In accordance with the present invention, the foregoing alterations in the flow of blood may be achieved by the administration to the patient of a renal vasodilator. Thus, in preferred form, the methods of the present invention involve the administration to a patient of a contrast agent in combination with a renal vasodilator. Generally speaking, the renal vasodilator employed in the methods of the present invention may be administered before, during and/or after the administration of contrast agent. As would be apparent to one of ordinary skill in the art, once armed with the present disclosure, the order of administration of the contrast agent and renal vasodilator, as well as the manner in which they are administered may be varied, as desired, as a means of modulating the resulting diagnostic image. Thus, the present methods enable the skilled artisan to obtain the desired information about the patient, including, for example, the condition of the tissue being imaged, especially renal tissue, and the rate of blood flow in the renal region, which may provide information concerning the overall health and well-being of the patient. For example, it is contemplated that the present methods may initially involve a continuous administration or infusion of contrast agent to the patient. In this manner, there may be provided in the renal region of the patient a substantially constant flow or concentration of contrast agent. Administration of a renal vasodilator may provide an increased flow of blood in the renal region of the patient which, in turn, may provide increased brightness in the diagnostic image of the renal tissue.

In embodiments which employ a constant administration or infusion of contrast agent, the rate of response of the patient to the renal vasodilator may also provide information concerning the presence or absence of disease, including renal disease, in the patient. Specifically, the time required for the patient to respond to the renal vasodilator as evidenced, for example, by the rate of increase in renal blood flow, may provide information concerning the integrity of the patient's renal artery. Thus, a patient having substantially no renal artery stenosis may respond substantially rapidly to the renal vasodilator, as measured by an increase in the renal blood flow. Conversely, a patient having severe renal artery stenosis may respond to the renal vasodilator at a rate which is slower than the rate at which a patient having no stenosis responds.

In embodiments of the present invention, the contrast agents may comprise a lipid composition comprising a lipid and a gas or gaseous precursor. In connection with lipid compositions, and especially lipid compositions in the form of vesicle compositions, it may be advantageous to prepare the lipid compositions at a temperature below the gel to liquid crystalline phase transition temperature of the involved lipids. This phase transition temperature is the temperature at which a lipid bilayer will convert from a gel state to a liquid crystalline state. See, for example, Chapman et al., *J. Biol. Chem.* 1974 249, 2512–2521.

It is generally believed that vesicles which are prepared from lipids that possess higher gel state to liquid crystalline state phase transition temperatures tend to have enhanced impermeability at any given temperature. See Derek Marsh, *CRC Handbook of lipid Bilayers* (CRC Press, Boca Raton, Fla. 1990), at p. 139 for main chain melting transitions of saturated diacyl-sn-glycero-3-phosphocholines. The gel state to liquid crystalline state phase transition temperatures of various lipids will be readily apparent to those skilled in the art and are described, for example, in Gregoriadis, ed., *Liposome Technology*, Vol. 1, 1–18 (CRC Press, 1984). The following table lists some of the representative lipids and their phase transition temperatures.

TABLE 1

Saturated Diacyl-sn-Glycero-3-Phosphocholines:
Main Chain Melting Transition Temperatures

| Number of Carbons in Acyl Chains | Main Phase Transition Temperature (°C.) |
|---|---|
| 1,2-(12:0) | −1.0 |
| 1,2-(13:0) | 13.7 |
| 1,2-(14:0) | 23.5 |
| 1,2-(15:0) | 34.5 |
| 1,2-(16:0) | 41.4 |
| 1,2-(17:0) | 48.2 |
| 1,2-(18:0) | 55.1 |
| 1,2-(19:0) | 61.8 |
| 1,2-(20:0) | 64.5 |
| 1,2-(21:0) | 71.1 |
| 1,2-(22:0) | 74.0 |
| 1,2-(23:0) | 79.5 |
| 1,2-(24:0) | 80.1 |

See, for example, Derek Marsh, *CRC Handhook of lipid Bilayers*, p. 139 (CRC Press, Boca Raton, Fla. 1990).

It may be possible to enhance the stability of vesicles formulated from lipids by incorporating in the lipid compositions at least a minor amount, for example, about 1 to about 10 mole percent, based on the total amount of lipid employed, of a negatively charged lipid. Suitable negatively charged lipids include, for example, phosphatidylserine, phosphatidic acid, and fatty acids. Without intending to be bound by any theory or theories of operation, it is contemplated that such negatively charged lipids may provide added stability by counteracting the tendency of vesicles to rupture by fusing together. Thus, the negatively charged lipids may act to establish a uniform negatively charged layer on the outer surface of the vesicle, which will be repulsed by a similarly charged outer layer on other vesicles which may be proximate thereto. In this way, the vesicles may be less prone to come into touching proximity with each other, which may lead to a rupture of the membrane or skin of the respective vesicles and consolidation or fusion of the contacting vesicles into a single, larger vesicle. A continuation of this process of consolidation will, of course, lead to significant degradation of the vesicles.

The lipid materials used in certain of the compositions described herein, especially in connection with vesicle compositions based on lipids, are also preferably flexible. This means that, for example, in the case of vesicle compositions based on lipids, the vesicles can alter their shape, for example, to pass through an opening having a diameter that is smaller than the diameter of the vesicle.

A wide variety of lipids are believed to be suitable for incorporation in the lipid and/or vesicle compositions. With particular reference to vesicle compositions, for example, micelles and/or liposomes, any of the materials or combinations thereof which are known to those skilled in the art as suitable for their preparation may be used. The lipids used may be of natural, synthetic or semi-synthetic origin. As noted above, suitable lipids generally include, for example, fatty acids, neutral fats, phosphatides, glycolipids, aliphatic alcohols and waxes, terpenes and steroids.

Exemplary lipids which may be used to prepare lipid compositions include, for example, fatty acids; lysolipids; phosphocholines; phosphatidylcholine with both saturated and unsaturated lipids, including dioleoylphosphatidylcholine; dimyristoylphosphatidylcholine; dipentadecanoylphosphatidylcholine; dilauroylphosphatidylcholine; dipalmitoylphosphatidylcholine (DPPC); distearoylphosphatidylcholine (DSPC); and diarachidonylphosphatidylcholine (DAPC); phosphatidylethanolamines, such as dioleoylphosphatidylethanolamine, dipalmitoylphosphatidylethanol-amine (DPPE) and distearoylphosphatidylethanolamine (DSPE); phosphatidylserine; phosphatidylglycerols, including distearoylphosphatidylglycerol (DSPG); phosphatidylinositol; sphingolipids, such as sphingomyelin; glycolipids, such as ganglioside GM1 and GM2; glucolipids; sulfatides; glycosphingolipids; phosphatidic acids, such as dipalmitoylphosphatidic acid (DPPA) and distearoylphosphatidic acid (DSPA); palmitic acid; stearic acid; arachidonic acid; oleic acid; lipids bearing biocompatible polymers, such as chitin, hyaluronic acid, polyvinylpyrrolidone or polyethylene glycol (PEG), the latter being also referred to herein as "pegylated lipids", with preferred lipids bearing polymers including DPPE-PEG, which refers to the lipid DPPE having a PEG polymer attached thereto, including, for example, DPPE-PEG5000, which refers to DPPE having attached thereto a PEG polymer having a mean average molecular weight of about 5000; lipids bearing sulfonated mono-, di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes such as polyoxyethylene fatty acid esters, polyoxyethylene fatty alcohols, polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oil, polyoxyethylene-polyoxypropylene polymers and polyoxyethylene fatty acid stearates; sterol aliphatic acid esters, including cholesterol sulfate, cholesterol butyrate, cholesterol iso-butyrate, cholesterol palmitate, cholesterol stearate, lanosterol acetate, ergosterol palmitate and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate and ergosterol gluconate; esters of sugar acids and alcohols including lauryl glucuronide, stearoyl glucuronide, myristoyl glucuronide, lauryl gluconate, myristoyl gluconate and stearoyl gluconate; esters of sugars and aliphatic acids, including sucrose laurate, fructose laurate, sucrose palmitate, sucrose stearate, glucuronic acid, gluconic acid and polyuronic acid; saponins, including sarsasapogenin, smilagenin, hederagenin, oleanolic acid and digitoxigenin; glycerols, including glycerol dilaurate, glycerol trilaurate, glycerol dipalmitate, glycerol and glycerol esters, such as glycerol tripalmitate, glycerol distearate, glycerol tristearate, glycerol dimyristate and glycerol trimyristate; long chain alcohols, including n-decyl alcohol, lauryl alcohol, myristyl alcohol, cetyl alcohol and n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxyl-1-thio-β-D-galactopyranoside; 6-(5-cholesten-3β-yloxy)hexyl-6-amino-6-deoxyl-1-thio-α-D-mannopyranoside; 12-(((7'-diethylaminocoumarin-3-yl)carbonyl)-methylamino)-octadecanoic acid; N-[12-(((7'-diethylaminocoumarin-3-yl)carbonyl)-methylamino)-octadecanoyl]-2-aminopalmitic acid; cholesteryl)4'-trimethyl-ammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoyl-glycerophosphoethanolamine and palmitoylhomocysteine, and/or combinations thereof.

If desired, a cationic lipid may be used, such as, for example, N-[1-(2,3-dioleoyloxy)propyl]-N,N,N-trimethylammonium chloride (DOTMA), 1,2-dioleoyloxy-3-(trimethylammonio)propane (DOTAP); and 1,2-dioleoyl-3-(4'-trimethylammonio)-butanoyl-sn-glycerol (DOTB). If a cationic lipid is employed in the lipid compositions, the molar ratio of cationic lipid to non-cationic lipid may be, for example, from about 1:1000 to about 1:100. Preferably, the molar ratio of cationic lipid to non-cationic lipid may be from about 1:2 to about 1:10, with a ratio of from about 1:1 to about 1:2.5 being preferred. Even more preferably, the molar ratio of cationic lipid to non-cationic lipid may be about 1:1.

In the case of lipid compositions which contain both cationic and non-cationic lipids, a wide variety of lipids may be employed as the non-cationic lipid. Preferably, this non-cationic lipid comprises one or more of DPPC, DPPE and dioleoylphosphatidylethanolamine. In lieu of the cationic lipids listed above, lipids bearing cationic polymers, such as polylysine or polyarginine, as well as alkyl phosphonates, alkyl phosphinates and alkyl phosphites, may also be used in the lipid compositions.

In preferred embodiments, the lipid compositions comprise phospholipids, particularly one or more of DPPC, DPPE, DPPA, DSPC, DSPE, and DAPC (20 carbons), with DPPC, DPPE and/or DPPA being especially preferred.

Saturated and unsaturated fatty acids may also be employed in the lipid compositions described herein and may include molecules that preferably contain from about 12 carbons to about 22 carbons, in linear or branched form. Hydrocarbon groups consisting of isoprenoid units and/or prenyl groups can be used as well. Examples of saturated fatty acids that are suitable include, for example, lauric, myristic, palmitic and stearic acids. Suitable unsaturated fatty acids that may be used include, for example, lauroleic, physeteric, myristoleic, linoleic, linolenic, palmitoleic, petroselinic and oleic acids. Examples of branched fatty acids that may be used include, for example, isolauric, isomyristic, isopalmitic and isostearic acids.

The methods of the present invention may also involve compositions and vesicles formulated from proteins or derivatives thereof Vesicles which are formulated from proteins and which would be suitable for use in the methods of the present invention are described, for example, in Feinstein, U.S. Pat. Nos. 4,572,203, 4,718,433, and 4,774,958, and Cerny et al., U.S. Pat. No. 4,957,656, all of the disclosures of which are hereby incorporated by reference in their entirety. Other protein-based vesicles, in addition to those described in the aforementioned patents, would be apparent to one of ordinary skill in the art, once armed with the present disclosure.

In addition to lipid compositions and/or vesicles formulated from lipids and/or proteins, the methods of the present invention may also involve compositions and/or vesicles formulated from polymers which may be of natural, semi-synthetic (modified natural) or synthetic origin, with semi-synthetic and synthetic polymers being preferred. As used herein, the term polymer denotes a compound comprised of two or more repeating monomeric units, and preferably 10 or more repeating monomeric units. The phrase semi-synthetic polymer (or modified natural polymer), as employed herein, denotes a natural polymer that has been chemically modified in some fashion. Exemplary natural polymers suitable for use in the present invention include naturally occurring polysaccharides. Such polysaccharides include, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, polydextrose, pustulan, chitin, agarose, keratan, chondroitan, dermatan, hyaluronic acid, alginic acid, xanthan gum, starch and various other natural homopolymer or heteropolymers, such as those containing one or more of the following aldoses, ketoses, acids or amines:erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glucuronic acid, gluconic acid, glucaric acid, galacturonic acid, mannuronic acid, glucosamine, galactosamine, and neuraminic acid, and naturally occurring derivatives thereof Exemplary semi-synthetic polymers include carboxymethylcellulose, hydroxymethylcellulose, hydroxypropylmethyl-cellulose, methylcellulose, and methoxycellulose. Exemplary synthetic polymers suitable for use in the present invention include polyethylenes (such as, for example, polyethylene glycol, polyoxyethylene, and polyethylene terephthlate), polypropylenes (such as, for example, polypropylene glycol), polyurethanes (such as, for example, polyvinyl alcohol (PVA), polyvinylchloride and polyvinylpyrrolidone), polyamides including nylon, polystyrene, polylactic acids, fluorinated hydrocarbons, fluorinated carbons (such as, for example, polytetrafluoroethylene), and polymethylmethacrylate, and derivatives thereof Preferred are biocompatible synthetic polymers or copolymers prepared from monomers, such as acrylic acid, methacrylic acid, ethyleneimine, crotonic acid, acrylamide, ethyl acrylate, methyl methacrylate, 2-hydroxyethyl methacrylate (HEM), lactic acid, glycolic acid, ε-caprolactone, acrolein, cyanoacrylate, cyanomethacrylate, bisphenol A, epichlorhydrin, hydroxyalkyl-acrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-amimo-styrene, p-amino-benzylstyrene, sodium styrene sulfonate, sodium 2-sulfoxyethylmethacrylate, vinyl pyridine, aminoethyl methacrylates, 2-methacryloyloxytrimethylammonium chloride, and polyvinylidene, as well polyfunctional crosslinking monomers such as N,N'-methylenebisacrylamide, ethylene glycol dimethacrylates, 2,2'-(p-phenylenedioxy)-diethyl dimethacrylate, divinylbenzene, triallylamine and methylenebis-(4-phenyl-isocyanate), including combinations thereof. Preferable polymers include polyacrylic acid, polyethyleneimine, polymethacrylic acid, polymethylmethacrylate, polysiloxane, polydimethylsiloxane, polylactic acid, poly(ε-caprolactone), epoxy resin, poly(ethylene oxide), poly(ethylene glycol), and polyamide (nylon) polymers. Preferable copolymers include polyvinylidene-polyacrylonitrile, polyvinylidene-polyacrylonitrile-polymethyl-methacrylate, polystyrene-polyacrylonitrile and poly d,l lactide co-glycolide polymers. A preferred copolymer is polyvinylidene-polyacrylonitrile. Other suitable biocompatible monomers and polymers will be readily apparent to those skilled in the art, once armed with the present disclosure. Methods for the preparation of vesicles comprising polymers will be readily apparent to those skilled in the art, once armed with the present disclosure, when the present disclosure is coupled with information known in the art, such as that described and referred to in Unger, U.S. Pat. No. 5,205,290, the disclosures of which are hereby incorporated herein by reference in their entirety.

Vesicles derived from lipids, proteins, or polymers for use in the methods of the present invention are preferably low density. The term "low density" refers to vesicles which have an internal void (cavity) volume which is at least about 75% of the total volume of the vesicle. Preferably, the vesicles have a void volume of at least about 80%, more preferably at least about 85%, even more preferably at least about 90%, still more preferably at least about 95%, and yet more preferably about 100% of the total volume of the vesicles.

As noted above, the lipid, protein, and polymer compositions, and/or vesicles, employed in the present methods may also comprise a gas, such as an inert gas. The gas may provide the lipid, protein, or polymer compositions and/or vesicles with enhanced imaging capabilities, such as reflectivity or ultrasound, particularly in connection with vesicle compositions in which the gas is entrapped within the vesicles. This may increase the effectiveness of the vesicle compositions as contrast agents.

Preferred gases are gases which are inert and which are biocompatible, that is, gases which are not injurious to biological function. Preferred gases include those selected from the group consisting of air, noble gases, such as helium, rubidium hyperpolarized xenon, hyperpolarized argon, hyperpolarized helium, neon, argon, xenon, carbon dioxide, nitrogen, fluorine, oxygen, sulfur-based gases, such as sulfur hexafluoride and sulfur tetrafluoride, fluorinated gases, including, for example, partially fluorinated gases or completely fluorinated gases. Exemplary fluorinated gases include the fluorocarbon gases, such as the perfluorocarbon gases, and mixtures thereof. Paramagnetic gases, such as $^{17}O_2$, may also be used in the lipid and/or vesicle compositions.

In preferred embodiments, the gas utilized in the compositions described herein comprises a fluorinated gas. Such fluorinated gases include materials which contain at least one, or more than one, fluorine atom. Preferred are gases which contain more than one fluorine atom, with perfluorocarbons (that is, fully fluorinated fluorocarbons, wherein all hydrogen atoms in the corresponding hydrocarbon are replaced by fluorine atoms) being more preferred. Preferably, the perfluorocarbon gas is selected from the group consisting of perfluoromethane, perfluoroethane, perfluoropropane, perfluorobutane, perfluoropentane, perfluorohexane, perfluorocyclobutane and mixtures thereof. More preferably, the perfluorocarbon gas is perfluoropropane or perfluorobutane, with perfluoropropane being particularly preferred. Another preferable gas is sulfur hexafluoride. Yet another preferable gas is heptafluoropropane, including 1,1,1,2,3,3,3-heptafluoropropane and its isomer, 1,1,2,2,3,3,3-heptafluoropropane. It is contemplated that mixtures of different types of gases, such as mixtures of a perfluorocarbon gas and another type of gas, such as air, can also be used in the compositions employed in the methods of the present invention. Other gases, including the gases exemplified above, would be readily apparent to one skilled in the art based on the present disclosure.

In certain preferred embodiments, a gas, for example, air or a perfluorocarbon gas, is combined with a liquid perfluorocarbon, such as perfluoropentane, perfluorohexane, perfluoroheptane, perfluorooctylbromide (PFOB), perfluorodecalin, perfluorododecalin, perfluorooctyliodide, perfluorotripropylamine and perfluorotributylamine.

It may also be desirable to incorporate in the lipid and/or vesicle compositions a precursor to a gaseous substance. Such precursors include materials that are capable of being converted to a gas in vivo. Preferably, the gaseous precursor is biocompatible, and the gas produced in vivo is biocompatible also.

Among the gaseous precursors which are suitable for use in the lipid and/or vesicle compositions described herein are agents which are sensitive to pH. These agents include materials that are capable of evolving gas, for example, upon being exposed to a pH that is neutral or acidic. Examples of such pH sensitive agents include salts of an acid which is selected from the group consisting of inorganic acids, organic acids and mixtures thereof Carbonic acid ($H_2CO_3$) is an example of a suitable inorganic acid, and aminomalonic acid is an example of a suitable organic acid. Other acids, including inorganic and organic acids, would be readily apparent to one skilled in the art based on the present disclosure.

Gaseous precursors which are derived form salts are preferably selected from the group consisting of alkali metal salts, ammonium salts and mixtures thereof. More preferably, the salt is selected from the group consisting of carbonate, bicarbonate, sesquecarbonate, aminomalonate and mixtures thereof.

Examples of suitable gaseous precursor materials which are derived from salts include, for example, lithium carbonate, sodium carbonate, potassium carbonate, lithium bicarbonate, sodium bicarbonate, potassium bicarbonate, magnesium carbonate, calcium carbonate, magnesium bicarbonate, ammonium carbonate, ammonium bicarbonate, ammonium sesquecarbonate, sodium sesquecarbonate, sodium ammomalonate and ammonium aminomalonate. Aminomalonate is well known in the art, and its preparation is described, for example, in Thanassi, *Biochemistry*, Vol. 9, no. 3, pp. 525–532 (1970); Fitzpatrick et al., *Inorganic Chemistry*, Vol. 13, no. 3 pp. 568–574 (1974); and Stelmashok et al., *Koordinatsionnaya Khimiya*, Vol. 3, no. 4, pp. 524–527 (1977). The disclosures of these publications are hereby incorporated herein by reference, in their entirety.

In addition to, or instead of being sensitive to changes in pH, the gaseous precursor materials may also comprise compounds which are sensitive to changes in temperature. Exemplary of suitable gaseous precursors which are sensitive to changes in temperature are perfluorocarbons, hydrofluorocarbons, hydrocarbon ethers, hydrofluorocarbon ethers, and perfluorocarbon ethers. These latter gaseous precursors are exemplified, for example, by anesthetic and anesthetic-like gases including, for example, halothane, enflurane, isoflurane, desflurane and sevoflurane. As the artisan will appreciate, a particular perfluorocarbon may exist in the liquid state when the lipid and/or vesicle compositions are first made, and thus may be used as a gaseous precursor. Alternatively, the perfluorocarbon may exist in the gaseous state when the lipid and/or vesicle compositions are made, and thus may be used directly as a gas. Whether the perfluorocarbon is used as a liquid or a gas generally depends on its liquid/gas phase transition temperature, or boiling point. For example, a preferred perfluorocarbon, perfluoropentane, has a liquid/gas phase transition temperature (boiling point) of 29.5° C. This means that perfluoropentane is generally a liquid at room temperature (about 25° C.), but is converted to a gas within the human body, the normal temperature of which is about 37° C., this temperature being above the transition temperature of perfluoropentane. Thus, under normal circumstances, perfluoropentane is a gaseous precursor. As a further example, there are the homologs of perfluoropentane, namely perfluorobutane and perfluorohexane. The liquid/gas transition of perfluorobutane is 4° C. and that of perfluorohexane is 57° C. Thus, perfluorobutane may be useful as a gaseous precursor, although more likely as a gas, whereas perfluorohexane may be useful as a gaseous precursor because of its relatively high boiling point. As known to one of ordinary skill in the art, the effective boiling point of a substance may be related to the pressure to which that substance is exposed. This relationship is exemplified by the ideal gas law PV=nRT, where P is pressure, V is volume, n is moles of substance, R is the gas constant, and T is temperature. The ideal gas law indicates that as pressure increases, the effective boiling point increases also. Conversely, as pressure decreases, the effective boiling point decreases.

A wide variety of materials may be used as temperature-sensitive gaseous precursors in the compositions described herein. It is only required that the material be capable of undergoing a phase transition to the gas phase upon passing through the appropriate temperature. Suitable gaseous precursors include, for example, hexafluoroacetone, isopropyl acetylene, allene, tetrafluoroallene, boron trifluoride, 1,2-butadiene, 2,3-butadiene, 1,3-butadiene, 1,2,3-trichloro-2-fluoro-1,3-butadiene, 2-methyl-1,3-butadiene, hexafluoro-1,3-butadiene, butadiyne, 1-fluorobutane, 2-methylbutane, perfluorobutane, 1-butene, 2-butene, 2-methyl-1-butene, 3-methyl-1-butene, perfluoro-1-butene, perfluoro-2-butene, 4-phenyl-3-butene-2-one, 2-methyl-1-butene-3-yne, butyl nitrate, 1-butyne, 2-butyne, 2-chloro-1,1,1,4,4,4-hexafluorobutyne, 3-methyl-1-butyne, perfluoro-2-butyne, 2-bromobutyraldehyde, carbonyl sulfide, crotononitrile, cyclobutane, methylcyclobutane, octafluorocyclobutane, perfluorocyclobutene, 3-chlorocyclopentene, perfluorocyclopentane, octafluorocyclopentene, cyclopropane, perfluorocyclopropane, 1,2-dimethylcyclopropane, 1,1-dimethyl-cyclopropane, 1,2-dimethylcyclopropane, ethylcyclopropane, methylcyclopropane, diacetylene, 3-ethyl-3-methyl diaziridine, 1,1,1-trifluorodiazoethane, dimethyl amine, hexafluorodimethylamine, dimethylethylamine, bis (dimethylphosphine)amine, perfluorohexane, perfluoroheptane, perfluorooctane, 2,3-dimethyl-2-norbomane, perfluorodimethylamine, dimethyloxonium chloride, 1,3-dioxolane-2-one, 4-methyl-1,1,1,2-tetrafluoroethane, 1,1,1-trifluoroethane, 1,1,2,2-tetrafluoroethane, 1,1,2-trichloro-1,2,2-trifluoroethane, 1,1-dichloroethane, 1,1-dichloro-1,2,2,2-tetrafluoroethane, 1,2-difluoroethane, 1-chloro-1,1,2,2,2-pentafluoroethane, 2-chloro- 1,1-difluoroethane, 1,1-dichloro-2-fluoroethane, 1-chloro-1,1,2,2-tetrafluoroethane, 2-chloro-1,1-difluoroethane, chloroethane, chloropentafluoroethane, dichlorotrifluoroethane, fluoroethane, perfluoroethane, nitropentafluoroethane, nitrosopentafluoroethane, perfluoroethylamine, ethyl vinyl ether, 1,1-dichloroethane, 1,1-dichloro-1,2-difluoroethane, 1,2-difluoroethane, methane, trifluoromethanesulfonyl chloride, trifluoromethanesulfonyl fluoride, bromodifluoronitrosomethane, bromofluoromethane, bromochlorofluoromethane, bromotrifluoromethane, chlorodifluoronitromethane, chlorodinitromethane, chlorofluoromethane, chlorotrifluoromethane, chlorodifluoromethane, dibromodifluoromethane, dichlorodifluoromethane, dichlorofluoromethane, difluoromethane, difluorolodomethane, disilanomethane, fluoromethane, iodomethane, iodotrifluoromethane, nitrotrifluoromethane, nitrosotrifluoromethane, tetrafluoromethane, trichlorofluoromethane, trifluoromethane, 2-methylbutane, methyl ether, methyl isopropyl ether, methyllactate, methylnitrite, methylsulfide, methyl vinyl ether, neopentane, nitrous oxide, 1,2,3-nonadecanetricarboxylic acid 2-hydroxytrimethyl ester, 1-nonene-3-yne, 1,4-pentadiene, n-pentane, perfluoropentane, 4-amino-4-methylpentan-2-one, 1-pentene, 2-pentene (cis and trans), 3-bromopent-1-ene, perfluoropent-1-ene, tetrachlorophthalic acid, 2,3,6-trimethyl-piperidine, propane, 1,1,1,2,2,3-hexafluoropropane, 1,2-epoxypropane, 2,2-difluoropropane, 2-aminopropane, 2-chloropropane, heptafluoro-1-nitropropane, heptafluoro-1-nitrosopropane, perfluoropropane, propene, hexafluoropropane, 1,1,1,2,3,3-hexafluoro-2,3-dichloropropane, 1-chloropropane, chloropropane-(trans), 2-chloropropane, 3-fluoropropane, propyne, 3,3,3-trifluoropropyne, 3-fluorostyrene, sulfur (di)-decafluoride ($S_2F_{10}$), 2,4-diarninotoluene, trifluoroacetonitrile, trifluoromethyl peroxide, trifluoromethyl sulfide, tungsten hexafluoride, vinyl acetylene and vinyl ether.

Perfluorocarbons are both preferred gases and preferred gaseous precursors for use in connection with the compositions employed in the methods of the present invention. Included among such perfluorocarbons are saturated perfluorocarbons, unsaturated perfluorocarbons, and cyclic perfluorocarbons. The saturated perfluorocarbons, which are usually preferred, have the formula $C_nF_{2n+2}$, where n is from 1 to about 12, preferably about 2 to about 10, more preferably about 3 to about 8, and even more preferably about 3 to about 6. Suitable perfluorocarbons include, for example, perfluoromethane, perfluoroethane, perfluoropropane, perfluorobutane, perfluorocyclobutane, perfluoropentane, perfluorohexane, perfluoroheptane, perfluorooctane and perfluorononane. Preferably, the perfluorocarbon is selected from the group consisting of perfluoropropane, perfluorobutane, perfluorocyclobutane, perfluoropentane, perfluorohexane, perfluoroheptane and perfluorooctane, with perfluoropropane being particularly preferred. Cyclic perfluorocarbons, which have the formula $C_nF_{2n}$, where n is from 3 to 8, preferably 3 to 6, may also be preferred, and include, for example, hexafluorocyclopropane, octafluorocyclobutane, and decafluorocyclopentane. Generally speaking, perfluorocarbons containing about 4 carbons or less are gases at room temperature, whereas perfluorocarbons containing from about 5 to about 12 carbons are liquids at room temperature. In either case, both liquid and/or gaseous perfluorocarbons may be incorporated in the compositions of the present invention.

In addition to the perfluorocarbons, it may be desirable to utilize stable fluorocarbons which are not completely fluorinated. Such fluorocarbons include heptafluoropropane, for example, 1,1,1,2,3,3,3-heptafluoropropane and its isomer, 1,1,2,2,3,3,3-heptafluoropropane.

The gaseous precursor materials may be also photoactivated materials, such as diazonium ion and aminomalonate. Certain lipid and/or vesicle compositions, and particularly vesicle compositions, may be formulated so that gas can be formed at the target tissue or by the action of sound on the composition. Examples of gaseous precursors are described, for example, in U.S. Pat. Nos. 5,088,499 and 5,149,319, the disclosures of which are hereby incorporated herein by reference, in their entirety. Other gaseous precursors, in addition to those exemplified above, will be apparent to one skilled in the art based on the present disclosure.

The gaseous substances and/or gaseous precursors are preferably incorporated in the lipid and/or vesicle compositions irrespective of the physical nature of the composition. Thus, it is contemplated that the gaseous substances and/or precursors thereto may be incorporated, for example, in lipid compositions in which the lipids are aggregated randomly, as well as in vesicle compositions, including vesicle compositions which are formulated from lipids, such as micelles and liposomes. Incorporation of the gaseous substances and/or precursors thereto in the lipid and/or vesicle compositions may be achieved by using any of a number of methods. For example, in the case of vesicles based on lipids, the formation of gas filled vesicles can be achieved by shaking or otherwise agitating an aqueous mixture which comprises a gas or gaseous precursor and one or more lipids. This promotes the formation of stabilized vesicles within which the gas or gaseous precursor is encapsulated.

In addition, a gas may be bubbled directly into an aqueous mixture of lipid and/or vesicle-forming compounds. Alternatively, a gas instillation method can be used as disclosed, for example, in U.S. Pat. Nos. 5,352,435 and 5,228,446, the disclosures of which are hereby incorporated herein by reference, in their entirety. Suitable methods for incorporating the gas or gaseous precursor in cationic lipid compositions are disclosed also in U.S. Pat. No. 4,865,836, the disclosures of which are hereby incorporated herein by reference in their entirety. Other methods would be apparent to one skilled in the art based on the present disclosure. Preferably, the gas may be instilled in the lipid and/or vesicle compositions after or during the addition of the stabilizing material and/or during formation of vesicles.

In preferred embodiments, the gaseous substances and/or gaseous precursor materials are incorporated in vesicle compositions, with micelles and liposomes being preferred. As discussed in detail below, vesicles in which a gas or gaseous precursor or both are encapsulated are advantageous in that they provide improved reflectivity in vivo.

As discussed more fully hereinafter, it is preferred that the lipid compositions, and especially the vesicle compositions, be formulated from lipids and optional stabilizing compounds to promote the formation of stable vesicles. In addition, it is also preferred that the lipid and/or vesicle compositions comprise a highly stable gas as well. The phrase "highly stable gas" refers to a gas which has limited solubility and diffusability in aqueous media. Exemplary highly stable gases include perfluorocarbons since they are generally less diffusible and relatively insoluble in aqueous media. Accordingly, their use may promote the formation of highly stable vesicles.

In certain embodiments, it may be desirable to use a fluorinated compound, especially a perfluorocarbon compound, which may be in the liquid state at the temperature of use of the lipid and/or vesicle compositions, including, for example, the in vivo temperature of the human body, to assist or enhance the stability of the lipid and/or vesicle compositions, and especially, the gas filled vesicles. Suitable fluorinated compounds include, for example, fluorinated surfactants, such as fluorinated surfactants which are commercially available as ZONYL® surfactants (the DuPont Company, Wilmington, DE), as well as liquid perfluorocarbons, such as for example, perfluorooctylbromide (PFOB), perfluorodecalin, perfluorododecalin, perfluorooctyliodide, perfluorotripropylamine, and perfluorotributylamine. In general, perfluorocarbons comprising about six or more carbon atoms will be liquids at normal human body temperature. Among these perfluorocarbons, perfluorooctylbromide and perfluorohexane, which are liquids at room temperature, are preferred. The gas which is present may be, for example, nitrogen or perfluoropropane, or may be derived from a gaseous precursor, which may also be a perfluorocarbon, for example, perfluoropentane. In the latter case, the lipid and/or vesicle compositions may be prepared from a mixture of perfluorocarbons, which for the examples given, would be perfluoropropane (gas) or perfluoropentane (gaseous precursor) and perfluorooctylbromide (liquid). Although not intending to be bound by any theory or theories of operation, it is believed that, in the case of vesicle compositions, the liquid fluorinated compound may be situated at the interface between the gas and the membrane or wall surface of the vesicle. There may be thus formed a further stabilizing layer of liquid fluorinated compound on the internal surface of the stabilizing compound, for example, a biocompatible lipid used to form the vesicle, and this perfluorocarbon layer may also prevent the gas from diffusing through the vesicle membrane. A gaseous precursor, within the context of the present invention, is a liquid at the temperature of manufacture and/or storage, but becomes a gas at least at or during the time of use.

Thus, it has been discovered that a liquid fluorinated compound, such as a perfluorocarbon, when combined with a gas or gaseous precursor ordinarily used to make the lipid and/or vesicle compositions described herein, may confer an added degree of stability not otherwise obtainable with the gas or gaseous precursor alone. Thus, it is within the scope of the present invention to utilize a gas or gaseous precursor, such as a perfluorocarbon gaseous precursor, for example, perfluoropentane, together with a perfluorocarbon which remains liquid after administration to a patient, that is, whose liquid to gas phase transition temperature is above the body temperature of the patient, for example, perfluorooctylbromide. Perfluorinated surfactants, such as ZONYL® fluorinated surfactants, may be used to stabilize the lipid and/or vesicle compositions, and to act, for example, as a coating for vesicles. Preferred perfluorinated surfactants are the partially fluorinated phosphocholine surfactants. In these preferred fluorinated surfactants, the dual alkyl compounds may be fluorinated at the terminal alkyl chains and the proximal carbons may be hydrogenated. These fluorinated phosphocholine surfactants may be used for making the targeted lipid and/or vesicle compositions employed in the methods of the present invention.

In connection with embodiments involving vesicle compositions, the size of the vesicles can be adjusted for the particular intended end use including, for example, diagnostic and/or therapeutic use. The size of the vesicles may preferably range from about 30 nanometers (nm) to about 100 micrometers ($\mu$m) in diameter, and all combinations and subcombinations of ranges therein. More preferably, the vesicles have diameters of from about 100 nm to about 10 $\mu$m, with diameters of from about 200 nm to about 7 $\mu$m being even more preferred. In connection with particular uses, for example, intravascular use, including magnetic resonance imaging of the vasculature, it may be preferred that the vesicles be no larger that about 30 $\mu$m in diameter, with smaller vesicles being preferred, for example, vesicles of no larger than about 12 $\mu$m in diameter. In certain preferred embodiments, the diameter of the vesicles may be about 7 $\mu$m or less, with vesicles having a mean diameter of about 5 $\mu$m or less being more preferred, and vesicles having a mean diameter of about 3 $\mu$m or less being even more preferred. It is contemplated that these smaller vesicles may perfuse small vascular channels, such as the microvasculature, while at the same time providing enough space or room within the vascular channel to permit red blood cells to slide past the vesicles. It is contemplated also that these smaller vesicles may be capable of traveling throughout the vasculature at about the same rate of flow as the blood and thus do not impede or substantially impede normal blood flow.

The size of the gas filled vesicles can be adjusted, if desired, by a variety of procedures including, for example, shaking, microemulsification, vortexing, extrusion, filtration, sonication, homogenization, repeated freezing and thawing cycles, extrusion under pressure through pores of defined size, and similar methods.

As noted above, compositions employed herein may also include, with respect to their preparation, formation and use, gaseous precursors that can be activated to change from a liquid or solid state into a gas by temperature, pH, light, and energy (such as ultrasound). The gaseous precursors may be made into gas by storing the precursors at reduced pressure. For example, a vial stored under reduced pressure may create a headspace of perfluoropentane or perfluorohexane gas, useful for creating a preformed gas prior to injection. Preferably, the gaseous precursors may be activated by temperature. Set forth below is a table listing a series of gaseous precursors which undergo phase transitions from liquid to gaseous states at relatively close to normal body temperature (37° C.) or below, and the size of the emulsified droplets that would be required to form a vesicle of a maximum size of 10 $\mu$m.

TABLE 2

Physical Characteristics of Gaseous Precursors and Diameter of Emulsified Droplet to Form a 10 $\mu$m Vesicle*

| Compound | Molecular Weight | Boiling Point (°C.) | Density | Diameter ($\mu$m) of emulsified droplet to make 10 micron vesicle |
|---|---|---|---|---|
| perfluoro pentane | 288.04 | 29.5 | 1.7326 | 2.9 |
| 1-fluorobutane | 76.11 | 32.5 | 0.67789 | 1.2 |
| 2-methyl butane (isopentane) | 72.15 | 27.8 | 0.6201 | 2.6 |
| 2-methyl 1-butene | 70.13 | 31.2 | 0.6504 | 2.5 |
| 2-methyl-2-butene | 70.13 | 38.6 | 0.6623 | 2.5 |
| 1-butene-3-yne-2-methyl | 66.10 | 34.0 | 0.6801 | 2.4 |
| 3-methyl-1-butyne | 68.12 | 29.5 | 0.6660 | 2.5 |
| octafluoro cyclobutane | 200.04 | −5.8 | 1.48 | 2.8 |
| decafluoro butane | 238.04 | −2 | 1.517 | 3.0 |
| hexafluoro ethane | 138.01 | −78.1 | 1.607 | 2.7 |

*Source: Chemical Rubber Company Handbook of Chemistry and Physics, Robert C. Weast and David R. Lide, eds., CRC Press, Inc. Boca Raton, Florida (1989–1990).

The perfluorocarbons, as already indicated, are preferred for use as the gas or gaseous precursors, as well as additional stabilizing components.

As noted above, it is preferred to optimize the utility of the lipid and/or vesicle compositions, especially vesicle compositions formulated from lipids, by using gases of limited solubility. The phrase "limited solubility" refers to the ability of the gas to diffuse out of the vesicles by virtue of its solubility in the surrounding aqueous medium. A greater solubility in the aqueous medium imposes a gradient with the gas in the vesicle such that the gas may have a tendency to diffuse out of the vesicle. A lesser solubility in the aqueous milieu, may, on the other hand, decrease or eliminate the gradient between the vesicle and the interface such that diffusion of the gas out of the vesicle may be impeded. Preferably, the gas entrapped in the vesicle has a solubility less than that of oxygen, that is, about 1 part gas in about 32 parts water. See *Matheson Gas Data Book*, 1966, Matheson Company Inc. More preferably, the gas entrapped in the vesicle possesses a solubility in water less than that of air; and even more preferably, the gas entrapped in the vesicle possesses a solubility in water less than that of nitrogen.

It may be desirable, in certain embodiments, to formulate vesicles from substantially impermeable polymeric materials. In these embodiments, it is generally unnecessary to employ a gas which is highly insoluble also. For example, stable vesicle compositions which comprise substantially impermeable polymeric materials may be formulated with gases having higher solubilities, for example, air or nitrogen.

In addition to, or instead of, the lipid and/or polymeric compounds discussed above, the compositions described herein may comprise one or more stabilizing materials. Exemplary of such stabilizing materials are, for example, biocompatible polymers. The stabilizing materials may be employed to desirably assist in the formation of vesicles and/or to assure substantial encapsulation of the gases or gaseous precursors. Even for relatively insoluble, non-diffusible gases, such as perfluoropropane or sulfur hexafluoride, improved vesicle compositions may be obtained when one or more stabilizing materials are utilized in the formation of the gas and gaseous precursor filled vesicles. These compounds may help improve the stability and the integrity of the vesicles with regard to their size, shape and/or other attributes.

The terms "stable" or "stabilized", as used herein, means that the vesicles may be substantially resistant to degradation, including, for example, loss of vesicle structure or encapsulated gas or gaseous precursor, for a useful period of time. Typically, the vesicles employed in the present invention have a desirable shelf life, often retaining at least about 90% by volume of its original structure for a period of at least about two to three weeks under normal ambient conditions. In preferred form, the vesicles are desirably stable for a period of time of at least about 1 month, more preferably at least about 2 months, even more preferably at least about 6 months, still more preferably about eighteen months, and yet more preferably up to about 3 years. The vesicles described herein, including gas and gaseous precursor filled vesicles, may also be stable even under adverse conditions, such as temperatures and pressures which are above or below those experienced under normal ambient conditions.

The stability of the vesicles described herein may be attributable, at least in part, to the materials from which the vesicles are made, including, for example, the lipids, proteins, and/or polymers described above, and it is often not necessary to employ additional stabilizing materials, although it is optional and may be preferred to do so. Such additional stabilizing materials and their characteristics are described more fully hereinafter.

The materials from which the vesicles are constructed are preferably biocompatible lipid, protein, and/or polymer materials, and of these, the biocompatible lipids are preferred. In addition, because of the ease of formulation, including the capability of preparing vesicles immediately prior to administration, these vesicles may be conveniently made on site.

Particularly preferred embodiments of the present invention involve vesicles which comprise three components: (1) a neutral lipid, for example, a nonionic or zwitterionic lipid, (2) a negatively charged lipid, and (3) a lipid bearing a stabilizing material, for example, a hydrophilic polymer. Preferably, the amount of the negatively charged lipid will be greater than about 1 mole percent of the total lipid present, and the amount of lipid bearing a hydrophilic polymer will be greater than about 1 mole percent of the total lipid present. Exemplary and preferred negatively charged lipids include phosphatidic acids. The lipid bearing a hydrophilic polymer will desirably be a lipid covalently linked to the polymer, and the polymer will preferably have a weight average molecular weight of from about 400 to about 100,000. Suitable hydrophilic polymers are preferably selected from the group consisting of polyethylene glycol (PEG), polypropylene glycol, polyvinyl alcohol, and polyvinylpyrrolidone and copolymers thereof, with PEG polymers being preferred. Preferably, the PEG polymer has a molecular weight of from about 1000 to about 7500, with molecular weights of from about 2000 to about 5000 being more preferred. The PEG or other polymer may be bound to the lipid, for example, DPPE, through a covalent bond, such as an amide, carbamate or amine linkage. In addition, the PEG or other polymer may be linked to a targeting ligand, or other phospholipids, with a covalent bond including, for example, amide, ester, ether, thioester, thioamide or disulfide bonds. Where the hydrophilic polymer is PEG, a lipid bearing such a polymer will be said to be "pegylated." In preferred form, the lipid bearing a hydrophilic polymer may be DPPE-PEG, including, for example, DPPE-PEG5000, which refers to DPPE having a polyethylene glycol polymer of a mean weight average molecular weight of about 5000 attached thereto (DPPE-PEG5000). Another suitable pegylated lipid is distearoylphosphatidylethanolamine-polyethylene glycol 5000 (DSPE-PEG5000).

In certain preferred embodiments of the present invention, the lipid compositions may include about 77.5 mole % DPPC, 12.5 mole % of DPPA, and 10 mole % of DPPE-PEG5000. Also preferred are compositions which comprise about 80 to about 90 mole % DPPC, about 5 to about 15 mole % DPPA and about 5 to about 15 mole % DPPE-PEG5000. Especially preferred are compositions which comprise DPPC, DPPA and DPPE-PEG5000 in a mole % ratio of 82:10:8, respectively. DPPC is substantially neutral, since the phosphatidyl portion is negatively charged and the choline portion is positively charged. Consequently, DPPA, which is negatively charged, may be added to enhance stabilization in accordance with the mechanism described above. DPPE-PEG provides a pegylated material bound to the lipid membrane or skin of the vesicle by the DPPE moiety, with the PEG moiety free to surround the vesicle membrane or skin, and thereby form a physical barrier to various enzymatic and other endogenous agents in the body whose function is to degrade such foreign materials. The DPPE-PEG may provide more vesicles of a smaller size which are safe and stable to pressure when combined with other lipids, such as DPPC and DPPA, in the given ratios. It is also theorized that the pegylated material, because of its structural similarity to water, may be able to defeat the action of the macrophages of the human immune system, which would otherwise tend to surround and remove the foreign object. The result is an increase in the time during which the stabilized vesicles may function as diagnostic imaging contrast media.

The vesicle compositions may be prepared from other materials, in addition to the materials described above, provided that the vesicles so prepared meet the stability and other criteria set forth herein. These materials may be basic and fundamental, and form the primary basis for creating or establishing the stabilized gas and gaseous precursor filled vesicles. On the other hand, they may be auxiliary, and act as subsidiary or supplementary agents which can enhance the functioning of the basic stabilizing material or materials, or contribute some desired property in addition to that afforded by the basic stabilizing material.

However, it is not always possible to determine whether a given material is a basic or an auxiliary agent, since the functioning of the material in question is determined empirically, for example, by the results produced with respect to producing stabilized vesicles. As examples of how these basic and auxiliary materials may function, it has been observed that the simple combination of a biocompatible lipid and water or saline when shaken will often give a cloudy solution subsequent to autoclaving for sterilization. Such a cloudy solution may function as a contrast agent, but is aesthetically objectionable and may imply instability in the form of undissolved or undispersed lipid particles. Cloudy solutions may be also undesirable where the undissolved particulate matter has a diameter of greater than about 7 $\mu$m, and especially greater than about 10 $\mu$m. Manufacturing steps, such as sterile filtration, may also be problematic with solutions which contain undissolved particulate matter. Thus, propylene glycol may be added to remove this cloudiness by facilitating dispersion or dissolution of the lipid particles. The propylene glycol may also function as a wetting agent which can improve vesicle formation and stabilization by increasing the surface tension on the vesicle membrane or skin. It is possible that the propylene glycol can also function as an additional layer that may coat the membrane or skin of the vesicle, thus providing additional stabilization. As examples of such further basic or auxiliary stabilizing materials, there are conventional surfactants which may be used; see D'Arrigo U.S. Pat. Nos. 4,684,479 and 5,215,680.

Additional auxiliary and basic stabilizing materials include such agents as peanut oil, canola oil, olive oil, safflower oil, corn oil, or any other oil commonly known to be ingestible which is suitable for use as a stabilizing compound in accordance with the teachings herein. Various auxiliary and basic stabilizing materials are disclosed, for example, in U.S. application Ser. No. 08/444,574, filed May 19, 1995, the disclosures of which are incorporated herein by reference, in their entirety.

In addition, compounds used to make mixed micelle systems may be suitable for use as basic or auxiliary stabilizing materials, and these include, for example, lauryltrimethylarmronium bromide (dodecyl-), cetyltrimethylammonium bromide (hexadecyl-), myristyltrimethylammonium bromide (tetradecyl-), alkyldimethylbenzylammonium chloride (where alkyl is $C_{12}$, $C_{14}$ or $C_{16}$,), benzyldimethyldodecylammonium bromide/chloride, benzyldimethyl hexadecylammonium bromide/chloride, benzyldimethyl tetradecylammonium bromide/chloride, cetyldimethylethylammonium bromide/chloride, or cetylpyridinium bromide/chloride.

It has also been found that the gas and gaseous precursor filled vesicles used in the present invention may be controlled according to size, solubility and heat stability by choosing from among the various additional or auxiliary stabilizing materials described herein. These materials can affect these parameters of the vesicles, especially vesicles formulated from lipids, not only by their physical interaction with the membranes, but also by their ability to modify the viscosity and surface tension of the surface of the gas and gaseous precursor filled vesicle. Accordingly, the gas and gaseous precursor filled vesicles used in the present invention may be favorably modified and further stabilized, for example, by the addition of one or more of a wide variety of (a) viscosity modifiers, including, for example, carbohydrates and their phosphorylated and sulfonated derivatives; polyethers, preferably with molecular weight ranges between 400 and 100,000; and di- and trihydroxy alkanes and their polymers, preferably with molecular weight ranges between 200 and 50,000; (b) emulsifying and/or solubilizing agents including, for example, acacia, cholesterol, diethanolamine, glyceryl monostearate, lanolin alcohols, lecithin, mono- and di-glycerides, mono-ethanolamine, oleic acid, oleyl alcohol, poloxamer, for example, poloxamer 188, poloxamer 184, and poloxamer 181, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, steanic acid, trolamine, and emulsifying wax; (c) suspending and/or viscosity-increasing agents, including, for example, acacia, agar, alginic acid, aluminum mono-stearate, bentonite, magma, carbomer 934P, carboxymethylcellulose, calcium and sodium and sodium 12, carrageenan, cellulose, dextran, gelatin, guar gum, locust bean gum, veegum, hydroxyethyl cellulose, hydroxypropyl methylcellulose, magnesium-aluminum-silicate, Zeolites®, methylcellulose, pectin, polyethylene oxide, povidone, propylene glycol alginate, silicon dioxide, sodium alginate, tragacanth, xanthan gum, α-d-gluconolactone, glycerol and mannitol; (d) synthetic suspending agents, such as polyethylene glycol (PEG), polyvinylpyrrolidone (PVP), polyvinyl alcohol (PVA), polypropylene glycol (PPG), and polysorbate; and (e) tonicity raising agents which stabilize and add tonicity, including, for example, sorbitol, mannitol, trehalose, sucrose, propylene glycol and glycerol.

As discussed above, the compositions of the present invention, including gas and/or gaseous precursor filled vesicles, are useful as contrast agents for diagnostic imaging, including, for example, ultrasound (US) imaging, computed tomography (CT) imaging, including CT angiography (CTA) imaging, magnetic resonance (MR) imaging, magnetic resonance angiography (NIRA), nuclear medicine, optical imaging and elastography.

In carrying out the magnetic resonance imaging method of the present invention, the contrast agent can be used alone, or in combination with other diagnostic, therapeutic or other agents. Such other agents include excipients such as flavoring or coloring materials. The magnetic resonance imaging techniques which are employed are conventional and are described, for example, in D. M. Kean and M. A. Smith, *Magnetic Resonance Imaging: Principles and Applications*, (William and Wilkins, Baltimore 1986). Contemplated MRI techniques include, but are not limited to, nuclear magnetic resonance (NMR) and electronic spin resonance (ESR). The preferred imaging modality is NMR.

Exemplary paramagnetic contrast agents suitable for use in the present compositions include, for example, stable free radicals, such as, for example, stable nitroxides, as well as compounds comprising transition, lanthanide and actinide elements, which may, if desired, be in the form of a salt or may be covalently or non-covalently bound to complexing agents, including lipophilic derivatives thereof, or to proteinaceous macromolecules.

Preferable transition, lanthanide and actinide elements include, for example, Gd(III), Mn(II), Cu(II), Cr(III), Fe(II), Fe(II), Co(II), Er(II), Ni(II), Eu(III) and Dy(III). More preferably, the elements may be Gd(III), Mn(II), Cu(II), Fe(II), Fe(III), Eu(III) and Dy(III), especially Mn(II) and Gd(III).

The foregoing elements may, if desired, be in the form of a salt, including inorganic salts, such as a manganese salt, for example, manganese chloride, manganese carbonate, manganese acetate, and organic salts, such as manganese gluconate and manganese hydroxylapatite. Other exemplary salts include salts of iron, for example, iron sulfides and ferric salts such as ferric chloride.

These elements may also, if desired, be bound, for example, through covalent or noncovalent association, to complexing agents, including lipophilic derivatives thereof, or to proteinaceous macromolecules. Preferable complexing agents include, for example, diethylenetriaminepentaacetic acid (DTPA), ethylene-diaminetetraacetic acid (EDTA), 1,4, 7,10-tetraazacyclododecane-N,N',N'',N'''-tetraacetic acid (DOTA), 1,4,7,10-tetraazacyclododecane-N,N',N''-triacetic acid (DOTA), 3,6,9-triaza-12-oxa-3,6,9-tricarboxymethylene-10-carboxy-13 -phenyl-tridecanoic acid (B-19036), hydroxybenzylethylenediamine diacetic acid (HBED), N,N'-bis(pyridoxyl-5-phosphate)ethylene diamine, N,N'-diacetate (DPDP), 1,4,7-triazacyclononane-N,N',N''-triacetic acid (NOTA), 1,4,8,11-tetraazacyclotetradecane-N,N',N'',N'''-tetraacetic acid (TETA), kryptands (macrocyclic complexes), and desferrioxamine. More preferably, the complexing agents are EDTA, DTPA, DOTA, DO3A and kryptands, most preferably DTPA. Preferable lipophilic complexes include alkylated derivatives of the complexing agents EDTA, DOTA, for example, N,N'-bis-(carboxydecylamidomethyl-N-2,3-dihydroxypropyl)-ethylenediamine-N,N'-diacetate (EDTA-DDP); N,N'-bis-(carboxyoctadecylamido-methyl-N-2,3-dihydroxypropyl)-ethylenediamine-N,N'-diacetate (EDTA-ODP); N,N'-Bis(carboxy-laurylamidomethyl-N-2,3-dihydroxypropyl)ethylenediamine-N,N'-diacetate (EDTA-LDP); and the like, including those described in U.S. Pat. No. 5,312,617, the disclosures of which are hereby incorporated herein by reference, in their entirety. Preferable proteinaceous macromolecules include, for example, albumin, collagen, polyarginine, polylysine, polyhistidine, γ-globulin and β-globulin, with albumin, polyarginine, polylysine, and polyhistidine being more preferred.

Suitable complexes therefore include Mn(II)-DTPA, Mn(II)-EDTA, Mn(II)-DOTA, Mn(II)-DO3A, Mn(II)-kryptands, Gd(III)-DTPA, Gd(III)-DOTA, Gd(III)-DO3A, Gd(III)-kryptands, Cr(III)-EDTA, Cu(II)-EDTA, or iron-desferrioxamine, especially Mn(II)-DTPA or Gd(III)-DTPA.

Nitroxides are paramagnetic contrast agents which increase both T1 and T2 relaxation rates on MRI by virtue of the presence of an unpaired electron in the nitroxide molecule. As known to one of ordinary skill in the art, the paramagnefic effectiveness of a given compound as an MRI contrast agent may be related, at least in part, to the number of unpaired electrons in the paramagnetic nucleus or molecule, and specifically, to the square of the number of unpaired electrons. For example, gadolinium has seven unpaired electrons whereas a nitroxide molecule has one unpaired electron. Thus, gadolinium is generally a much stronger MRI contrast agent than a nitroxide. However, the effective correlation time, another important parameter for assessing the effectiveness of contrast agents, confers potential increased relaxivity to the nitroxides. When the tumbling rate is slowed, for example, by attaching the paramagnetic contrast agent to a large molecule, it will tumble more slowly and thereby more effectively transfer energy to hasten relaxation of the water protons. In gadolinium, however, the electron spin relaxation time is rapid and will limit the extent to which slow rotational correlation times can increase relaxivity. For nitroxides, however, the electron spin correlation times are more favorable and tremendous increases in relaxivity may be attained by slowing the rotational correlation time of these molecules. The gas filled vesicles of the present invention are ideal for attaining the goals of slowed rotational correlation times and resultant improvement in relaxivity. Although not intending to be bound by any particular theory of operation, it is contemplated that since the nitroxides may be designed to coat the perimeters of the vesicles, for example, by making alkyl derivatives thereof, the resulting correlation times can be optimized. Moreover, the resulting contrast medium of the present invention may be viewed as a magnetic sphere, a geometric configuration which maximizes relaxivity.

If desired, the nitroxides may be alkylated or otherwise derivatized, such as the nitroxides 2,2,5,5-tetramethyl-1-pyrrolidinyloxy, free radical, and 2,2,6,6-tetramethyl-1-piperidinyloxy, free radical (TMPO).

Exemplary superparamagnetic contrast agents suitable for use in the compositions of the present invention include metal oxides and sulfides which experience a magnetic domain, ferro- or ferrimagnetic compounds, such as pure iron, magnetic iron oxide, such as magnetite, $\gamma$-$Fe_2O_3$, $Fe_3O_4$, manganese ferrite, cobalt ferrite and nickel ferrite. Paramagnetic gases can also be employed in the present compositions, such as oxygen 17 gas ($^{17}O_2$). In addition, hyperpolarized xenon, neon, or helium gas may also be employed. MR whole body imaging may then be employed to rapidly screen the body, for example, for thrombosis, and ultrasound may be applied, if desired, to aid in thrombolysis.

The contrast agents, such as the paramagnetic and superparamagnetic contrast agents described above, may be employed as a component within the lipid, protein, polymer, and/or vesicle compositions. In the case of vesicle compositions, the aforementioned contrast agents may be entrapped within the internal void thereof, administered as a solution with the vesicles, incorporated with any additional stabilizing materials, or coated onto the surface or membrane of the vesicle.

If desired, the paramagnetic or superparamagnetic agents may be delivered as alkylated or other derivatives incorporated into the compositions, especially the lipidic walls of the vesicles. In particular, the nitroxides 2,2,5,5-tetramethyl-1-pyrrolidinyloxy, free radical and 2,2,6,6-tetramethyl-1-piperidinyloxy, free radical, can form adducts with long chain fatty acids at the positions of the ring which are not occupied by the methyl groups via a variety of linkages, including, for example, an acetyloxy linkage. Such adducts are very amenable to incorporation into the lipid and/or vesicle compositions of the present invention.

Mixtures of any one or more of the paramagnetic agents and/or superparamagnetic agents in the present compositions may be used. The paramagnetic and superparamagnetic agents may also be coadministered separately, if desired.

The lipid, protein, polymer, and/or vesicle compositions of the present invention, and especially the vesicle compositions, may serve not only as effective carriers of the superparamagnetic agents described above, but also may improve the effect of the susceptibility contrast agents. Superparamagnetic contrast agents include metal oxides, particularly iron oxides but including manganese oxides, and as iron oxides, containing varying amounts of manganese, cobalt and nickel which experience a magnetic domain. These agents are nano or microparticles and have very high bulk susceptibilities and transverse relaxation rates. The larger particles, for example, particles having diameters of about 100 nm, have much higher R2 relaxivities as compared to R1 relaxivities. The smaller particles, for example, particles having diameters of about 10 to about 15 nm, have somewhat lower R2 relaxivities, but much more balanced R1 and R2 values. Much smaller particles, for example, monocrystalline iron oxide particles having diameters of about 3 to about 5 nm, have lower R2 relaxivities, but probably the most balanced R1 and R2 relaxation rates. Ferritin can also be formulated to encapsulate a core of very high relaxation rate superparamagnetic iron. It has been discovered that the lipid and/or vesicle compositions, especially vesicle compositions, including gas filled vesicles, can increase the efficacy and safety of these conventional iron oxide based MRI contrast agents.

The iron oxides may simply be incorporated into the lipid and/or vesicle compositions. Preferably, in the case of vesicles formulated from lipids, the iron oxides may be incorporated into the walls of the vesicles, for example, by being adsorbed onto the surfaces of the vesicles, or entrapped within the interior of the vesicles as described in U.S. Pat. No. 5,088,499, the disclosures of which are hereby incorporated herein by reference in their entirety.

Without being bound to any particular theory or theories of operation, it is believed that the compositions of the present invention, and especially the vesicle compositions, increase the efficacy of the superparamagnetic contrast agents by several mechanisms. First, it is believed that the vesicles function to increase the apparent magnetic concentration of the iron oxide particles. Also, it is believed that the vesicles increase the apparent rotational correlation time of the MRI contrast agents, including paramagnetic and superparamagnetic agents, so that relaxation rates are increased. In addition, the vesicles appear to increase the apparent magnetic domain of the contrast medium according to the manner described hereinafter.

Certain of the vesicles of the present invention, and especially vesicles formulated from lipids, may be visualized as flexible spherical domains of differing susceptibility from the suspending medium, including, for example, the aqueous suspension of the contrast medium or blood or other body fluids, for example, in the case of intravascular injection or injection into other body locations. In the case of ferrites or iron oxide particles, it should be noted that the contrast provided by these agents is dependent on particle size. This phenomenon is very common and is often referred to as the "secular" relaxation of the water molecules. Described in more physical terms, this relaxation mechanism is dependent upon the effective size of the molecular complex in which a paramagnetic atom, or paramagnetic molecule, or molecules, may reside. One physical explanation may be described in the following Solomon-Bloembergen equations which define the paramagnetic contributions as a function of the $T_1$ and $T_2$ relaxation times of a spin ½ nucleus with gyromagnetic ratio g perturbed by a paramagnetic ion:

$$1/T_1M = (2/15)S(S+1)\gamma^2 g^2 \beta^2/r^6[3\tau_c/(1+\omega_I^2\tau_c^2)+7\tau_c/(1+\omega_s^2\tau_c^2)] + (2/3)S(S+1)A^2/h^2[\tau_e/(1+\omega_s 2\tau_e^2)]$$

and $$1/T_2M = (1/15)S(S+1)\gamma^2 g^2 \beta^2/r^6[4\tau_c + 3\tau c/(1+\omega_I^2\tau_c^2) + 13\tau_c/(1+w_s^2\tau_c^2)] + (1/3)S(S+1)A^2/h^2[\tau_e/(1+\omega_s 2\tau_e^2)]$$

where:

S is the electron spin quantum number;

g is the electronic g factor;

β is the Bohr magneton;

ωI and $\omega_s$ (657 $W_I$) is the Larmor angular precession frequencies for the nuclear spins and electron spins;

r is the ion-nucleus distance;

A is the hyperfine coupling constant;

$\tau_c$ and $\tau_e$ are the correlation times for the dipolar and scalar interactions, respectively; and h is Planck's constant.

See, e.g., Solomon, I. *Phys. Rev.* Vol. 99, p. 559 (1955) and Bloembergen, N. *J. Chem. Phys.* Vol. 27, pp. 572, 595 (1957).

A few large particles may have a much greater effect than a larger number of much smaller particles, primarily due to a larger correlation time. If one were to make the iron oxide particles very large however, increased toxicity may result, and the lungs may be embolized or the complement cascade system may be activated. Furthermore, it is believed that the total size of the particle is not as important as the diameter of the particle at its edge or outer surface. The domain of magnetization or susceptibility effect falls off exponentially from the surface of the particle. Generally speaking, in the case of dipolar (through space) relaxation mechanisms, this exponential fall off exhibits an $r^6$ dependence for a paramagnetic dipole-dipole interaction. Interpreted literally, a water molecule that is 4 angstroms away from a paramagnetic surface will be influenced 64 times less than a water molecule that is 2 angstroms away from the same paramagnetic surface. The ideal situation in terms of maximizing the contrast effect would be to make the iron oxide particles hollow, flexible and as large as possible. It has not been possible to achieve this heretofore and it is believed that the benefits have been unrecognized heretofore also. By coating the inner or outer surfaces of the vesicles with the contrast agents, even though the individual contrast agents, for example, iron oxide nanoparticles or paramagnetic ions, are relatively small structures, the effectiveness of the contrast agents may be greatly enhanced. In so doing, the contrast agents may function as an effectively much larger sphere wherein the effective domain of magnetization is determined by the diameter of the vesicle and is maximal at the surface of the vesicle. These agents afford the advantage of flexibility, namely, compliance. While rigid vesicles might lodge in the lungs or other organs and cause toxic reactions, these flexible vesicles slide through the capillaries much more easily.

In contrast to the flexible vesicles described above, it may be desirable, in certain circumstances, to formulate vesicles from substantially impermeable materials such as polymer materials, including, for example, polymethyl methacrylate. This would generally result in the formation of vesicles which may be substantially impermeable and relatively inelastic and brittle. In embodiments involving diagnostic imaging, for example, ultrasound, contrast media which comprise such brittle vesicles would generally not provide the desirable reflectivity that the flexible vesicles may provide. However, by increasing the power output on ultrasound, the brittle vesicles can be made to rupture, thereby causing acoustic emissions which can be detected by an ultrasound transducer.

Nuclear Medicine Imaging (NMI) may also be used in connection with the diagnostic and therapeutic method aspects of the present invention. For example, NMI may be used to detect radioactive gases, such as $Xe^{133}$, which may be incorporated in the present compositions in addition to, or instead of the gases discussed above. Such radioactive gases may be entrapped within vesicles for use in detecting, for example, thrombosis. Preferably, bifunctional chelate derivatives are incorporated in the walls of vesicles, and the resulting vesicles may be employed in both NMI and ultrasound. In this case, high energy, high quality nuclear medicine imaging isotopes, such as technetium$^{99m}$ or indium$^{111}$ can be incorporated in the walls of vesicles. Whole body gamma scanning cameras can then be employed to rapidly localize regions of vesicle uptake in vivo. If desired, ultrasound may also be used to confirm the presence, for example, of a clot within the blood vessels, since ultrasound generally provides improved resolution as compared to nuclear medicine techniques. NMI may also be used to screen the entire body of the patient to detect areas of vascular thrombosis, and ultrasound can be applied to these areas locally to promote rupture of the vesicles and treat the clot.

As noted above, the present compositions may also be employed in connection with computed tomography (CT) imaging. CT suffers from various drawbacks, and is generally less effective as compared to the diagnostic techniques discussed above. Nevertheless, if a high enough concentration of the present contrast media, and especially gas filled vesicle compositions, is delivered to the region of interest, for example, a blood clot, the clot can be detected on the CT images by virtue of a decrease in the overall density of the clot. In general, a concentration of about ¹/₁₀ of 1% of gas filled vesicles or higher (on a volume basis), may be needed to be delivered to the region of interest, including the aforementioned blood clot, to be detected by CT.

Also, for optical imaging, optically active gases, such as argon or neon, may be incorporated in the present compositions. In addition, optically active materials, for example, fluorescent materials, including porphyrin derivatives, may also be used. Elastography is an imaging technique which generally employs much lower frequency sound, for example, about 60 KHz, as compared to ultrasound which can involve over frequencies of over 1 MHZ. In elastography, the sound energy is generally applied to the tissue and the elasticity of the tissue may then be determined. The lipid based vesicles described herein are preferably highly elastic, and they may increase the local elasticity of tissue to which they are directed. This increased elasticity may then be detected with elastography. If desired, elastography can be used in conjunction with other imaging techniques, such as MRI and ultrasound.

A wide variety of methods are available for the preparation of lipid, protein, polymer, and/or vesicle compositions, such as micelles and/or liposomes. Included among these methods are, for example, shaking, drying, gas-installation, spray drying, and the like. Suitable methods for preparing vesicle compositions from lipids are described, for example, in Unger et al., U.S. Pat. No. 5,469,854, the disclosures of which are hereby incorporated herein by reference, in their entirety. As noted above, the vesicles are preferably prepared from lipids which remain in the gel state.

With particular reference to the preparation of micelle compositions, the following discussion is provided. Micelles may be prepared using any one of a variety of conventional micellar preparatory methods which will be apparent to those skilled in the art. These methods typically involve suspension of one or more lipid compounds in an organic solvent, evaporation of the solvent, resuspension in an aqueous medium, sonication and centrifugation. The foregoing methods, as well as others, are discussed, for example, in Canfield et al., *Methods in Enzymology*, Vol. 189, pp. 418–422 (1990); El-Gorab et al., *Biochem. Biophys. Acta*, Vol. 306, pp. 58–66 (1973); *Colloidal Surfactant*, Shinoda, K., Nakagana, Tamamushi and Isejura, Academic Press, N.Y. (1963) (especially "The Formation of Micelles", Shinoda, Chapter 1, pp. 1–88); *Catalysis in Micellar and Macromolecular Systems*, Fendler and Fendler, Academic Press, N.Y. (1975). The disclosures of each of the foregoing publications are incorporated by reference herein, in their entirety.

As noted above, the vesicle composition may comprise liposomes. A wide variety of methods are available in connection with the preparation of liposome compositions. Accordingly, the liposomes may be prepared using any one of a variety of conventional liposomal preparatory techniques which will be apparent to those skilled in the art. These techniques include, for example, solvent dialysis, French press, extrusion (with or without freeze-thaw), reverse phase evaporation, simple freeze-thaw, sonication, chelate dialysis, homogenization, solvent infusion, microemulsification, spontaneous formation, solvent vaporization, solvent dialysis, French pressure cell technique, controlled detergent dialysis, and others, each involving the preparation of the vesicles in various fashions. Yee, e.g., Madden et al., *Chemistry and Physics of lipids*, 1990 53, 37–46, the disclosures of which are hereby incorporated herein by reference in their entirety. Suitable freeze-thaw techniques are described, for example, in International Application Serial No. PCT/US89/05040, filed Nov. 8, 1989, the disclosures of which are incorporated herein by reference in their entirety. Methods which involve freeze-thaw techniques are preferred in connection with the preparation of liposomes. Preparation of the liposomes may be carried out in a solution, such as an aqueous saline solution, aqueous phosphate buffer solution, or sterile water. The liposomes may also be prepared by various processes which involve shaking or vortexing. This may be achieved, for example, by the use of a mechanical shaking device, such as a Wig-L-Bug™ (Crescent Dental, Lyons, Ill.), a Mixomat (Degussa AG, Frankfurt, Germany), a Capmix (Espe Fabrik Pharmazeutischer Praeparate GMBH & Co., Seefeld, Oberay Germany), a Silamat Plus (Vivadent, Liechtenstein), or a Vibros (Quayle Dental, Sussex, England). Conventional microemulsification equipment, such as a Microfluidizer™ (Microfluidics, Woburn, Mass.) may also be used.

Spray drying may be also employed to prepare the gas-filled vesicles. Utilizing this procedure, the lipids may be pre-mixed in an aqueous environment and then spray dried to produce gas-filled vesicles. The vesicles may be stored under a headspace of a desired gas.

Many liposomal preparatory techniques which may be adapted for use in the preparation of vesicle compositions are discussed, for example, in U.S. Pat. No. 4,728,578; U.K. Patent Application GB 2193095 A; U.S. Pat. No. 4,728,575; U.S. Pat. No. 4,737,323; International Application Serial No. PCT/US85/01161; Mayer et al., *Biochimica et Biophysica Acta*, Vol. 858, pp. 161–168 (1986); Hope et al., *Biochimica et Biophysica Acia*, Vol. 812, pp. 55–65 (1985); U.S. Pat. No. 4,533,254; Mayhew et al., *Methods in Enzymology*, Vol. 149, pp. 64–77 (1987); Mayhew et al., *Biochimica et Biophysica Acia*, Vol 755, pp. 169–74 (1984); Cheng et al., *Investigative Radiology*, Vol. 22, pp. 47–55 (1987); International Application Serial No. PCT/US89/05040; U.S. Pat. No. 4,162,282; U.S. Pat. No. 4,310,505; U.S. Pat. No. 4,921,706; and *Liposome Technology*, Gregoriadis, G., ed., Vol. I, pp. 29–31, 51–67 and 79–108 (CRC Press Inc., Boca Raton, Fla. 1984), the disclosures of each of which are hereby incorporated by reference herein, in their entirety.

Lipid compositions comprising a gas can be prepared by agitating an aqueous solution containing, if desired, a stabilizing material, in the presence of a gas. The term "agitating," as used herein, means any shaking motion of an aqueous solution such that gas may be introduced from the local ambient environment into the aqueous solution. This agitation is preferably conducted at a temperature below the gel to liquid crystalline phase transition temperature of the lipid. The shaking involved in the agitation of the solutions is preferably of sufficient force to result in the formation of a lipid composition, including vesicle compositions, and particularly vesicle compositions comprising gas filled vesicles. The shaking may be by swirling, such as by vortexing, side-to-side, or up and down motion. Different types of motion may be combined. Also, the shaking may occur by shaking the container holding the aqueous lipid solution, or by shaking the aqueous solution within the container without shaking the container itself The shaking may occur manually or by machine. Mechanical shakers that may be used include, for example, a shaker table such as a VWR Scientific (Cerritos, Calif.) shaker table, as well as any of the shaking devices described hereinbefore, with the Capmix (Espe Fabrik Pharmazeutischer Praeparate GMBH & Co., Seefeld, Oberay Germany) being preferred. It has been found that certain modes of shaking or vortexing can be used to make vesicles within a preferred size range. Shaking is preferred, and it is preferred that the shaking be carried out using the Espe Capmix mechanical shaker. In accordance with this preferred method, it is preferred that a reciprocating motion be utilized to generate the lipid compositions, and particularly vesicle compositions. It is even more preferred that the motion be reciprocating in the form of an arc. It is contemplated that the rate of reciprocation, as well as the arc thereof, is particularly important in connection with the formation of vesicles. Preferably, the number of reciprocations or full cycle oscillations may be from about 1000 to about 20,000 per minute. More preferably, the number of reciprocations or oscillations may be from about 2500 to about 8000 per minute, with from about 3300 to about 5000 reciprocations or oscillations per minute being even more preferred. Of course, the number of oscillations may be dependent upon the mass of the contents being agitated. Generally speaking, a larger mass may require fewer oscillations. Another means for producing shaking includes the action of gas emitted under high velocity or pressure.

It will also be understood that preferably, with a larger volume of aqueous solution, the total amount of force may be correspondingly increased. Vigorous shaking is defined as at least about 60 shaking motions per minute, and is preferred. Vortexing at about 60 to about 300 revolutions per minute is more preferred. Vortexing at about 300 to about 1800 revolutions per minute is even more preferred.

In addition to the simple shaking methods described above, more elaborate methods can also be employed. Such elaborate methods include, for example, liquid crystalline shaking gas instillation processes and vacuum drying gas instillation processes, such as those described in copending U.S. application Ser. No. 08/076,250, filed Jun. 11, 1993, the disclosures of which are incorporated herein by reference, in their entirety. Although any of a number of varying techniques can be used, the vesicle compositions employed in the present invention are preferably prepared using a shaking technique. Preferably, the shaking technique involves agitation with a mechanical shaking apparatus, such as an Espe Capmix (Seefeld, Oberay Germany), using, for example, the techniques disclosed in copending U.S. application Ser. No. 160,232, filed Nov. 30, 1993, the disclosures of which are hereby incorporated herein by reference in their entirety.

The size of gas filled vesicles can be adjusted, if desired, by a variety of procedures, including, for example, microemulsification, vortexing, extrusion, filtration, sonication, homogenization, repeated freezing and thawing cycles, extrusion under pressure through pores of defined size, and similar methods. Gas filled vesicles prepared in accordance with the methods described herein can range in size from less than about 1 βm to greater than about 100 μm. In addition, after extrusion and sterilization procedures, which are discussed in detail below, agitation or shaking may provide vesicle compositions which can contain substantially no or minimal residual anhydrous lipid phase in the remainder of the solution. (Bangham, A. D., Standish, M. M, & Watkins, J. C., *J. Mol. Biol.* Vol. 13, pp. 23 8–252 (1965). If desired, the vesicles may be used as they are formed, without any attempt at further modification of the size thereof For intravascular use, the vesicles preferably have diameters of less than about 30 μm, and more preferably, less than about 12 μm. For targeted intravascular use including, for example, binding to certain tissue, such as cancerous tissue, the vesicles may be significantly smaller, for example, less than about 100 nm in diameter. For enteric or gastrointestinal use, the vesicles may be significantly larger, for example, up to a millimeter in size. Preferably, the vesicles may be sized to have diameters of from about 2 μm to about 100 μm.

The gas filled vesicles may be sized by a simple process of extrusion through filters wherein the filter pore sizes control the size distribution of the resulting gas filled vesicles. By using two or more cascaded or stacked set of filters, for example, a 10 lm filter followed by an 8 μm filter, the gas filled vesicles can be selected to have a very narrow size distribution around 7 to 9 μm. After filtration, these gas filled vesicles can remain stable for over 24 hours.

The sizing or filtration step may be accomplished by the use, for example, of a filter assembly when the composition is removed from a sterile vial prior to use, or more preferably, the filter assembly may be incorporated into a syringe during use. The method of sizing the vesicles will then comprise using a syringe comprising a barrel, at least one filter, and a needle; and may be carried out by a step of extracting which comprises extruding the vesicles from the barrel through the filter fitted to the syringe between the barrel and the needle, thereby sizing the vesicles before they are administered to a patient. The step of extracting may also comprise drawing the vesicles into the syringe, where the filter may function in the same way to size the vesicles upon entrance into the syringe. Another alternative is to fill such a syringe with vesicles which have already been sized by some other means, in which case the filter may function to ensure that only vesicles within the desired size range, or of the desired maximum size, are subsequently administered by extrusion from the syringe.

In certain preferred embodiments, the vesicle compositions may be heat sterilized or filter sterilized and extruded through a filter prior to shaking. Generally speaking, vesicle compositions comprising a gas may be heat sterilized, and vesicle compositions comprising gaseous precursors may be filter sterilized. Once gas filled vesicles are formed, they may be filtered for sizing as described above. Performing these steps prior to the formation of gas and gaseous precursor filled vesicles provide sterile gas filled vesicles ready for administration to a patient. For example, a mixing vessel such as a vial or syringe may be filled with a filtered lipid and/or vesicle composition, and the composition may be sterilized within the mixing vessel, for example, by autoclaving. Gas may be instilled into the composition to form gas filled vesicles by shaking the sterile vessel. Preferably, the sterile vessel is equipped with a filter positioned such that the gas filled vesicles pass through the filter before contacting a patient.

The step of extruding the solution of lipid compound through a filter decreases the amount of unhydrated material by breaking up any dried materials and exposing a greater surface area for hydration. Preferably, the filter has a pore size of about 0.1 to about 5 μm, more preferably, about 0.1 to about 4 μm, even more preferably, about 0.1 to about 2 μm, and still more preferably, about 1 μm. Unhydrated compound, which is generally undesirable, appears as amorphous clumps of non-uniform size.

The sterilization step provides a composition that may be readily administered to a patient for diagnostic imaging including, for example, ultrasound, MRI or CT. In certain preferred embodiments, sterilization may be accomplished by heat sterilization, preferably, by autoclaving the solution at a temperature of at least about 100° C., and more preferably, by autoclaving at about 100° C. to about 130° C., even more preferably, about 110° C. to about 130° C., still more preferably, about 120° C. to about 130° C., and even more preferably, about 130° C. Preferably, heating occurs for at least about 1 minute, more preferably, about 1 to about 30 minutes, even more preferably, about 10 to about 20 minutes, and still more preferably, about 15 minutes.

If desired, the extrusion and heating steps, as outlined above, may be reversed, or only one of the two steps can be used. Other modes of sterilization may be used, including, for example, exposure to gamma radiation.

In addition to the aforementioned embodiments, gaseous precursors contained in vesicles can be formulated which, upon activation, for example, by exposure to elevated temperature, varying pH, or light, may undergo a phase transition from, for example, a liquid, including a liquid entrapped in a vesicle, to a gas, expanding to create the gas filled vesicles described herein. This technique is described in detail in copending patent applications Ser. Nos. 08/160,232, filed Nov. 30, 1993 and U.S. Ser. No. 08/159,687, filed Nov. 30, 1993, the disclosures of which are incorporated herein by reference, in their entirety.

The preferred method of activating the gaseous precursor is by exposure to elevated temperature. Activation or transition temperature, and like terms, refer to the boiling point of the gaseous precursor and is the temperature at which the liquid to gaseous phase transition of the gaseous precursor takes place. Useful gaseous precursors are those materials which have boiling points in the range of about $-100°$ C. to about $70°$ C. The activation temperature is particular to each gaseous precursor. An activation temperature of about $37°$ C., or about human body temperature, is preferred for gaseous precursors in the context of the present invention. Thus, in preferred form, a liquid gaseous precursor is activated to become a gas at about $37°$ C. or below. The gaseous precursor may be in liquid or gaseous phase for use in the methods of the present invention.

The methods of preparing the gaseous precursor filled vesicles may be carried out below the boiling point of the gaseous precursor such that a liquid is incorporated, for example, into a vesicle. In addition, the methods may be conducted at the boiling point of the gaseous precursor, such that a gas is incorporated, for example, into a vesicle. For gaseous precursors having low temperature boiling points, liquid precursors may be emulsified using a microfluidizer device chilled to a low temperature. The boiling points may also be depressed using solvents in liquid media to utilize a precursor in liquid form. Further, the methods may be performed where the temperature is increased throughout the process, whereby the process starts with a gaseous precursor as a liquid and ends with a gas.

The gaseous precursor may be selected so as to form the gas in situ in the targeted tissue or fluid, in vivo upon entering the patient or animal, prior to use, during storage, or during manufacture. The methods of producing the temperature-activated gaseous precursor filled vesicles may be carried out at a temperature below the boiling point of the gaseous precursor. In this embodiment, the gaseous precursor may be entrapped within a vesicle such that the phase transition does not occur during manufacture. Instead, the gaseous precursor filled vesicles are manufactured in the liquid phase of the gaseous precursor. Activation of the phase transition may take place at any time as the temperature is allowed to exceed the boiling point of the precursor. Also, knowing the amount of liquid in a droplet of liquid gaseous precursor, the size of the vesicles upon attaining the gaseous state may be determined.

Alternatively, the gaseous precursors may be utilized to create stable gas filled vesicles which are pre-formed prior to use. In this embodiment, the gaseous precursor may be added to a container housing a lipid composition at a temperature below the liquid-gaseous phase transition temperature of the respective gaseous precursor. As the temperature is increased, and an emulsion is formed between the gaseous precursor and liquid solution, the gaseous precursor undergoes transition from the liquid to the gaseous state. As a result of this heating and gas formation, the gas displaces the air in the head space above the liquid mixture so as to form gas filled vesicles which may entrap the gas of the gaseous precursor, ambient gas (e.g. air), or coentrap gas state gaseous precursor and ambient air. This phase transition can be used for optimal mixing and formation of the contrast agent. For example, the gaseous precursor, perfluorobutane, can be entrapped in the lipid vesicles and as the temperature is raised beyond the boiling point of perfluorobutane ($4°$ C.), perfluorobutane gas is entrapped in the vesicles.

Accordingly, the gaseous precursors may be selected to form gas filled vesicles in vivo or may be designed to produce the gas filled vesicles in situ, during the manufacturing process, on storage, or at some time prior to use.

As a further embodiment of this invention, by preforming the gaseous precursor in the liquid state into an aqueous emulsion, the maximum size of the vesicle may be estimated by using the ideal gas law, once the transition to the gaseous state is effectuated. For the purpose of making gas filled vesicles from gaseous precursors, the gas phase may be assumed to form instantaneously and substantially no gas in the newly formed vesicle has been depleted due to diffusion into the liquid, which is generally aqueous in nature. Hence, from a known liquid volume in the emulsion, one may predict an upper limit to the size of the gas filled vesicle.

In embodiments of the present invention, a mixture of a lipid compound and a gaseous precursor, containing liquid droplets of defined size, may be formulated such that upon reaching a specific temperature, for example, the boiling point of the gaseous precursor, the droplets may expand into gas filled vesicles of defined size. The defined size may represent an upper limit to the actual size because the ideal gas law generally cannot account for such factors as gas diffusion into solution, loss of gas to the atmosphere, and the effects of increased pressure.

The ideal gas law, which can be used for calculating the increase in the volume of the gas bubbles upon transitioning from liquid to gaseous states, is as follows:

$$PV=nRT$$

where

P is pressure in atmospheres (atm);

V is volume in liters (L);

n is moles of gas;

T is temperature in degrees Kelvin (K); and

R is the ideal gas constant (22.4 L-atm/K-mole).

With knowledge of volume, density, and temperature of the liquid in the mixture of liquids, the amount, for example, in moles, and volume of liquid precursor may be calculated which, when converted to a gas, may expand into a vesicle of known volume. The calculated volume may reflect an upper limit to the size of the gas filled vesicle, assuming instantaneous expansion into a gas filled vesicle and negligible diffusion of the gas over the time of the expansion.

Thus, for stabilization of the precursor in the liquid state in a mixture wherein the precursor droplet is spherical, the volume of the precursor droplet may be determined by the equation:

$$\text{Volume (spherical vesicle)} = 4/3\pi r^3$$

where r is the radius of the sphere.

Thus, once the volume is predicted, and knowing the density of the liquid at the desired temperature, the amount of liquid gaseous precursor in the droplet may be determined. In more descriptive terms, the following can be applied:

$$V_{gas} = 4/3\pi (r_{gas})^3$$

by the ideal gas law, $$PV = nRT$$

substituting reveals, $$V_{gas} = nRT/P_{gas}$$

or, $$n = 4/3[\pi r_{gas}^3]P/RT \quad (A)$$

amount $n = 4/3[\pi r_{gas}^3 P/RT] \cdot MW_n$
Converting back to a liquid volume $$V_{liq} = [4/3[\pi r_{gas}^3]P/RT] \cdot MW_n/D] \quad (B)$$

where D is the density of the precursor.
Solving for the diameter of the liquid droplet, $$\text{diameter}/2 = [3/4\pi[4/3 \cdot [\pi r_{gas}^3]P/RT]MW_n/D]]^{1/3} \quad (C)$$

which reduces to $$\text{Diameter} = 2[[r_{gas}^3]P/RT[MW_n/D]]^{1/3}$$

As a further means of preparing vesicles of the desired size for use in the methods of the present invention, and with a knowledge of the volume and especially the radius of the liquid droplets, one can use appropriately sized filters to size the gaseous precursor droplets to the appropriate diameter sphere.

A representative gaseous precursor may be used to form a vesicle of defined size, for example, 10 μm diameter. In this example, the vesicle may be formed in the bloodstream of a human being, thus the typical temperature would be 37° C. or 310° K. At a pressure of 1 atmosphere and using the equation in (A), $7.54 \times 10^{-17}$ moles of gaseous precursor may be required to fill the volume of a 10 μm diameter vesicle.

Using the above calculated amount of gaseous precursor and 1-fluorobutane, which possesses a molecular weight of 76.11, a boiling point of 32.5° C. and a density of 0.7789 g/mL at 20° C., further calculations predict that $5.74 \times 10^{-15}$ grams of this precursor may be required for a 10 μm vesicle. Extrapolating further, and with the knowledge of the density, equation (B) further predicts that $8.47 \times 10^{-16}$ mL of liquid precursor may be necessary to form a vesicle with an upper limit of 10 μm.

Finally, using equation (C), a mixture, for example, an emulsion containing droplets with a radius of 0.0272 μm or a corresponding diameter of 0.0544 μm, may be formed to make a gaseous precursor filled vesicle with an upper limit of a 10 μm vesicle.

An emulsion of this particular size could be easily achieved by the use of an appropriately sized filter. In addition, as seen by the size of the filter necessary to form gaseous precursor droplets of defined size, the size of the filter may also suffice to remove any possible bacterial contaminants and, hence, can be used as a sterile filtration as well.

This embodiment for preparing gas filled vesicles may be applied to all gaseous precursors activated by temperature. In fact, depression of the freezing point of the solvent system allows the use of gaseous precursors which may undergo liquid-to-gas phase transitions at temperatures below 0° C. The solvent system can be selected to provide a medium for suspension of the gaseous precursor. For example, 20% propylene glycol miscible in buffered saline exhibits a freezing point depression well below the freezing point of water alone. By increasing the amount of propylene glycol or adding materials such as sodium chloride, the freezing point can be depressed even further.

The selection of appropriate solvent systems may be determined by physical methods as well. When substances, solid or liquid, herein referred to as solutes, are dissolved in a solvent, such as water based buffers, the freezing point may be lowered by an amount that is dependent upon the composition of the solution. Thus, as defined by Wall, one can express the freezing point depression of the solvent by the following equation:

$$\ln x_a = \ln(1-x_b) = \Delta H_{fus}/R(1/T_o - 1/T)$$

where $x_a$ is the mole fraction of the solvent;

$x_b$ is the mole fraction of the solute;

$\Delta H_{fus}$ is the heat of fusion of the solvent; and $T_o$ is the normal freezing point of the solvent.

The normal freezing point of the solvent can be obtained by solving the equation. If $x_b$ is small relative to $x_a$, then the above equation may be rewritten as follows.

$$x^b = \Delta H_{fus}/R[T-T_o/T_oT] = \Delta H_{fus} \Delta T/RT_o^2$$

The above equation assumes the change in temperature ΔT is small compared to $T_2$. This equation can be simplified further by expressing the concentration of the solute in terms of molality, m (moles of solute per thousand grams of solvent). Thus, the equation can be rewritten as follows.

$$X_b = m/[m+1000/m_a] = mMa/1000$$

where Ma is the molecular weight of the solvent.

Thus, substituting for the fraction $X_b$:

$$\Delta T = [^{Mardi}/1000\Delta H_{fus}]m$$

or $$\Delta T = K_f m,$$

where $$K_f = {}^{Mardi}/1000\Delta H_{fus}$$

$K_f$ is the molal freezing point and is equal to 1.86 degrees per unit of molal concentration for water at one atmosphere pressure. The above equation may be used to accurately determine the molal freezing point of solutions of gaseous-precursor filled vesicles. Accordingly, the above equation can be applied to estimate freezing point depressions and to determine the appropriate concentrations of liquid or solid solute necessary to depress the solvent freezing temperature to an appropriate value.

Methods of preparing the temperature activated gaseous precursor filled vesicles include:

(a) vortexing and/or shaking an aqueous mixture of gaseous precursor and additional materials as desired, including, for example, stabilizing materials, thickening agents and/or dispersing agents. Optional variations of this method include autoclaving before vortexing or shaking; heating an aqueous mixture of gaseous precursor; venting the vessel containing the mixture/suspension; shaking or permitting the gaseous precursor filled vesicle to form spontaneously and cooling down the suspension of gaseous precursor filled vesicles; and extruding an aqueous suspension of gaseous precursor through a filter of about 0.22 μm. Alternatively, filtering may be performed during in vivo administration of the vesicles such that a filter of about 0.22 μm is employed;

(b) microemulsification, whereby an aqueous mixture of gaseous precursor is emulsified by agitation and heated to form, for example, vesicles prior to administration to a patient;

(c) heating a gaseous precursor in a mixture, with or without agitation, whereby the less dense gaseous precursor filled vesicles may float to the top of the solution by expanding and displacing other vesicles in the vessel and venting the vessel to release air; and (d) utilizing in any of the above methods a sealed vessel to hold the aqueous suspension of gaseous precursor and maintaining the suspension at a temperature below the phase transition temperature of the gaseous precursor, followed by autoclaving to raise the temperature above the phase transition temperature, optionally with shaking, or permitting the gaseous precursor vesicle to form spontaneously, whereby the expanded gaseous precursor in the sealed vessel increases the pressure in the vessel, and cooling down the gas filled vesicle suspension, after which shaking may also take place.

Freeze drying may be useful to remove water and organic materials prior to the shaking installation method. Drying installation methods may be used to remove water from vesicles. By pre-entrapping the gaseous precursor in the dried vesicles (i.e. prior to drying) after warming, the gaseous precursor may expand to fill the vesicle. Gaseous precursors can also be used to fill dried vesicles after they have been subjected to vacuum. As the dried vesicles are kept at a temperature below their gel state to liquid crystalline temperature, the drying chamber can be slowly filled with the gaseous precursor in its gaseous state. For example, perfluorobutane can be used to fill dried vesicles at temperatures above 4° C. (the boiling point of perfluorobutane).

Preferred methods for preparing the temperature activated gaseous precursor filled vesicles comprise shaking an aqueous solution having a lipid compound in the presence of a gaseous precursor at a temperature below the liquid state to gas state phase transition temperature of the gaseous precursor. This is preferably conducted at a temperature below the gel state to liquid crystalline state phase transition temperature of the lipid. The mixture may be then heated to a temperature above the liquid state to gas state phase transition temperature of the gaseous precursor which can cause the precursor to volatilize and expand. Heating may be then discontinued, and the temperature of the mixture may be allowed to drop below the liquid state to gas state phase transition temperature of the gaseous precursor. Shaking of the mixture may take place during the heating step, or subsequently after the mixture is allowed to cool.

Other methods for preparing gaseous precursor filled vesicles can involve shaking an aqueous solution of, for example, a lipid and a gaseous precursor, and separating the resulting gaseous precursor filled vesicles.

Conventional, aqueous-filled liposomes of the prior art are routinely formed at a temperature above the phase transition temperature of the lipids used to make them, since they are more flexible and thus useful in biological systems in the liquid crystalline state. See, for example, Szoka and Papahadjopoulos, *Proc. Nadl. Acad. Sci.* 1978, 75, 4194–4198. In contrast, the vesicles made according to certain preferred embodiments described herein are gaseous precursor filled, which imparts greater flexibility, since gaseous precursors after gas formation are more compressible and compliant than an aqueous solution.

The preparatory methods may involve shaking an aqueous solution comprising a lipid, in the presence of a temperature activatable gaseous precursor. Preferably, the shaking is of sufficient force such that a foam is formed within a short period of time, such as about 30 minutes, and preferably within about 20 minutes, and more preferably, within about 10 minutes. The shaking may involve micro-emulsifying, microfluidizing, swirling (such as by vortexing), side-to-side, or up and down motion. In the case of the addition of gaseous precursor in the liquid state, sonication may be used in addition to the shaking methods set forth above. Further, different types of motion may be combined. Also, the shaking may occur by shaking the container holding the aqueous lipid solution, or by shaking the aqueous solution within the container without shaking the container itself Further, the shaking may occur manually or by machine. Mechanical shakers that may be used include, for example, the mechanical shakers described hereinbefore, with an Espe Capmix (Seefeld, Oberay Germany) being preferred. Another means for producing shaking includes the action of gaseous precursor emitted under high velocity or pressure.

According to the methods described herein, a gas, such as air, may also be provided by the local ambient atmosphere. The local ambient atmosphere can include the atmosphere within a sealed container, as well as the external environment. Alternatively, for example, a gas may be injected into or otherwise added to the container having the aqueous lipid solution or into the aqueous lipid solution itself to provide a gas other than air. Gases that are lighter than air are generally added to a sealed container, while gases heavier than air can be added to a sealed or an unsealed container. Accordingly, the present invention includes co-entrapment of air and/or other gases along with gaseous precursors.

Hence, the gaseous precursor filled vesicles can be used in substantially the same manner as the gas filled vesicles described herein, once activated by application to the tissues of a host, where such factors as temperature or pH may be used to cause generation of the gas. It is preferred that the gaseous precursors undergo phase transitions from liquid to gaseous states at near the normal body temperature of the host, and are thereby activated, for example, by the in vivo temperature of the host so as to undergo transition to the gaseous phase therein. This can occur where, for example, the host tissue is human tissue having a normal temperature of about 37° C. and the gaseous precursors undergo phase transitions from liquid to gaseous states near 37° C.

As noted above, the lipid, protein, polymer and/or vesicle compositions may be sterilized by autoclave or sterile filtration if these processes are performed before the installation step or prior to temperature mediated conversion of the temperature sensitive gaseous precursors within the compositions. Alternatively, one or more anti-bactericidal agents and/or preservatives may be included in the formulation of the compositions, such as sodium benzoate, quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulfur dioxide, and organic mercurial salts. Such sterilization, which may also be achieved by other conventional means, such as by irradiation, may be necessary where the stabilized vesicles are used for imaging under invasive circumstances, for example, intravascularly or intraperitonealy. The appropriate means of sterilization will be apparent to the artisan based on the present disclosure.

Vesicle compositions which comprise vesicles formulated from proteins or polymers may be prepared by various processes, as will be readily apparent to those skilled in the art, once armed with the present disclosure. Exemplary processes include, for example, interfacial polymerization, phase separation and coacervation, multiorifice centrifugal preparation, and solvent evaporation. Suitable procedures which may be employed or modified in accordance with the present disclosure to prepare vesicles from polymers include those procedures disclosed in Garner et al., U.S. Pat. No. 4,179,546, Garner, U.S. Pat. No. 3,945,956, Cohrs et al., U.S. Pat. No. 4,108,806, Japan Kokal Tokyo Koho 62 286534, British Pat. No. 1,044,680, Kenaga et al., U.S. Pat. No. 3,293,114, Morehouse et al., U.S. Pat. No. 3,401,475, Walters, U.S. Pat. No. 3,479,811, Walters et al., U.S. Pat. No. 3,488,714, Morehouse et al., U.S. Pat. No. 3,615,972, Baker et al., U.S. Pat. No. 4,549,892, Sands et al., U.S. Pat. No. 4,540,629, Sands et al., U.S. Pat. No. 4,421,562, Sands, U.S. Pat. No. 4,420,442, Mathiowitz et al., U.S. Pat. No. 4,898,734, Lencki et al., U.S. Pat. No. 4,822,534, Herbig et al., U.S. Pat. No. 3,732,172, Himmel et al., U.S. Pat. No. 3,594,326, Sommerville et al., U.S. Pat. No. 3,015,128, Deasy, *Microencapsulation and Related Drug Processes*, Vol. 20, Chs. 9 and 10, pp. 195–240 (Marcel Dekker, Inc., N.Y., 1984), Chang et al., *Canadian J. of Physiology and Phannacology*, Vol 44, pp. 115–129 (1966), and Chang, *Science*, Vol. 146, pp. 524–525 (1964), the disclosures of each of which are incorporated herein by reference in their entirety.

In accordance with a preferred synthesis protocol, the polymer vesicles may be prepared using a heat expansion process, such as, for example, the process described in Garner et al., U.S. Pat. No. 4,179,546, Gamer, U.S. Pat. No. 3,945,956, Cohrs et al., U.S. Pat. No. 4,108,806, British Pat. No. 1,044,680, and Japan Kokai Tokyo Koho 62 286534. In general terms, the heat expansion process may be carried out by preparing vesicles of an expandable polymer or copolymer which may contain in their void (cavity) a volatile liquid (gaseous precursor). The vesicle is then heated, plasticising the vesicle and converting the volatile liquid into a gas, causing the vesicle to expand to up to about several times its original size. When the heat is removed, the thermoplastic polymer retains at least some of its expanded shape. Vesicles produced by this process tend to be of particularly low density, and are thus preferred. The foregoing described process is well known in the art, and may be referred to as the heat expansion process for preparing low density vesicles.

Polymers useful in the heat expansion process will be readily apparent to those skilled in the art and include thermoplastic polymers or copolymers, including polymers or copolymers of many of the monomers described above. Preferable of the polymers and copolymers described above include the following copolymers: polyvinylidene-polyacrylonitrile, polyvinylidene-polyacrylonitrile-polymethylmethacrylate, and polystyrene-polyacrylonitrile. A most preferred copolymer is polyvinylidene-polyacrylonitrile.

Volatile liquids useful in the heat expansion process will also be well known to those skilled in the art and include:aliphatic hydrocarbons such as ethane, ethylene, propane, propene, butane, isobutane, neopentane, acetylene, hexane, heptane; chlorofluorocarbons such as $CCl_3F$, $CCl_2F_2$, $CClF_3$, $CClF_2-CCl_2F_2$, chloroheptafluorocyclobutane, and 1,2-dichlorohexafluorocyclobutane; tetraalkyl silanes, such as tetramethyl silane, trimethylethyl silane, trimethylisopropyl silane, and trimethyl n-propyl silane; as well as perfluorocarbons, including the perfluorocarbons described above. In general, it is important that the volatile liquid not be a solvent for the polymer or copolymer being utilized. It is also preferred that the volatile liquid have a boiling point that is below the softening point of the involved polymer or co-polymer. Boiling points of various volatile liquids and softening points of various polymers and copolymers will be readily ascertainable to one skilled in the art, and suitable combinations of polymers or copolymers and volatile liquids will be easily apparent to the skilled artisan. By way of guidance, and as one skilled in the art would recognize, generally as the length of the carbon chain of the volatile liquid increases, the boiling point of that liquid increases also. Also, mildly preheating the vesicles in water in the presence of hydrogen peroxide prior to definitive heating and expansion may pre-soften the vesicle to allow expansion to occur more readily.

For example, to produce vesicles from synthetic polymers, vinylidene and acrylonitrile may be copolymerized in a medium of isobutane liquid using one or more of the foregoing modified or unmodified literature procedures, such that isobutane becomes entrapped within the vesicles. When such vesicles are then heated to a temperature of from about 80° C. to about 120° C., the isobutane gas expands, which in turn expands the vesicles. After heat is removed, the expanded polyvinylidene and acrylonitrile copolymer vesicles remain substantially fixed in their expanded position. The resulting low density vesicles are extremely stable both dry and suspended in an aqueous media. Isobutane is utilized herein merely as an illustrative liquid, with the understanding that other liquids which undergo liquid/gas transitions at temperatures useful for the synthesis of these vesicles and formation of the very low density vesicles upon heating can be substituted for isobutane. Similarly, monomers other than vinylidene and acrylonitrile may be employed in preparing the vesicles.

In certain preferred embodiments, the vesicles which are formulated from synthetic polymers and which may be employed in the methods of the present invention are commercially available from Expancel, Nobel Industries (Sundsvall, Sweden), including EXPANCEL 551 DE™ microspheres. The EXPANCEL 551 DE™ microspheres are composed of a copolymer of vinylidene and acrylonitrile which have encapsulated therein isobutane liquid. Such microspheres are sold as a dry composition and are approximately 50 microns in size. The EXPANCEL 551 DE™ microspheres have a specific gravity of only 0.02 to 0.05, which is between one-fiftieth and one-twentieth the density of water.

Included among the methods described in the aforementioned patents for the preparation of protein-based vesicles are methods which involve sonicating a solution of a protein. In preferred form, the starting material may be an aqueous solution of a heat-denaturable, water-soluble biocompatible protein. The encapsulating protein is preferably heat-sensitive so that it can be partially insolubilized by heating during sonication. Suitable heat-sensitive proteins include, for example, albumin, hemoglobin, collagen, and the like. Preferably, the protein is a human protein, with human serum albumin (HSA) being more preferred. HSA is available commercially as a sterile 5% aqueous solution, which is suitable for use in the preparation of protein-based vesicles. Of course, as would be apparent to one of ordinary skill in the art, other concentrations of albumin, as well as other proteins which are heat-denaturable, can be used to prepare the vesicles. Generally speaking, the concentration of HSA can vary and may range from about 0.1 to about 25% by weight, and all combinations and subcombinations of ranges therein. It may be preferable, in connection with certain methods for the preparation of protein-based vesicles, to utilize the protein in the form of a dilute aqueous solution. For albumin, it may be preferred to utilize an aqueous solution containing from about 0.5 to about 7.5% by weight albumin, with concentrations of less than about 5% by weight being preferred, for example, from about 0.5 to about 3% by weight.

The protein-based vesicles may be prepared using equipment which is commercially available. For example, in connection with a feed preparation operation as disclosed, for example, in Cerny, et al., U.S. Pat. No. 4,957,656, stainless steel tanks which are commercially available from Walker Stainless Equipment Co. (New Lisbon, Wis.), and process filters which are commercially available from Millipore (Bedford, Mass.), may be utilized.

The sonication operation may utilize both a heat exchanger and a flow through sonicating vessel, in series. Heat exchanger equipment of this type may be obtained from ITT Standard (Buffalo, N.Y.). The heat exchanger maintains operating temperature for the sonication process, with temperature controls ranging from about 65° C. to about 80° C., depending on the makeup of the media. The vibration frequency of the sonication equipment may vary over a wide range, for example, from about 5 to about 40 kilohertz (kHz), with a majority of the commercially available sonicators operating at about 10 or 20 kHz. Suitable sonicating equipment include, for example, a Sonics & Materials Vibra-Cell, equipped with a flat-tipped sonicator horn, commercially available from Sonics & Materials, Inc. (Danbury, Conn.). The power applied to the sonicator horn can be varied over power settings scaled from 1 to 10 by the manufacturer, as with Sonics & Materials Vibra-Cell Model VL1500. An intermediate power setting, for example, from 5 to 9, can be used. It is preferred that the vibrational frequency and the power supplied be sufficient to produce cavitation in the liquid being sonicated. Feed flow rates may range from about 50 mL/min to about 1000 mL/min, and all combinations and subcombinations of ranges therein. Residence times in the sonication vessel can range from about 1 second to about 4 minutes, and gaseous fluid addition rates may range from about 10 cubic centimeters (cc) per minute to about 100 cc/min, or 5% to 25% of the feed flow rate, and all combinations and subcombinations of ranges therein.

It may be preferable to carry out the sonication in such a manner to produce foaming, and especially intense foaming, of the solution. Generally speaking, intense foaming and aerosolating are important for obtaining a contrast agent having enhanced concentration and stability. To promote foaming, the power input to the sonicator horn may be increased, and the process may be operated under mild pressure, for example, about 1 to about 5 psi. Foaming may be easily detected by the cloudy appearance of the solution, and by the foam produced.

Suitable methods for the preparation of protein-based vesicles may involve physically or chemically altering the protein or protein derivative in aqueous solution to denature or fix the material. For example, protein-based vesicles may be prepared from a 5% aqueous solution of HSA by heating after formation or during formation of the contrast agent via sonication. Chemical alteration may involve chemically denaturing or fixing by binding the protein with a difunctional aldehyde, such as glutaraldehyde. For example, the vesicles may be reacted with 0.25 grams of 50% aqueous glutaraldehyde per gram of protein at pH 4.5 for 6 hours. The unreacted glutaraldehyde may then be washed away from the protein.

The present invention is directed to methods for diagnostic imaging which involve the administration to a patient of a contrast agent, in combination with a renal vasodilator. The renal vasodilator may be administered to the patient before, during, and/or after the administration of the contrast agent. A wide variety of techniques are available for the preparation of lipid and/or vesicle compositions which comprise a bioactive agent, including renal vasodilators. For example, lipid and/or vesicle compositions may be prepared from a mixture of lipid compounds, bioactive agent and gas or gaseous precursor. In this case, lipid and/or vesicle compositions may be prepared as described above in which the compositions also comprise a bioactive agent. Thus, for example, micelles can be prepared in the presence of a bioactive agent. In connection with lipid and/or vesicle compositions which comprise a gas, the preparation can involve, for example, bubbling a gas directly into a mixture of lipid compounds and one or more additional materials. Alternatively, the lipid and/or vesicle compositions may be preformed from lipid compounds and gas or gaseous precursor. In the latter case, the bioactive agent may be then added to the lipid and/or vesicle composition prior to use. For example, an aqueous mixture of liposomes and gas may be prepared to which the bioactive agent may be added and which is agitated to provide the liposome composition. The liposome composition which further comprises a bioactive agent can be readily isolated since the gas and/or bioactive agent filled liposome vesicles generally float to the top of the aqueous solution. Excess bioactive agent can be recovered from the remaining aqueous solution.

As those skilled in the art will recognize, any of the lipid and/or vesicle compositions described herein may be lyophilized for storage, and reconstituted, for example, with an aqueous medium (such as sterile water, phosphate buffered solution, or aqueous saline solution), with the aid of vigorous agitation. To prevent agglutination or fusion of the lipids as a result of lyophilization, it may be useful to include additives which prevent such fusion or agglutination from occurring. Additives which may be useful include sorbitol, mannitol, sodium chloride, glucose, trehalose, polyvinylpyrrolidone and poly(ethylene glycol) (PEG), for example, PEG polymers having a molecular weight of from about 400 to about 10,000, with PEG polymers having molecular weights of about 1000, 3000 (such as PEG3350) and 5000 being preferred. These and other additives are described in the literature, such as in the U.S. Pharmacopeia, USP XXII, NF XVII, The United States Pharmacopeja, The National Formulary, United States Pharmacopeial Convention Inc., 12601 Twinbrook Parkway, Rockville, Md. 20852, the disclosures of which are hereby incorporated herein by reference in their entirety. Lyophilized preparations generally have the advantage of greater shelf life.

As discussed above, the compositions of the present invention, including gas and/or gaseous precursor filled vesicles, are useful as contrast agents for diagnostic imaging, including, for example, ultrasound (US) imaging, computed tomography (Conn.) imaging, including CT angiography (CTA), magnetic resonance (MR) imaging, including magnetic resonance angiography (MRA), nuclear medicine, optical imaging and elastography.

In accordance with the present invention, there are provided methods of imaging one or more regions of a patient, and especially the renal region of a patient. The present invention also provides methods for diagnosing the presence or absence of diseased tissue in a patient, especially the presence or absence of diseased renal tissue. The methods of the present invention involve the administration of a contrast medium in the form, for example, of a lipid and/or vesicle composition, to a patient. A renal vasodilator is also administered to the patient. The patient is scanned using diagnostic imaging including, for example ultrasound imaging, to obtain visible images of an internal region, preferably the renal region of a patient. The methods may also be used to image other internal regions of the patient including, for example, the vasculature. In scanning the renal region, it is possible to include the abdominal aorta. The present methods can also be used in connection with the delivery of a bioactive agent to an internal region of a patient.

With respect to the renal vasodilator which is employed in the methods of the present invention, a wide variety of materials are available which may be suitable for use in the methods of the present invention and which, when administered to a patient, may impart a renal vasodilative effect, that is, dilation of blood vessels in the renal region and in particular, dilation of a renal artery. Preferably, the material is capable of increasing the overall renal blood flow. The material may act directly to increase the renal blood flow, or may be involved in biochemical pathways whereby an increase in renal blood flow is produced. More preferably, the material acts to inhibit angiotensin converting enzyme (ACE).

ACE catalyzes the conversion of the relatively inactive decapeptide angiotensin I to angiotensin II, a potent endogenous vasoconstrictor, and the destruction of bradykinin, a potent vasodilator. *The Pharnmacological Basis of Therapeutics*, Hardman, Joel G. And Limbird, Lee E., eds. in chief, 1996, McGraw-Hill, New York, N.Y., pp. 743–751. In patients with renal artery stenosis, blood flow into the kidney is reduced. The kidney with reduced blood flow produces renin, which increases blood pressure in order to improve blood flow into the kidney. The increased blood pressure results from the action of renin on a plasma globulin substrate in the vascular circulation. Angiotensin I is produced in this interaction, and is hydrolyzed by ACEE to Angiotensin II. The administration of ACE inhibitors results in a vasodilator effect, particularly in the kidney, since the renal vessels are particularly sensitive to the vasoconstrictor effects of Angiotensin II.

ACE inhibitors may be grouped according to their chemical structures. Sulfhydryl-containing ACE inhibitors include captopril (1-(3-mercapto-2-methyl-1-oxopropyl)-L-proline), fentiapril (2-(2-hydroxyphenyl)3-(mercapto-1-oxopropyl)-4-thiazodinecarboxylic acid), pivalopril (N-cyclopentyl-N-[3-[2,2-dimethyl-1-oxopropyl)thio]-2-methyl-1-oxopropyl]-(S)-glycine), zofenopril,(1-[3-(benzoylthio)-2-methyl-1-oxopropyl]-4-phenylthio)-hydroxy-2,2-dimethyl-4-(2-oxo-1-[pyrrolidinyl)-2H-1-benzopyran-6-carbonitrile L-proline) , and alacepril ((S)-N-[1-[3-(acetylthio)-2-methyl-1-oxopropyl]L-prolyl]-L-phenylalanine). Dicarboxyl-containing ACE inhibitors include enalapril (1-[N-[1-(ethoxycarbonyl)-3-phenylpropyl]-L-alanyl]L-proline), enalaprilat (the parent dicarboxylic acid of enalapril), lisinopril ((S)-1-[$N^2$-(1-carboxy-3-phenylpropyl)-L-lysyl]-L proline dihydrate), benazepril (3-[[1-ethoxy-carbonyl)-3-phenyl-(1S)propyl]amino]-2,3,4,5-tetrahydro-2-oxo-1H-1-(3S)benzazepine-1-acetic acid), quinapril (3S-[2[R*(R*)],3R*]]-2-[2-[[1-ethoxycarbonyl)-3-phenylpropyl]amino]- 1-oxopropyl]-1,2, 3,4-tetrahydro-3-isoquinolinecarboxylic acid), moexipril (2-[[1-ethoxycarbonyl)-3-phenylpropyl]amino]-1-oxopropyl]-1,2,3,4-tetrahydro-6,7-dimethoxy-3-isoquinolinecarboxylic acid [3S-[2R*(R*)], 3R*]]-), ramipril (2S-[1[R*(R*)],2α, 3aβ,6aβ]]-1-[2-[[1-(ethoxycarbonyl)-3-phenylpropyl] amino]1-oxopropyl]octahydrocyclopenta[b]pyrrole-2-carboxylic acid), spirapril (mixture of 7-[2-[[1-ethoxycarbonyl)-3-phenylprolpyl]amino]-1-oxopropyl]-1H-indole-2-carboxylic acid, [8S-[7[R*(R*),8R*]]-1H-indole-2-carboxylic acid, with 3-[2-4-(4-fluorobenzoyl)-1-piperidinyl]ethyl]-2,4(1H,3H)-quinazolinedione), perindopril (2S-[1-[R*,(R*)],2α,3aβ,7aβ]]-1-[2[[1-(ethoxycarbonyl)butyl]amino]-1-oxopropyl]octahydro-1H-indole-2-carboxylic acid), indolapril (1-[2-[[1-(ethoxycarbonyl)-3-phenylpropyl]amino]-1-oxopropyl] octahydro-1H-indole-2-carboxylic acid,[2S-[1[R*(R*)], 2.alpha., 3a.beta., 7a.beta.]], indalapril ((S)-N-(2,3-dihydro-1H-inden-2yl)-N-[N-{1-ethoxycarbonyl)-3-phenylpropyl]-L-alanyl]glycine, and cilazapril (1S-[[1α,9α(R*)]]-9-[[1-ethoxycarbonyl)-3-phenylpropyl]amino]octahydro-10-oxo-6H-pyridazino[1,2-a][1,2]diazepine-1-carboxylic acid monohydrate). Phosphorous-containing ACE inhibitors include fosinopril ((2α,4β)4-cyclohexyl-1-[[[-2-methyl-1-(1-oxopropoxy)propoxyl](4-phenylbuityl)phosphinyl] acetyl]-L-proline). Such compounds are described, for example, in *The Pharnacological Basis of Therapeutics*, Hardman, Joel G. And Limbird, Lee E., eds. in chief, 1996, McGraw-Hill, New York, N.Y., pp. 743–751, and in *The Merck Index*, Eleventh Ed., 1989, Merck & Co., the disclosures of which are hereby incorporated by reference in their entirety. These as well as other suitable vasodilator compounds will be readily apparent to those skilled in the art once armed with the present disclosure. Pharmaceutically acceptable salts of any of the ACE inhibitors may be used, provided the delivery, efficacy and bioavailability of the inhibitor is not unduly compromised. Preferred for use in the method of the present invention are captopril and enalapril. Captopril is preferred for oral administration and the preferred oral dosage from about 25 milligrams to about 50 milligrams, depending upon patient body weight, about 0.5 to about 5 hours , preferably about 1 to about 2 hours before scanning the patient. Enalapril is preferred for intravenous administration. Generally enalapril is injected from about 15 minutes to about 2 hours before scanning the patient.

If desired, the lipid, protein, polymer and/or vesicle compositions described herein may further comprise a targeting agent to promote targeting of tissues and/or receptors in vivo including, for example, renal tissue. Suitable targeting agents, methods for their incorporation into lipid and/or vesicle compositions, and methods for the use of such targeted compositions, are described, for example, in copending U.S. application Ser. No. 08/640,464, filed May 1, 1996 and U.S. application Ser. No. 08/660,032, filed Jun. 6, 1996, the disclosures of which are hereby incorporated herein by reference, in their entirety.

As one skilled in the art would recognize, administration of the lipid and/or vesicle compositions described herein, as well as the renal vasodilators, can be carried out in various fashions, including parenterally, orally, or intraperitoneally. Parenteral administration, which is preferred, includes administration by the following routes: intravenous; intramuscular; interstitially; intra-arterially; subcutaneous; intraocular; intrasynovial; transepithelial, including transdermal; pulmonary via inhalation; ophthalmic; sublingual and buccal; topically, including ophthalmic; dermal; ocular; rectal; and nasal inhalation via insufflation. Intravenous administration is preferred among the routes of parenteral administration. Various combinations of the lipid and/or vesicle compositions, and renal vasodilators, may be used to alter properties as desired, including viscosity, osmolarity or palatability. In carrying out the imaging methods of the present invention, the contrast medium, including renal vasodilator, can be used alone, or in combination with additional diagnostic, therapeutic or other agents. Such other agents include excipients such as flavoring or coloring materials.

CT imaging techniques which are employed are conventional and are described, for example, in *Computed Body Tomography*, Lee, J. K. T., Sagel, S. S., and Stanley, R. J., eds., 1983, Ravens Press, New York, N.Y., especially the first two chapters thereof entitled *"Physical Principles and Instrumentation"*, Ter-Pogossian, M. M., and "Techniques", Aronberg, D. J., the disclosures of which are incorporated by reference herein in their entirety.

Magnetic resonance imaging techniques, particularly directed to imaging of the renal region, are described in, for example, Brown et al., "Magnetic Resonance Imaging of the Adrenal Gland and Kidney", *Topics in Magnetic Resonance Imaging*, Vol. 7(2), pp. 90–101 (1995); Krestin, "Magnetic Resonance Imaging of the Kidneys: Current Status", *Magnetic Resonance Quarterly*, Vol. 10(1), pp. 2–21 (March 1994); Lee, "Recent Advances in Magnetic Resonance Imaging of Renal Masses", *Canadian Association of Radiologists Journal*, Vol. 42(3), pp. 185–9 (June 1991); Lubat et al., "Magnetic Resonance Imaging of the Kidneys and Adrenals", Vol. 2(3), pp. 17–36 (June 1990); Baumgartner et al., "Magnetic Resonance Imaging of the Kidneys and Adrenal Glands", *Seminars in Ultrasound, CT and MR*, Vol. 10(1), pp. 43–62 (February 1989); Choyke et al., "The Role of MRI in Diseases of the Kidney", *Radiologic Clinics of north America* Vol. 26(3), pp. 617–31 (May 1988); and Papanicolaou et al., "Magnetic Resonance Imaging of the Kidney", *Urologic Radiology*, Vol. 8(3), pp. 139–50 (1986).

With respect to ultrasound, ultrasonic imaging techniques, including second harmonic imaging, and gated imaging, are well known in the art, and are described, for example, in Uhlendorf, "Physics of Ultrasound Contrast Imaging: Scattering in the Linear Range", *IEEE Transactions on Ultrasonics, Ferroelectrics, and Frequency Control*, Vol. 14(1), pp. 70–79 (1994) and Sutherland, et al., "Color Doppler Myocardial Imaging: A New Technique for the Assessment of Myocardial Function", *Journal of the American Society of I,chocardiography*, Vol. 7(5), pp. 441–458 (1994), the disclosures of which are hereby incorporated herein by reference in their entirety.

In the case of diagnostic applications, such as ultrasound, CT and MRI, energy, such as ultrasonic energy, may be applied to at least a portion of the patient to image the target tissue. A visible image of an internal region of the patient, preferably the renal region, may be then obtained, such that the presence or absence of diseased tissue can be ascertained.

Ultrasound can be used for both diagnostic and therapeutic purposes. In diagnostic ultrasound, ultrasound waves or a train of pulses of ultrasound may be applied with a transducer. The ultrasound is generally pulsed (intermittent) rather than continuous, although it may be continuous, if desired. Thus, diagnostic ultrasound generally involves the application of a pulse of echoes, after which, during a listening period, the ultrasound transducer receives reflected signals. Harmonics, ultraharmonics or subharmonics may be used. The second harmonic mode may be beneficially employed, in which the 2x frequency may be received, where x is the incidental frequency. This may serve to decrease the signal from the background material and enhance the signal from the transducer using the contrast media of the present invention which may be targeted to the desired site. Other harmonics signals, such as odd harmonics signals, for example, 3x or 5x, may be similarly received using this method. Subharmonic signals, for example, x/2 and x/3, may also be received and processed so as to form an image.

In addition to the pulsed method, continuous wave ultrasound, for example, Power Doppler, may be applied. This may be particularly useful where rigid vesicles, for example, vesicles formulated from polymethyl methacrylate or cyanomethacrylate, are employed. In this case, the relatively higher energy of the Power Doppler may be made to resonate the vesicles and thereby promote their rupture. This can create acoustic emissions which may be in the subharmonic or ultraharmonic range or, in some cases, in the same frequency as the applied ultrasound. It is contemplated that there may be a spectrum of acoustic signatures released in this process and the transducer so employed may receive the acoustic emissions to detect, for example, the presence of a clot. In addition, the process of vesicle rupture may be employed to transfer kinetic energy to the surface, for example of a clot to promote clot lysis. Thus, therapeutic thrombolysis may be achieved during a combination of diagnostic and therapeutic ultrasound. Spectral Doppler may also be employed. In general, the levels of energy from diagnostic ultrasound are insufficient to promote the rupture of vesicles and to facilitate release and cellular uptake of bioactive agents. As noted above, diagnostic ultrasound may involve the application of one or more pulses of sound. Pauses between pulses permits the reflected sonic signals to be received and analyzed. The limited number of pulses used in diagnostic ultrasound limits the effective energy which is delivered to the tissue that is being studied.

Higher energy ultrasound, for example, ultrasound which is generated by therapeutic ultrasound equipment, is generally capable of causing rupture of the vesicle species. In general, devices for therapeutic ultrasound employ from about 10 to about 100% duty cycles, depending on the area of tissue to be treated with the ultrasound. Areas of the body which are generally characterized by larger amounts of muscle mass, for example, backs and thighs, as well as highly vascularized tissues, such as cardiovascular tissue, may require a larger duty cycle, for example, up to about 100%.

In therapeutic ultrasound, continuous wave ultrasound is used to deliver higher energy levels. For the rupture of vesicles, continuous wave ultrasound is preferred, although the sound energy may be pulsed also. If pulsed sound energy is used, the sound will generally be pulsed in echo train lengths of from about 8 to about 20 or more pulses at a time. Preferably, the echo train lengths are about 20 pulses at a time. In addition, the frequency of the sound used may vary from about 0.025 to about 100 megahertz (MHZ). In general, frequency for therapeutic ultrasound preferably ranges between about 0.75 and about 3 MHZ, with from about 1 and about 2 MHZ being more preferred. In addition, energy levels may vary from about 0.5 Watt (W) per square centimeter (cm$^2$) to about 5.0 W/cm$^2$, with energy levels of from about 0.5 to about 2.5 W/cm$^2$ being preferred. Energy levels for therapeutic ultrasound involving hyperthermia are generally from about 5 W/cm$^2$ to about 50 W/cm$^2$. For very small vesicles, for example, vesicles having a diameter of less than about 0.5 μm, higher frequencies of sound are generally preferred. This is because smaller vesicles may be capable of absorbing sonic energy more effectively at higher frequencies of sound. When very high frequencies are used, for example, greater than about 10 MHZ, the sonic energy may penetrate fluids and tissues to a limited depth only. Thus, external application of the sonic energy may be suitable for skin and other superficial tissues. However, it is generally necessary for deep structures to focus the ultrasonic energy so that it is preferentially directed within a focal zone. Alternatively, the ultrasonic energy may be applied via interstitial probes, intravascular ultrasound catheters or endoluminal catheters. Such probes or catheters may be used, for example, in the esophagus for the diagnosis and/or treatment of esophageal carcinoma. In addition to the therapeutic uses discussed above, the compositions described herein can be employed in connection with esophageal carcinoma or in the coronary arteries for the treatment of atherosclerosis, as well as the therapeutic uses described, for example, in U.S. Pat. No. 5,149,319, the disclosures of which are hereby incorporated herein by reference, in their entirety.

A therapeutic ultrasound device may be used which employs two frequencies of ultrasound. The first frequency may be defined as x, and the second frequency may be defined as 2x. In preferred form, the device would be designed such that the focal zones of the first and second frequencies converge to a single focal zone. The focal zone of the device may then be directed to the compositions, for example, vesicle compositions, within the tissue in the region of interest. This ultrasound device may provide second harmonic therapy with simultaneous application of the x and 2x frequencies of ultrasound energy. It is contemplated that, in the case of ultrasound involving vesicles, this second harmonic therapy may provide improved rupturing of vesicles as compared to ultrasound energy involving a single frequency. Also, it is contemplated that the preferred frequency range may reside within the fundamental harmonic frequencies of the vesicles. Lower energy may also be used with this device. An ultrasound device which may be employed in connection with the aforementioned second harmonic therapy is described, for example, in Kawabata, K. et al., *Ultrasonics Sonochemistry*, Vol. 3, pp. 1–5 (1996), the disclosures of which are hereby incorporated herein by reference, in their entirety.

In the case of vesicle compositions formulated from lipids, the concentration of lipid required to form a desired stabilized vesicle level may vary depending, for example, upon the type of lipid used, and may be readily determined by routine experimentation. For example, in preferred embodiments, the concentration of 1,2-dipalmitoylphosphatidylcholine (DPPC) used to form stabilized vesicles according to the methods of the present invention may be from about 0.1 mg/mL to about 30 mg/mL of saline solution, more preferably from about 0.5 mg/mL to about 20 mg/mL of saline solution, and even more preferably from about 1 mg/mL to about 10 mg/mL of saline solution. The concentration of distearoylphosphatidylcholine (DSPC) used in preferred embodiments may be from about 0.1 mg/mL to about 30 mg/mL of saline solution, more preferably from about 0.5 mg/mL to about 20 mg/mL of saline solution, and even more preferably from about 1 mg/mL to about 10 mg/mL of saline solution.

The useful dosage of contrast agent and/or renal vasodilator to be administered, and the particular mode of administration, may vary depending upon the age, weight and the particular mammal and region thereof to be scanned, and the particular contrast medium and/or renal vasodilator to be employed. Typically, the dosage may be initiated at lower levels and increased until the desired contrast enhancement or other effect is achieved. With respect to the contrast agent, the IV dose may be less than about 10 mL for a 70 Kg patient, with lower doses being preferred. The dosage of the renal vasodilator may vary, for example from about 0.01 to about 100 mg/Kg, or from about 0.4 mg to about 10 g or higher. In preferred embodiments which involve the administration of compositions that comprise DPPC, DPPE and DPPE PEG-5000, in combination with a renal vasodilator, the renal vasodilator is preferably administered to the patient at a dosage of from about 0.01 to about 30 mg/mL, preferably from about 0.01 mg/mL to about 1 mg/mL, more preferably from about 0.0 1 mg/mL to about 0.1 mg/mL.

The compositions described herein, and especially the vesicle compositions, are useful as contrast media in diagnostic imaging, and may also be suitable for use in all areas where diagnostic imaging is employed. However, the stabilized vesicles are particularly useful for perfusion imaging.

In accordance with the present invention, there are provided methods of imaging a patient generally, preferably the renal region, and/or of specifically diagnosing the presence of diseased tissue in a patient, especially the renal region. The imaging process of the present invention may be carried out by administering a contrast agent and a renal vasodilator to a patient, and then scanning the patient using, for example, ultrasound, computed tomography, and/or magnetic resonance imaging, to obtain visible images of an internal region of a patient and/or of any diseased tissue in that region. The methods may be particularly useful in providing images of the renal region, but can also be employed more broadly, such as in imaging the vasculature or the gastrointestinal region, or in other ways as will be readily apparent to those skilled in the art. The patient can be any type of mammal, but most preferably is a human.

The present invention also provides methods of diagnosing the presence of diseased tissue in a patient, especially diseased tissue in the cardiovasculature. Diseased tissue includes, for example, endothelial tissue which results from vasculature that supports diseased tissue. As a result, the localization and visualization of endothelial tissue to a region of a patient which under normal circumstances is not associated with endothelial tissue provides an indication of diseased tissue in the region. In addition, the methods of the present invention may be used for diagnosing the presence or absence of renal artery disease, including, for example, renal arterial stenosis. Other diseases of the cardiovasculature which may be imaged and/or diagnosed with the methods of the present invention would be readily apparent to one of ordinary skill in the art, once armed with the present disclosure.

As noted above, administration of the compositions described herein may be carried out in various fashions, such as intravascularly, orally, rectally, and the like, using a variety of dosage forms. When the region to be scanned is the cardiovascular region, administration of the contrast medium is preferably carried out intravascularly including, for example, intravenously. When the region to be scanned is the renal region, administration of the contrast medium is preferably carried out orally or intravascularly. When the region to be scanned is the gastrointestinal region, administration of the contrast medium is preferably carried out orally or rectally. Administration of the renal vasodilator may also be carried out in various fashions, such as intravascularly or orally, depending on the particular renal vasodilator employed. For example, nitrovasodilators, such as nitroglycerin, may be administered IV, as well as transdermally. The appropriate mode or modes of administration of the renal vasodilator would be readily apparent to one of ordinary skill in the art, once armed with the present disclosure. Administration may be continuous (constant), or intermittent (e.g., pulsed), as desired, for example by continuous intravenous infusion or by intermittent intravenous infusion.

Various combinations of the lipid, protein, polymer and/or vesicle compositions may be used to modify the relaxation behavior of the medium or to alter properties such as the viscosity, osmolarity or palatability (in the case of orally administered materials).

The echogenicity of vesicles, and especially, gas filled vesicles, and the ability to rupture vesicles at the peak resonant frequency using ultrasound, permits the controlled delivery of bioactive agents to an internal region of a patient. Specifically, the vesicles may be monitored subsequent to their administration to a patient to determine the rate at which the vesicles arrive, for example, to a desired region. Furthermore, the vesicles may be ruptured using ultrasound to release a bioactive agent in the region.

In accordance with the present invention, there are also provided methods for measuring blood flow in the renal region of a patient. In accordance with this aspect of the invention, there are provided certain embodiments which may involve first applying to the region of interest a substantial pulse of ultrasonic energy, for example, an ultrasonic energy pulse of up to about 0.5 W/cm$^2$, preferably about 0.1 W/cm$^2$, to provide a "square wave" of energy. This square wave energy may provide substantial reflectivity and, therefore, substantial brightness in the ultrasound image. As the square wave energy becomes diluted in the bloodstream, the brightness of the corresponding ultrasound image similarly decreases. Observation and analysis of the rate that the square wave energy becomes diluted may provide an indication of the rate of renal blood flow.

In another embodiment of a method for measuring blood flow in the renal region of a patient, there are provided herein methods which generally involve the administration to a patient of a contrast agent in such a manner as to maintain the concentration of contrast agent in the renal region at about a constant level. This may be achieved by using any of a variety of methods including, for example, a constant intravenous injection of contrast agent.

In preferred embodiments of the present invention, the lipid and/or vesicle compositions may be administered by syringe, that is, by intravenous (IV) injection. Accordingly, the gas and/or vesicle administration rates provided herein generally correspond to injection rates. As would be apparent to one of ordinary skill in the art, once armed with the present disclosure, the location on the body of the patient at which the lipid and/or vesicle compositions are injected may vary and depends upon a variety of factors, including, for example, the particular lipid and/or vesicle composition employed, the contemplated application, such as diagnostic or therapeutic application, and the particular region of interest. For example, in the case of diagnostic ultrasound of myocardial tissue, the lipid and/or vesicle compositions may be injected intravenously (IV), for example, in the arm of a patient.

The IV administration of the contrast agents described herein including, for example, the vesicle compositions, may involve administration via syringe. This may be achieved, for example, by an appropriate medical technician who handles the syringe or syringes manually. Alternatively, administration may be achieved mechanically, for example, by using a constant infusion device, such as a mechanical injector which operates using pneumatic or hydraulic pressure. Suitable mechanical injectors which may be used in the methods of the present invention include a Syringe Pump Model 351, commercially available from Sage Instruments (a division of Orion Research Inc., Boston, Mass.), a MedRad™ power injector, commercially available from Medrad, Inc. (Pittsburgh, Pa.) or a Liebel Flarsheim, commercially available from Liebel Flarsheim Co. (Cincinnati, Ohio.). Preferably, the contrast agent is administered for a period of time of at least about 1 second, more preferably from about 5 seconds up to about 30 seconds or longer, depending, for example, upon the particular contrast agent employed, the volume of injection, and the like. In the case of contrast agents based on vesicles, the time period of administration may also depend, for example, on the concentration of vesicles in the contrast agent, the size of the vesicles and the distribution of vesicle size in the contrast agent. Scanning the renal region with diagnostic imaging such as, for example, ultrasound imaging, provides a diagnostic image of the renal region. By maintaining the concentration of contrast agent in the renal region substantially constant, there may desirably be provided a substantially constant level of brightness in this diagnostic image. Subsequent administration to the patient of a renal vasodilator may then increase the renal blood flow which, as discussed above, may also increase the concentration of contrast agent in the renal tissue.

The images obtained through imaging, such as ultrasonic imaging, may be analyzed qualitatively, but preferably quantitative techniques are used. The videodensitometry signal may be digitized and analyzed to determine changes in signal intensity. Various comparative measurements may be made. For example, comparison of videodensitometry from two kidneys may be compared to determine whether one kidney exhibits a relatively lower videodensitometric response, indicating the likely presence of renal artery hypertension in one kidney. Alternatively, the videodensitometry from one or both kidneys may be compared with that of the abdominal aorta. Using the videodensitometry from the aorta as a baseline, it is possible to compare the relative enhancement in the kidneys in a patient thought to have renal hypertension with an age-adjusted standard enhancement for a normal patient, which may provide an indication of the extent of any renal stenosis. Subtractive methods may be used, for example, for comparing two kidneys in the same patient or for comparing the videodensitometry before contrast enhancement by administration of contrast agent with the videodensitometry after contrast enhancement.

For the purposes of the methods described in accordance with the present embodiment, it is understood that the concentration of vesicles is about proportional to the brightness of a diagnostic image, particularly an ultrasound image, which in turn is about proportional to the rate of blood flow in the renal region. Also for the purposes of the methods described in the present embodiment, it is understood that the vesicles preferably follow a first order rate of elimination. However, other order rates, such as zero, second or third order rates, may be applicable also to these methods. With these understandings, there may be obtained an indication of the percent increase in renal flow provided by the renal vasodilator by using a simple derivation:

$$-d[\text{vesicles}]/dT = k[\text{vesicles}]$$

where

[vesicles]=concentration of vesicles;
k=rate constant as a first order process ($\sec^{-1}$); and
T=time (seconds).

With the understanding also that there is preferably a correlation between vesicle concentration, videodensitometry and renal blood flow, which correlation may be defined, for example, by a correlation constant k, then:

$$-d[\text{vesicles}]/dT = k[\text{vesicles}] = -d[\text{videodensitometry}]/dT = k[\text{videodensitometry}]$$

where

[videodensitometty]=video brightness in videodensitometry units (VDU's ).

Rearranging the above equation yields the following:

$$-d[\text{videodensitometry}]/[\text{videodensitometry}] = kdT$$

Thus, $$-\int d[\text{videodensitometry}]/[\text{videodensitometry}] = \int kdT$$

or $$\ln[\text{videodensitometry}_{t=0} - \text{videodensitometry}_t] = kT$$

Expansion of the foregoing equation yields:

$$[\text{videodensitometry}_t] = [\text{videodensitometry}_{t=0}] e^{-kT}$$

With the measurement of a baseline videodensitometry at time t=0 which, in the present embodiment, refers to the videodensity of a diagnostic image of the renal region with a constant infusion of contrast agent, and the final videodensitometry at time T=t which, in the present embodiment, refers to the videodensity of a diagnostic image of the renal region after administration of a renal vasodilator, a rate constant for the increase in renal flow at a given dosage of renal vasodilator may be determined.

With the understanding that the blood flow in the renal region is about proportional to videodensitometry, then substitution yields:

$$[\text{flow}_t] = [\text{flow}_{t=0}] e^{-kT}$$

Thus, the relative increase (%) in renal blood flow may be determined by employing a constant administration of contrast agent and once armed with the knowledge of the change in brightness of renal tissue in ultrasonic imaging after administration of a renal vasodilator. Variations in correlation between flow, videodensitometry, and microbubble concentration per unit time which may occur may affect the accuracy of the determinations of increases in renal blood flow. However, corrections to any non-linearity or non-proportionality may be incorporated into the calculations. For example, corrections for variations between vesicle concentration and image quantitation may be provided, for example, by employing the techniques described in Eriksen, M., "Tissue Echo Intensity and Blood Attenuation Changes—The Pitfalls of Video Densitometry", *The Second Annual International Symposium on Contrast Agents in Diagnostic Ultrasound*, Atlantic City, N.J. (May 7, 1996). Calibration techniques may be used to improve the accuracy of the correlation of densitometry data with blood flow.

For example, an internal calibration method such as that described in Mor-Avi, V. Et. Al, *Ultrasound in Medicine and Biology* 19(8), pp. 619–33 (1993) for use in calculating myocardial blood flow may be adapted for use in the renal region. Inaccuracies may remain due to non-linearity at relatively high concentrations of contrast agent. Alternatively, an external calibration method may be used to determine the relationship between videodensity and volume of contrast agent in a model system. Images obtained by scanning a patient using the calibrated contrast agent may be processed to calculate blood flow rates based on the model system. With an external calibration technique, corrections may be made to compensate for non-linearities in acoustic response at higher concentrations of contrast agent and differences in rheological properties between the contrast agent and the red blood cells in the patient.

The following examples are merely illustrative of the present invention and should not be considered as limiting the scope of the invention in any way. Examples 1 and 2 are actual examples, and Examples 3 and 4 are prophetic.

EXAMPLES

Example 1

This example describes the preparation of a lipid vesicle composition for use in the methods of the present invention. "DPPC" refers to dipalmitoylphosphatidylcholine; "DPPE" refers to dipalmitoylphosphatidylethanolamine; and "DPPA" refers to dipalmitolylphosphatidic acid. "PEG5000" refers to poly(ethylene glycol) polymer having a molecular weight of about 5000. "DPPE-PEG5000" refers to DPPE which is covalently bound to PEG5000, wherein the DPPE and PEG5000 are present in a weight ratio of about 20:80. "PFP" refers to perfluoropropane gas.

To a solution of saline, propylene glycol and glycerol (8:1:1) were added DPPC, DPPE-PEG5000 and DPPA in a molar ratio of 82:8:10. The resulting mixture was heated to about 45° C. and filtered (0.22 $\mu$m). The filtered mixture was placed in a vial and allowed to cool to room temperature. The vial was placed under vacuum to evacuate any gas, after which the vial was pressurized with PFP. The vial was then sealed, placed on a shaker and agitated at room temperature to provide a solution of PFP-filled vesicles having a mean diameter of about 2.5 $\mu$m. The concentration of vesicles in the solution was about $1.5 \times 10^9$ vesicles/mL.

Example 2

This example describes the use of vesicles prepared according to Example 1 in the imaging of kidneys in a mammal to detect an occluded kidney.

An 18 kg female mongrel dog was anaesthetized using halothane ($C_2HBrClF_3$). The renal artery leading to the left kidney was exposed to a 2 mm pneumatic occluder (Invivometric, Healdsburg, Calif.) and a Doppler flow probe (Transonic, Ithaca, N.Y.) was attached.

The abdomen was closed with sutures and ultrasound imaging was carried out using an Acoustic Imaging 5200S ultrasound machine with a 7.5 Mhz tightly curved linear array transducer (Acoustic Imaging, Phoenix, Ariz.) transabdominally. The pneumatic occluder was inflated until the flow rate was reduced from 44 ml/min to 22 ml/min. Vesicles prepared according to Example 1 were injected at a dose of 0.02 cc/kg ($3.0 \times 10^7$ vesicles/kg) through a catheter in the cephalic vein and imaging of the left (occluded) kidney was carried out. This procedure was then repeated on the right (unoccluded) kidney. The left renal artery was occluded during imaging of the unoccluded kidney. A dose of 330 microliters (μL) of enalapril (1.25 mg/mL)(Vasotec, Merck, Sharp and Dohme, West Point, Pa.) was administered through the cephalic catheter. The enalapril was given 30 minutes to act, and then the pneumatic occluder was reinflated to reduce the flow to 22 mL/min. An additional dose of 0.02 cc/kg ($3.0 \times 10^7$ vesicles/kg) of vesicles was administered for each kidney and imaging was performed. Continuous fundamental ultrasound imaging was performed over a period of four minutes after each injection of vesicles. A period of ten minutes was allowed between each injection to allow for clearance of the vesicles from the renal region.

The images were then captured using a Panasonic SV 3350 SVHS VCR (Japan) and a Macintosh Centris 660AV computer (Apple Computer, Cupertino, Calif.). The captured images were analyzed using Image 1.55, an image analysis software package distributed by the NiH (Bethesda, Md.). Regions of interest were selected from the occluded kidney before the administration of enalapril ("pre-enalapril") and after the administration of enalapril ("post-enalapril") and from the unoccluded kidney pre-enalapril and post- enalapril. The data is shown in the table below. A decrease in the videodensitometry (indicated by a negative number) means that the image became darker, and an increase indicates an increase in brightness. The term "pre-contrast" indicates a videodensitometry measurement taken prior to the administration of the vesicles. The term "post contrast" indicates a videodensitometry measurement taken following the administration of the vesicles. Data is presented as the result of the indicated subtractions. For example, [precontrast—post contrast] represents the subtraction of the videodensitometry measurement following administration of the vesicles from the videodensitometry measurement prior to the administration of the vesicles. "Pre enalapril" means before the administration of enalapril. "Post enalapril" means following the administration of enalapril.

| Treatment | Change in Videodensitometry measurement |
| --- | --- |
| [Precontrast - post contrast], pre enalapril, Occluded Kidney | 11.84 |
| [Precontrast - post contrast], post enalapril, Occluded Kidney | 8.59 |
| Occluded Kidney [pre Enalapril - post enalapril] | -3.25 |
| [Precontrast - post contrast], pre enalapril, Unoccluded Kidney | 31.74 |
| [Precontrast - post contrast], post enalapril, Unoccluded Kidney | 49.20 |
| [pre Enalapril - post enalapril], Unoccluded Kidney | 17.46 |

As can be seen in the above data, there is a measurable increase in brightness in the unoccluded kidney after the administration of enalapril. In the occluded kidney, however, the measurements remain quite constant.

Example 3

This example describes the use of vesicles prepared according to Example 1 in ultrasonic imaging to measure renal blood flow in a mammal.

A 20 kg dog is anesthetized using Halothane. The renal artery is exposed to a 2 mm pneumatic occluder as in Example 2, and a Doppler flow probe is attached to the renal artery in the same manner as in Example 2. Vesicles prepared according to Example 1 ($6 \times 10^7$ vesicles/cc in saline) are preheated to 37° C., then are continuously injected at a rate of 1 cc/minute, through a catheter in the cephalic vein.

Pulsed ultrasound imaging is performed on the kidney, using a Hewlett Packard ultrasound machine (Hewlett Packard, Boston, Mass.). Continuous second harmonic imaging is used, with transmittance at 2 MHZ and receiving at 5 MHZ. A pulse having an energy of 1.0 Watts/cm$^2$ is then applied intermittently to rupture the vesicles. The Example is repeated 5 times, with varying time intervals (1, 2, 3, 4, and 5 seconds, respectively) allowed between each rupturing pulse.

Videodensitometry is performed on the subject. The reappearance of the videodensity signal following a rupturing pulse, designated "B", is obtained. The signal directly correlates with renal blood flow (correlation constant r=0.88–0.98). Normalized videodensitometry signals (y) is calculated using the formula $y=A(1-10^{-B/A})$, where A is the peak video density and directly correlates with the quantity of blood in the renal tissue, and t is the time interval between imaging pulse and rupturing pulse.

The data are plotted in FIG. 1. "A" represents the peak, or maximum, videodensity, which occurs when the flow of blood had delivered to the renal tissue the maximum quantity of vesicles, thus generating the maximum videodensity signal. Following a rupturing pulse, the vesicles burst and the signal drops. As the blood flow delivers vesicles again, the videodensity signal reappears. "B" represents the reappearance of the videodensity signal. The higher the signal, the more vesicles are in the region, and correspondingly, the higher the blood flow rate. As more vesicles are carried into the region, the signal B increases.

The signal is represented in the figure as a ratio of the reappearing videodensity signal B, to the peak videodensity signal, A, i.e., (B/A). The higher the rate of blood flow, the higher the ratio (B/A) is for a given normalized videodensity. Therefore, it is expected that (B/A) will increase more rapidly in the absence of occlusion.

The normalized videodensity values (y) are on the y axis, and the ratio of reappearance of videodensity B to peak videodensity A (B/A) is on the x axis. Each plot represents a different time interval (1 through 5 seconds) following the rupturing pulse. The data illustrate the ability to quantitatively measure blood flow using pulsed ultrasound imaging and continuous administration of a renal vasodilator.

Example 4

This example illustrates the use of intermittent ultrasonic imaging with a renal vasodilator to measure blood flow through the kidney of a mammal having a stenotic renal artery.

The same procedure is carried out as in Example 3, except that a 20 kg dog with a stenotic renal artery is used. Ultrasonic imaging is performed as in Example 3. One hour is allowed for the vesicles to be carried from the renal region by blood circulation.

Captopril is administered (10 mg) followed by administration of vesicles. Ultrasonic imaging is again performed as in Example 3.

The disclosures of each patent, patent application and publication cited or described herein are hereby incorporated by reference herein, in their entirety.

Various modifications, in addition to those described herein, will be apparent to those skilled in the art from the foregoing description. Such modifications are also intended to fall within the scope of the appended claims.

What is claimed is:

1. A method for measuring blood flow in the renal region of a patient, comprising:(i) administering to the patient a vesicle composition which comprises lipid, protein or polymer vesicles and a gas or gaseous precursor, (ii) scanning the patient using diagnostic imaging to obtain a visible image of the renal region, (iii) administering to the patient a renal vasodilator, (iv) continuing said scanning, and (v) determining the blood flow from a videodensity versus time relationship in the images obtained in steps (ii) through (iv).

2. A method according to claim 1 wherein said vesicle composition is administered to the patient to maintain a substantially constant concentration of vesicle composition in the renal region.

3. A method according to claim 2 wherein said administration comprises constant administration.

4. A method according to claim 3 comprising administering said vesicle composition using a constant infusion device.

5. A method according to claim 4 wherein said constant infusion device comprises a power injector.

6. A method according to claim 1 wherein said diagnostic imaging is selected from the group consisting of ultrasonic imaging and computed tomography imaging.

7. A method according to claim 6 wherein said diagnostic imaging comprises ultrasonic imaging.

8. A method according to claim 1 wherein said vesicles comprise lipid vesicles.

9. A method according to claim 8 wherein said vesicles comprise vesicles selected from the group consisting of micelles and liposomes.

10. A method according to claim 8 wherein said lipid comprises a phospholipid.

11. A method according to claim 10 wherein said phospholipid is selected from the group consisting of phosphatidylcholine, phosphatidylethanolamine and phosphatidic acid.

12. A method according to claim 10 wherein said phosphatidyl-choline is selected from the group consisting of dioleoylphosphatidylcholine, dimyristoyipllosphatidylcholine, dipalmitoylphosphatidylcholine and distearoylphosphatidylcholine.

13. A method according to claim 12 wherein said phosphatidylcholine comprises dipalmitoylphosphatidylcholine.

14. A method according to claim 11 wherein said phosphatidylethanolamine is selected from the group consisting of dipalmitoylphosphatidylethanolamine, dioleoylphospnatidylethanolamine, N-succinyldioleoylphosphatidylethanolamine and 1-hexadecyl-2-palmitoylglycerophosphoethanolamine.

15. A method according to claim 14 wherein said phosphatidylethanolamine comprises dipalmitoylphosphatidylethanolamine.

16. A method according to claim 11 wherein said phosphatidic acid comprises dipalmitolylphosphatidic acid.

17. A method according to claim 18 wherein said lipid further comprises a polymer.

18. A method according to claim 17 wherein said polymer comprises a hydrophilic polymer.

19. A method according to claim 18 wherein said hydrophilic polymer comprises polyethylene glycol.

20. A method according to claim 1 wherein said vesicles comprise polymer vesicles.

21. A method according to claim 20 wherein said polymer comprises a synthetic polymer or copolymer which is prepared from monomers selected from the group consisting of acrylic acid, methacrylic acid, ethyleneimine, crotonic acid, acrylamide, ethyl acrylate, methyl methacrylate, 2-hydroxyethyl methacrylate, lactic acid, glycolic acid, $\epsilon$-caprolactone, acrolein, cyanoacrylate, cyanomethacrylate, bisphenol A, epichlorhydrin, hydroxyalkylacrylates, siloxane, dimethylsiloxane, ethylene oxide, ethylene glycol, hydroxyalkylmethacrylates, N-substituted acrylamides, N-substituted methacrylamides, N-vinyl-2-pyrrolidone, 2,4-pentadiene-1-of, vinyl acetate, acrylonitrile, styrene, p-amino-styrene, p-aminobenzylstyrene, sodium styrene sulfonate, sodium 2-sulfoxyethyl-methacrylate, vinyl pyridine, aminoethyl methacrylates and 2-methacryloyloxytrimethyl-ammonium chloride.

22. A method according to claim 21 wherein said polymer comprises a synthetic polymer or copolymer selected from the group consisting of polyacrylic acid, polyethyleneimine, polymethacrylic acid, polycyanomethacrylate, polymethylmethacrylate, polysiloxane, polydimethylsiloxane, polylactic acid, poly($\epsilon$-caprolactone), epoxy resin, poly(ethylene oxide), poly(ethylene glycol), polyamide, polyvinylidene-polyacrylonitrile, polyvinylidene-polyacrylonitrile-polymethylmethacrylate and polystyrene-polyacrylonitrile.

23. A method according to claim 22 wherein said polymer comprises polyvinylidene-polyacrylonitrile copolymer.

24. A method according to claim 1 wherein said gas comprises a fluorinated gas.

25. A method according to claim 24 wherein said fluorinated gas is selected from the group consisting of a perfluorocarbon, sulfur hexafluoride and heptafluoropropane.

26. A method according to claim 24 wherein said fluorinated gas comprises a perfluorocarbon.

27. A method according to claim 26 wherein said perfluorocarbon gas is selected from the group consisting of perfluoromethale, perfluoroethane, perfluoropropane, perfluorobutane and perfluorocyclobutane.

28. A method according to claim 1 wherein said gaseous precursor has a boiling point of greater than about 37° C.

29. A method according to claim 28 wherein said gaseous precursor comprises a fluorinated compound.

30. A method according to claim 29 wherein said fluorinated compound comprises a perfluorocarbon.

31. A method according to claim 30 wherein said perfluorocarbon is selected from the group consisting of perfluoropentane, perfluorohexane and perfluoroheptane.

32. A method for measuring blood flow in the renal region of a patient, comprising:(i) administering to the patient a composition which comprises a lipid, protein or polymer and a gas or gaseous precursor, (ii) scanning the patient using diagnostic imaging to obtain a visible image of the renal region, (iii) administering to the patient a renal vasodilator, (iv) continuing said scanning, and (v) determining the blood flow from a videodensity versus time relationship in the images obtained in steps (ii) through (iv).

* * * * *

UNITED STATES PATENT AND TRADEMARK OFFICE
CERTIFICATE OF CORRECTION

PATENT NO. : 5,846,517
DATED : December 8, 1998
INVENTOR(S) : Evan C. Unger

It is certified that error appears in the above-identified patent and that said Letters Patent is hereby corrected as shown below:

On the title page, second column, under "OTHER PUBLICATIONS", at "Desir, et al.", second line thereof, please delete "Myacardial" and insert --Myocardial-- therefor.

On page 3, second column, under "OTHER PUBLICATIONS", at "Hope, et al.", fourth line thereof, please delete "*Acts*" and insert --*Acta*-- therefor.

On page 3, second column, under "OTHER PUBLICATIONS", at "Ten Cate et al.", please delete "Contract" and insert --Contrast-- therefor.

On page 4, first column, under "OTHER PUBLICATIONS", at "Scarpa et al.", third line thereof, please delete "*Acts*" and insert --*Acta*-- therefor.

On page 4, first column, under "OTHER PUBLICATIONS", at "Fukuda et al.", second line thereof, please delete "Diotadecyldimethylammonium" and insert --Dioctadecyldimethylammonium-- therefor.

On page 4, first column, under "OTHER PUBLICATIONS", at "Shiina et al.", please delete "Hyperthermiably" and insert --Hyperthermia by-- therefor.

On page 4, second column, under "OTHER PUBLICATIONS", at "Poznansky et al., please delete "Biologica" and insert --Biological-- therefor.

UNITED STATES PATENT AND TRADEMARK OFFICE
CERTIFICATE OF CORRECTION

PATENT NO. : 5,846,517
DATED : December 8, 1998
INVENTOR(S) : Evan C. Unger

It is certified that error appears in the above-identified patent and that said Letters Patent is hereby corrected as shown below:

On page 4, second column, under "OTHER PUBLICATIONS", at "Simons et al.", please delete "oligunucleotides" and insert --oligonucleotides-- therefor.

On page 5, first column, under "OTHER PUBLICATIONS", at "Brown and Langer", second line thereof, please delete "39:22129" and insert --39:221 29-- therefor.

On page 5, first column, under "OTHER PUBLICATIONS", at "Ter-Pogossian", please delete "*Tomography*, Kee, et al., n".

On page 5, first column, under "OTHER PUBLICATIONS", at "Ter-Pogossian", second line thereof, after "*Computed Body*", please insert --*Tomography*, Lee et al.,-- therefor.

On page 5, first column, under "OTHER PUBLICATIONS", at "Aronberg", please delete "Kee" and insert --Lee-- therefor.

On page 5, first column, under "OTHER PUBLICATIONS", at "Schutt et al.", please delete "Microbuble" and insert --Microbubble-- therefor.

On page 5, first column, under "OTHER PUBLICATIONS", at Frézard, et al.", second line thereof, please delete "Cariers" and insert --Carriers-- therefor.

UNITED STATES PATENT AND TRADEMARK OFFICE
CERTIFICATE OF CORRECTION

PATENT NO. : 5,846,617
DATED : December 8, 1998
INVENTOR(S) : Evan C. Unger

It is certified that error appears in the above-identified patent and that said Letters Patent is hereby corrected as shown below:

On page 5, second column, under "OTHER PUBLICATIONS", at "Keller", second line thereof, please delete "Microbubles" and insert --Microbubbles-- therefor.

On page 5, second column, under "OTHER PUBLICATIONS", at Keller", second line thereof, please delete "Microcirulation" and insert --Microcirculation-- therefor.

On page 5, second column, under "OTHER PUBLICATIONS", at "Wheatley et al.", third line thereof, please delete "Microbubles" and insert --Microbubbles-- therefor.

On page 6, first column, under "OTHER PUBLICATIONS", at "Villanueva et al.", please delete "Patters" and insert --Patterns-- therefor.

On page 6, first column, under "OTHER PUBLICATIONS", at "Villanueva et al.", fourth line thereof, please delete "Salavage" and insert --Salvage-- therefor.

In column 4, line 54, please delete "65, 857-860 (1992)" and insert --65; 857-860 (1992)-- therefor.

In column 10, lines 29-30, after "renal tissue", continue with next sentence, "Generally speaking, . . .".

In column 10, lines 37-38, please delete "videodenistometry" and insert --videodensitometry-- therefor.

UNITED STATES PATENT AND TRADEMARK OFFICE
CERTIFICATE OF CORRECTION

PATENT NO. : 5,846,517
DATED : December 8, 1998
INVENTOR(S) : Evan C. Unger

Page 4 of 8

It is certified that error appears in the above-identified patent and that said Letters Patent is hereby corrected as shown below:

In column 15, line 28, please delete "*lipid Bilayers*" and insert --*Lipid Bilayers*-- therefor.

In column 18, line 16, please delete "thereof Vesicles" and insert --thereof. Vesicles-- therefor.

In column 18, line 57, please delete "thereof Exemplary" and insert --thereof. Exemplary-- therefor.

In column 19, line 3, please delete "thereof Preferred" and insert --thereof. Preferred-- therefor.

In column 20, line 53, please delete "thereof Carbonic" and insert --thereof. Carbonic-- therefor.

In column 21, line 5, please delete "ammomalonate" and insert --aminomalonate-- therefor.

In column 22, line 15, please delete "norbomane" and insert --norbonane-- therefor.

In column 22, line 36, please delete "difluorolodomethane" and insert --difluoroiodomethane-- therefor.

UNITED STATES PATENT AND TRADEMARK OFFICE
CERTIFICATE OF CORRECTION

PATENT NO. : 5,846,517
DATED : December 8, 1998
INVENTOR(S) : Evan C. Unger

It is certified that error appears in the above-identified patent and that said Letters Patent is hereby corrected as shown below:

In column 22, line 56, please delete "2,4-diarninotoluene" and insert --2,4-diaminotoluene-- therefor.

In column 29, lines 22-23, please delete "lauryltrimethylarmronium" and insert --lauryltrimethylammonium-- therefor.

In column 29, line 62, please delete "steanic" and insert --stearic-- therefor.

In column 30, line 42, please delete "Fe(II)" and insert --Fe(III)-- therefor.

In column 31, line 28, please delete "paramagnefic" and insert --paramagnetic-- therefor.

In column 35, line 12, please delete "can involve over frequencies" and insert --can involve frequencies" therefor.

In column 35, line 64, please delete "Yee," and insert --See-- therefor.

In column 35, line 64, please delete "*lipids*" and insert --*Lipids*-- therefor.

In column 37, line 52, please delete "1 βm" and insert --1 $\mu$m-- therefor.

UNITED STATES PATENT AND TRADEMARK OFFICE
CERTIFICATE OF CORRECTION

PATENT NO. : 5,846,517
DATED : December 8, 1998
INVENTOR(S) : Evan C. Unger

It is certified that error appears in the above-identified patent and that said Letters Patent is hereby corrected as shown below:

In column 37, line 61, please delete "size thereof For" and insert --size thereof. For-- therefor.

In column 38, line 8, please delete "10 lm" and insert --10 μm-- therefor.

In column 45, line 25, please delete "Kokal" and insert --Kokai-- therefor.

In column 45, line 39, please delete "*Phannacology*" and insert --*Pharmacology*-- therefor.

In column 45, line 46, please delete "Gamer" and insert --Garner-- therefor.

In column 48, line 30, please delete "bloactive" and insert --bioactive-- therefor.

In column 49, line 43, please delete "*Pharnmacological*" and insert --*Pharmacological*-- therefor.

In column 49, line 45, please delete "pp. $^7$43-751" and insert --pp. 743-751-- therefor.

In column 50, line 33, please delete "(4-phenylbuityl)" and insert --(4-phenylbutyl)-- therefor.

UNITED STATES PATENT AND TRADEMARK OFFICE
CERTIFICATE OF CORRECTION

PATENT NO. : 5,846,517
DATED : December 8, 1998
INVENTOR(S) : Evan C. Unger

It is certified that error appears in the above-identified patent and that said Letters Patent is hereby corrected as shown below:

In column 50, line 35, please delete "*Pharnacological*" and insert --*Pharmacological*-- therefor.

In column 51, line 43, please delete "*north*" and insert --*North*-- therefor.

In column 51, line 55, please delete "*I,chocardiography*" and insert --*Echocardiography*-- therefor.

In column 58, line 2, please delete "Mor-Avi V. Et. Al" and insert --Mor-Avi V. et al.-- therefor.

In column 59, line 17, please delete "NiH" and insert --NIH-- therefor.

In column 61, line 39, claim 12, please delete "phosphatidyl-choline" and insert --phosphatidylcholine-- therefor.

In column 61, line 41, claim 12, please delete "dimyristoyipllosphatidylcholine" and insert --dimyristoylphosphatidylcholine-- therefor.

In column 61, line 48, claim 14, please delete "dioleoylphospnatidylethanolamine" and insert --dioleoylphosphatidylethanolamine-- therefor.

UNITED STATES PATENT AND TRADEMARK OFFICE
CERTIFICATE OF CORRECTION

PATENT NO. : 5,846,517
DATED : December 8, 1998
INVENTOR(S) : Evan C. Unger

It is certified that error appears in the above-identified patent and that said Letters Patent is hereby corrected as shown below:

In column 61, line 56, claim 17, please delete "claim 18" and insert --claim 8-- therefor.

In column 62, line 14, claim 21, please delete "pentadiene-1-of" and insert --pentadiene-1-ol-- therefor.

In column 62, line 41, claim 27, please delete "perfluoromethale" and insert --perfluoromethane-- therefor.

Signed and Sealed this

Twenty-ninth Day of May, 2001

NICHOLAS P. GODICI

*Attest:*

*Attesting Officer*  *Acting Director of the United States Patent and Trademark Office*